US008039273B2

(12) United States Patent
Jeffrey

(10) Patent No.: US 8,039,273 B2
(45) Date of Patent: Oct. 18, 2011

(54) β-GLUCURONIDE-LINKER DRUG CONJUGATES

(75) Inventor: Scott Jeffrey, Snohomish, WA (US)

(73) Assignee: Seattle Genetics, Inc., Bothell, WA (US)

( * ) Notice: Subject to any disclaimer, the term of this patent is extended or adjusted under 35 U.S.C. 154(b) by 494 days.

(21) Appl. No.: 11/996,009

(22) PCT Filed: Jul. 18, 2006

(86) PCT No.: PCT/US2006/027925
§ 371 (c)(1),
(2), (4) Date: Jan. 17, 2008

(87) PCT Pub. No.: WO2007/011968
PCT Pub. Date: Jan. 25, 2007

(65) Prior Publication Data
US 2008/0241128 A1  Oct. 2, 2008

Related U.S. Application Data

(60) Provisional application No. 60/700,422, filed on Jul. 18, 2005, provisional application No. 60/779,076, filed on Mar. 4, 2006.

(51) Int. Cl.
*G01N 33/547* (2006.01)
*G01N 33/548* (2006.01)
*C07K 16/00* (2006.01)
*C07K 1/10* (2006.01)
*C07K 17/10* (2006.01)
*C12P 19/46* (2006.01)

(52) U.S. Cl. ............... 436/532; 530/402; 530/391.9; 436/528; 436/512; 436/544

(58) Field of Classification Search .................. None
See application file for complete search history.

(56) References Cited

U.S. PATENT DOCUMENTS

| | | | |
|---|---|---|---|
| 5,561,119 A | 10/1996 | Jacquesy et al. | |
| 5,851,527 A * | 12/1998 | Hansen | 424/178.1 |
| 6,361,774 B1 | 3/2002 | Griffiths et al. | |
| 6,884,869 B2 | 4/2005 | Senter et al. | |
| 6,906,182 B2 | 6/2005 | Ts'O et al. | |

FOREIGN PATENT DOCUMENTS

| | | |
|---|---|---|
| WO | WO 03/086312 A2 | 10/2003 |
| WO | WO 2004/010957 A2 | 2/2004 |

OTHER PUBLICATIONS

Albin, N. et al., "Main Drug-metabolizing Enzyme Systems in Human Breast Tumors and Perituморal Tissues," *Cancer Research*, Aug. 1, 1993, vol. 53, pp. 3541-3546.
Allen, T.M., "Ligand-Targeted Therapeutics in Anticancer Therapy," *Nature*, Oct. 2002, vol. 2, pp. 750-763.
Andrianomenjanahary, S. et al., "Synthesis of Novel Targeted Pro-Prodrugs of Anthracyclines Potentially Activated by a Monoclonal Antibody Galactosidase Conjugate (Part 1)," *Bioorganic & Medicinal Chemistry Letters*, 1992, vol. 2, No. 9, pp. 1093-1096.
Angenault, S. et al., "Cancer Chemotherapy: A SN-38 (7-Ethyl-10-hydroxycamptothecin) Glucuronide Prodrug for Treatment by a PMT (Prodrug MonoTherapy) Strategy," *Bioorganic & Medicinal Chemistry Letters*, 2003, vol. 13, pp. 947-950.
Asai, A. et al., "synthesis and Antitumor Activity of Water-soluble Duocarmycin B1 Prodrugs," *Bioorganic & Medicinal Chemistry Letters*, 1999, vol. 9, pp. 2995-2998.
Azoulay, M. et al., "Prodrugs of anthracycline antibiotics suited for tumor-specific activation," *Anti-Cancer Drug Design*, 1995, vol. 10, pp. 441-460.
Bakina, E. et al., "Intensely Cytotoxic Anthracycline Prodrugs: Glucuronides," *J. Med. Chem.*, 1997, vol. 40, No. 25, pp. 4013-4018.
Boons, G-J., ed., *Carbohydrate Chemistry*, Blackie Academic & Professional: London, United Kingdom, 1998, pp. 98-174.
Bosslet, K. et al., "Elucidation of the Mechanism Enabling Tumor Selective Prodrug Monotherapy," *Cancer Research*, Mar. 15, 1998, vol. 58, pp. 1195-1201.
Bross, P.F. et al., "Approval Summary: Gemtuzumab Ozogamicin in Relapsed Acute Myeloid Leukemia," *Clinical Cancer Research*, Jun. 2001, vol. 7, pp. 1490-1496.
Chen, X. et al., "Glucuronides in Anti-Cancer Therapy," *Curr. Med. Chem.-Anti-Cancer Agents*, 2003, vol. 3, No. 2, pp. 139-150.
De Graaf, M. et al., "Beta-Glucuronidase-Mediated Drug Release,"*Current Pharmaceutical Design*, 2002, vol. 8, No. 15, pp. 1391-1403.
De Graaf, M. et al. "Cytosolic β-glycosidases for activation of glycoside prodrugs of daunorubicin," *Biochemical Pharmacology*, 2003, vol. 65, pp. 1875-1881.
De Groot, F.M.H., et al., "Anticancer Prodrugs for Application in Monotherapy: Targeting Hypoxia, Tumor-Associated Enzymes, and Receptors," *Current Medicinal Chemistry*, 2001, vol. 8, No. 9, pp. 1093-1122.
Desai, A.A. et al., "*UGT* pharmcogenomics: implications for cancer risk and cancer therapeutics," *Pharmacogenetics*, 2003, vol. 13, No. 8, pp. 517-523.
Drueckhammer, D.G. et al., "Enzyme Catalysis in Synthetic Carbohydrate Chemistry," *Synthesis*, Jul. 1991, pp. 499-525.
Dubowchik, G.M. et al., "Receptor-mediated and enzyme-dependent targeting of cytotoxic anticancer drugs," *Pharmacology & Therapeutics*, 1999, vol. 83, pp. 67-123.
Fuselier, J.A. et al., "An Adjustable Release Rate Linking Strategy for Cytotoxin-Peptide Conjugates," *Bioorganic & Medicinal Chemistry Letters*, 2003, vol. 13, pp. 799-803.
Gesson, J.-P. et al., "Prodrugs of anthracyclines for chemotherapy via enzyme-monoclonal antibody conjugates," *Anti-Cancer Drug Design*, 1994, vol. 9, pp. 409-423.
Haisma, H.J. et al., "A monoclonal antibody-β-glucuronidase conjugate as activator of the prodrug epirubicin-glucuronide for specific treatment of cancer," *Br. J. Cancer*, 1992, vol. 66, pp. 474-478.

(Continued)

*Primary Examiner* — Shafiqul Haq
(74) *Attorney, Agent, or Firm* — Kilpatrick Townsend & Stockton LLP

(57) ABSTRACT

Ligand Drug conjugate compounds comprising a β-glucuronide-based linker and methods of using such compounds are provided.

27 Claims, 3 Drawing Sheets

OTHER PUBLICATIONS

Houba, P.H.J. et al., "Characterization of Novel Anthracycline Prodrugs Activated by Human β-glucuronidase for Use in Antibody-Directed Enzyme Prodrug Therapy," *Biochemical Pharmacology*, 1996, vol. 52, No. 3, pp. 455-463.

Huang, P.S. et al., "Drug-targeting strategies in cancer therapy," *Current Opinion in Genetics & Development*, 2001, vol. 11, pp. 104-110.

Jeffrey, S.C. et al., "Development and Properties of β-Glucuronide Linkers for Monoclonal Antibody-Drug Conjugates," *Bioconjugate Chem.*, 2006, vol. 17, pp. 831-840.

Kirschke, H., "Lysosomal Cysteine Peptidases and Malignant Tumours," *Cellular Peptidases in Immune Functions and Diseases*, Ansorge et al., eds., 1997, Plenum Press, New York, pp. 253-256.

Leenders, R.G.G. et al., "β-Glucuronyl Carbamate Based Pro-moieties Designed for Prodrugs in ADEPT," *Tetrahedron Letters*, 1995, vol. 36, No. 10, pp. 1701-1704.

Leenders, R.G.G. et al., "Synthesis and Evaluation of Novel Daunomycin-Phosphate-Sulfate-β-Glucuronide and -β-Glucoside Prodrugs for Application in Adept," *Bioorganic & Medicinal Chemistry Letters*, 1995, vol. 5, No. 24, pp. 2975-2960.

Leenders, R.G.G. et al., "Novel Anthracycline-space-β-glucuronide, -β-glucoside, and -β-galactoside Prodrugs for Application in Selective Chemotherapy," *Bioorganic & Medicinal Chemistry*, 1999, vol. 7, pp. 1597-1610.

Lougerstay-Madec, R. et al., "Synthesis of self-immolative glucuronide-based prodrugs of a phenol mustard," *Anti-Cancer Drug Design*, 1998, vol. 13, pp. 995-1007.

Papot, S. et al., "Design of Selectively Activated Anticancer Prodrugs: Elimination and Cyclization Strategies," *Curr. Med. Chem.—Anti-Cancer Agents*, 2002, vol. 2, No. 2, pp. 155-185.

Ritter, J.K., "Roles of glucuronidation and UDP-glucuronosyltransferases in xenobiotic bioactivation reactions," *Chemico-Biological Interactions*, 2000, vol. 129, pp. 171-193.

Schelté, P. et al., "Differential Reactivity of Maleimide and Bromoacetyl Functions with Thiols: Application to the Preparation of Liposomal Diepitope Constructs," *Bioconjugate Chem.*, 2000, vol. 11, pp. 118-123.

Schmidt, F. et al., "Cancer Chemotherapy: A Paclitaxel Prodrug for ADEPT (Antibody-Directed Enzyme Prodrug Therapy)," *Eur. J. Org. Chem.*, 2001, pp. 2129-2134.

Sperker, B. et al., "The Role of β-Glucuronidase in Drug Disposition and Drug Targeting in Humans," *Clin. Pharmacokinet*, Jul. 1997, vol. 33, No. 1, pp. 18-31.

Stachulski, A.V. et al., "The synthesis of O-glucuronides," *Natural Product Reports*, 1998, pp. 173-186.

Toshima, K. et al., "Recent Progress in O-Glycosylation Methods and Its Application to Natural Products Synthesis," *Chemical Reviews*, 1993, vol. 93, No. 4, pp. 1503-1531.

Verdier-Pinard, P. et al., "Sustained Intracellular Retention of Dolastatin 10 Causes Its Potent Antimitotic Activity," *Molecular Pharmacology*, 2000, vol. 57, pp. 180-187.

Wilbur, D.S. et al., "Biotin Reagents for Antibody Pretargeting. 5. Additional Studies of Biotin Conjugate Design to Provide Biotinidase Stability," *Bioconjugate Chem.*, 2001, vol. 12, pp. 616-623.

Desbéne, S. et al., "Doxorubicin prodrugs with reduced cytotoxicity suited for tumour-specific activation," *Anti-Cancer Dru Design*, 1998, vol. 13, pp. 955-968.

Eneyskaya, E.V. et al., "Chemo-enzymatic synthesis of 4-methylumbelliferyl β-(1→4)-D-xylooligosides: new substrates for β-D-xylanease assaus," *Org. Biomol. Chem.*, 2005, vol. 3, pp. 146-151.

Kelly, M.A. et al., "Preparation of some aryl α-L-arabinofuranosides as substrates for arabinofuranosides," *Carbohydrate Research*. 1988, vol. 181, pp. 262-266.

Marino, C. et al., "Synthesis of 4-methylcoumarin-7-yl β-D-galactofuranoside, a fluorogenic substrate for galactofuranosidase," *Carbohydrate Research*, 1995, vol. 276, pp. 209-213.

Sanderson et al., "In vivo Drug-Linker Stability of an Anti-CD30 Dipeptide-Linked Auristatin Immunoconjugate," *Clinical Cancer Research: An Official Journal of the American Association for Cancer Research*, Jan. 15, 2005, pp. 843-852, vol. 11, No. 2.

\* cited by examiner

β-GLUCURONIDE-LINKER DRUG CONJUGATES

RELATED APPLICATIONS

This application claims the benefit of U.S. Provisional Patent Application Nos. 60/700,422, filed Jul. 18, 2005, and 60/779,076, filed Mar. 4, 2006; the disclosures of which are incorporated by reference herein.

BACKGROUND

Monoclonal antibody therapies are gaining momentum as adjunct and front-line treatments for cancer. Successes of mAb therapies like AVASTIN (anti-VEGF) for colon cancer, RITUXAN (Rituximab; anti-CD20) for Non-Hodgkin's Lymphoma and HERCEPTIN (anti-Her2) for breast cancer have demonstrated that unconjugated antibodies can improve patient survival without the incidence of significantly increased toxicity.

Monoclonal antibodies (mAb) can be conjugated to a therapeutic agent to form an antibody drug conjugate (ADC). ADCs can exhibit increased efficacy, as compared to an unconjugated antibody. The linkage of the antibody to the drug can be direct, or indirect via a linker. One of components believed to be important for developing effective and well-tolerated ADCs is the composition and stability of the linker. For some types of ADCs, the linker desirably provides serum stability, yet selectively releases the drug at or within the target cell.

Attachment of a linker to a mAb can be accomplished in a variety of ways, such as through surface lysines, reductive-coupling to oxidized carbohydrates, and through cysteine residues liberated by reducing interchain disulfide linkages. A variety of ADC linkage systems have been described in the literature, including hydrazone-, disulfide- and peptide-based linkages. Some hydrazone and disulfide-based linkers can be labile in circulation, resulting in release of drug outside the targeted tissue. It is believed that this premature release of drug might lead to systemic toxicity or organ-specific toxicity and/or less than optimal therapeutic efficacy. Peptide-based linker strategies may provide linkers of higher stability; however, the increased associated hydrophobicity of some linkers may lead to aggregation, particularly with strongly hydrophobic drugs. Such aggregation may lead to non-specific uptake of the ADCs into non-targeted tissues, potentially affecting non-target toxicity.

β-glucuronides are metabolites produced in the liver and kidneys by a class of enzymes known as UDP-glucuronosyl transferases. These transferases are involved in a metabolic transformation leading to the clearance of xenobiotics from the body. Glucuronidation dramatically increases the solubility of substrate compounds, allowing more efficient renal clearance.

β-glucuronidase is a UDP-glucuronosyl transferase which is present in the lysosomes of essentially all human tissues. The enzyme catalyzes the hydrolysis of the glycosidic bond of glucuronides with β-configuration and is reported to have broad substrate specificity. It is most active at a low pH with the enzymatic efficiency dropping to approximately 10% at neutral pH. β-glucuronidase has been reported to be overexpressed in breast cancer tissue relative to peritumor tissue. In spite of its ubiquitous nature, the enzyme is effectively sequestered inside cell lysosomes, and minimal immunohistochemical staining is observed in the extracellular space of normal tissue samples. One exception is the β-glucuronidase activity seen in the intestinal tract, arising from the presence of E. coli.

In contrast to normal tissues, the interstitial space of necrotic tumor tissue displays high levels of β-glucuronidase activity. The source is believed to be inflammatory cells and not directly from the tumor tissue. Based on this observation, β-glucuronide prodrugs (primarily of doxorubicin) have been prepared for research in monotherapy. The rationale for this approach is that the β-glucuronide prodrug would be less toxic than free drug due to its inability to enter cells. The prodrug has two primary fates: prodrug in the vicinity of the tumor will be converted to free drug, while the remaining prodrug will be rapidly cleared through the kidneys. β-glucuronide prodrugs have been reported for use in ADEPT (Antibody Directed Enzyme Pro-drug Therapy). β-glucuronide prodrug-based therapies require, however, high systemic levels of prodrugs, which may be associated with undesired toxicities.

There remains a need, therefore, for targeted delivery of prodrugs, resulting in elimination of targeted cells while reducing toxicity to non-target cells.

There is a further need for ADCs with linker systems that provide a high level of linker serum stability and increased solubility, allowing the efficient conjugation of hydrophobic drugs and that effect intracellular delivery of drugs.

These and other limitations and problems of the past are solved by the present invention. (The recitation of any reference in this application is not an admission that the reference is prior art to this application.)

BRIEF SUMMARY

The present invention provides ligand drug conjugates and linker-drug conjugates for targeted delivery of drugs. The ligand drug conjugates include a ligand, such as an antibody, for targeting the conjugate to a target cell or tissue. The conjugates further include a β-glucuronide-based linker comprising a site that can be cleaved by an enzyme having β-glucuronidase activity. The linker is attached to the ligand and to a drug. The invention further provides methods of treating cancer, immune disease, infectious disease and other diseases or disorders using a ligand drug conjugate including a β-glucuronide-based linker. The ligand drug conjugates surprisingly yet exhibit serum stability to provide targeted delivery of linked drug to a target cell.

In one aspect, a ligand drug conjugate compound having the following formula:

$$L-(A_a-W_w-Y_y-D_{1-4})_p \qquad I$$

or a pharmaceutically acceptable salt or solvate thereof, wherein:
L- is a Ligand unit,
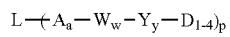-$A_a$—$W_w$—$Y_y$ is a Linker unit (LU),
-A- is an optional Stretcher unit,
a is 0, 1 or 2,
each —W— is independently a Glucuronide unit,
w is an integer ranging from 1 to 2,
—Y— is an optional self-immolative spacer unit,
y is 0, 1 or 2,
p ranges from 1 to about 20, and
-D is a Drug unit.

In some embodiments the Ligand is an antibody, such as a chimeric, humanized or human antibody or an antigen binding antibody fragment.

In some embodiments, the Glucuronide unit (—W—) comprises the formula:

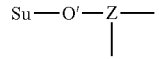

Su—O'—Z— wherein S is sugar moiety, —O'— is a glycosidic bond (e.g., cleavable by a β-glucuronidase) and Z is a self-immolative group; and wherein Z forms a first covalent bond with Y or D and a second covalent bond with L or A.

In some embodiments, the Glucuronide unit (—W—) comprises the formula:

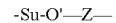

-Su-O'—Z— wherein S is sugar moiety, —O'— is a bond cleavable by a β-Glucuronidase and Z is a self-immolative group; and wherein Z forms a covalent bond with Y or D and Su forms a covalent bond with L or A.

In some embodiments, the Drug unit is selected from Formulas $D_E$ and $D_F$:

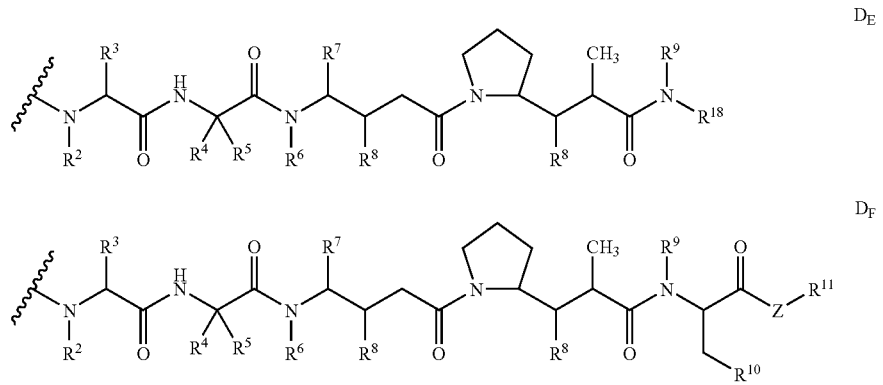

wherein:
- $R^2$ is selected from H and $C_1$-$C_8$ alkyl;
- $R^3$ is selected from H, $C_1$-$C_8$ alkyl, $C_3$-$C_8$ carbocycle, aryl, $X^1$-aryl, $X^1$—($C_3$-$C_8$ carbocycle), $C_3$-$C_8$ heterocycle and $X^1$—($C_3$-$C_8$ heterocycle);
- $R^4$ is selected from H, $C_1$-$C_8$ alkyl, $C_3$-$C_8$ carbocycle, aryl, $X^1$-aryl, $X^1$—($C_3$-$C_8$ carbocycle), $C_3$-$C_8$ heterocycle and $X^1$—($C_3$-$C_8$ heterocycle);
- $R^5$ is selected from H and methyl;
- or $R^4$ and $R^5$ jointly form a carbocyclic ring and have the formula —$(CR^aR^b)_n$— wherein $R^a$ and $R^b$ are independently selected from H, $C_1$-$C_8$ alkyl and $C_3$-$C_8$ carbocycle and n is selected from 2, 3, 4, 5 and 6;
- $R^6$ is selected from H and $C_1$-$C_8$ alkyl;
- $R^7$ is selected from H, $C_1$-$C_8$ alkyl, $C_3$-$C_8$ carbocycle, aryl, $X^1$-aryl, $X^1$—($C_3$-$C_8$ carbocycle), $C_3$-$C_8$ heterocycle and $X^1$—($C_3$-$C_8$ heterocycle);
- each $R^8$ is independently selected from H, OH, $C_1$-$C_8$ alkyl, $C_3$-$C_8$ carbocycle and O—($C_1$-$C_8$ alkyl);
- $R^9$ is selected from H and $C_1$-$C_8$ alkyl;
- $R^{10}$ is selected from aryl and $C_3$-$C_8$ heterocycle;
- Z is O, S, NH, or $NR^{12}$, wherein $R^{12}$ is $C_1$-$C_8$ alkyl;
- $R^{11}$ is selected from H, $C_1$-$C_{20}$ alkyl, aryl, $C_3$-$C_8$ heterocycle, —$(R^{13}O)_m$—$R^{14}$, and —$(R^{13}O)_m$—$CH(R^{15})_2$;
- m is an integer ranging from 1-1000;
- $R^{13}$ is $C_2$-$C_8$ alkyl;
- $R^{14}$ is H or $C_1$-$C_8$ alkyl;
- each occurrence of $R^{15}$ is independently H, COOH, —$(CH_2)_n$—$N(R^{16})_2$, —$(CH_2)_n$—$SO_3H$, or —$(CH_2)_n$—$SO_3$—$C_1$-$C_8$ alkyl;
- each occurrence of $R^{16}$ is independently H, $C_1$-$C_8$ alkyl, or —$(CH_2)_n$—COOH;
- $R^{18}$ is selected from —$C(R^8)_2$—$C(R^8)_2$-aryl, —$C(R^8)_2$—$C(R^8)_2$—($C_3$-$C_8$ heterocycle), and —$C(R^8)_2$—$C(R^8)_2$—($C_3$-$C_8$ carbocycle);
- $X^1$ is $C_1$-$C_{10}$ alkylene; and
- n is an integer ranging from 0 to 6.

In some embodiments, the Drug unit is Formula $D_F$:

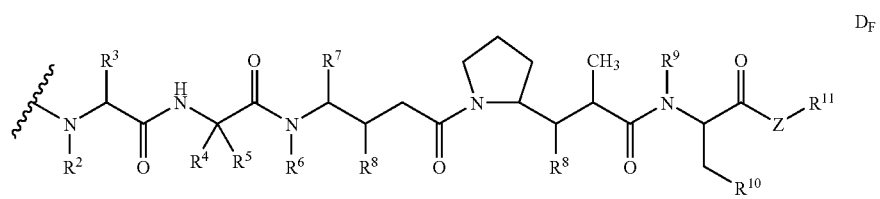

In some embodiments, the Drug unit has the formula:

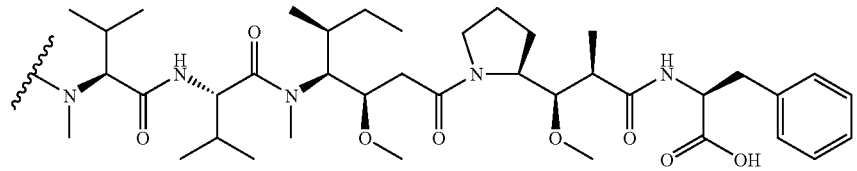

In some embodiments, the Drug unit has the formula $D_E$:

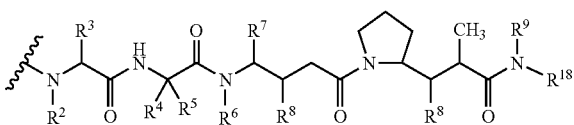

In some embodiments, the Drug unit has the formula:

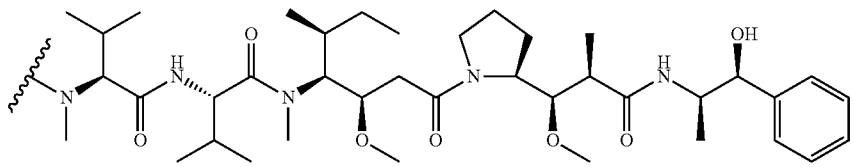

In some embodiments, the ligand drug conjugate compound has the following formula:

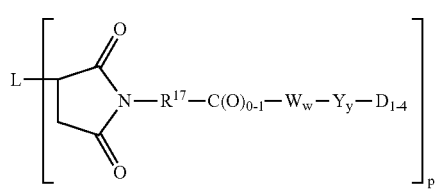

wherein $R^{17}$ is a direct bond of —$C_1$-$C_{10}$ alkylene-, —$C_3$-$C_8$ carbocyclo-, —O—($C_1$-$C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$ alkylene-, —($CH_2CH_2O)_r$—, —($CH_2CH_2O)_r$—$CH_2$—, or —($CH_2CH_2O)_r$—$CH_2$—$CH_2$—; and r is an integer ranging from 1-10.

In some embodiments, the ligand drug conjugate compound has the formula:

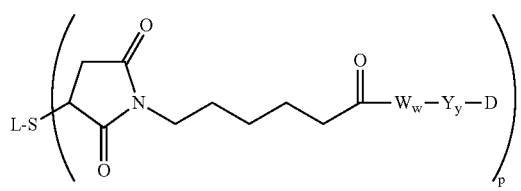

The ligand drug conjugate compounds can be formulated as a pharmaceutical composition comprising an effective amount of the ligand drug conjugate compound, or a pharmaceutically acceptable salt thereof, and a pharmaceutically acceptable diluent, carrier or excipient. The pharmaceutical composition optionally can include therapeutically effective amount of chemotherapeutic agent.

In another aspect, a method of killing or inhibiting the proliferation of tumor cells or cancer cells is provided. The methods generally include treating tumor cells or cancer cells with an amount of the ligand drug conjugate compound, or a pharmaceutically acceptable salt or solvate thereof, being effective to kill or inhibit the proliferation of the tumor cells or cancer cells.

In another aspect, a method for treating cancer is provided. The method generally includes administering to a patient an amount of the antibody-drug conjugate compound or a pharmaceutically acceptable salt or solvate thereof, the amount being effective to treat cancer. The method can optionally include administering an effective amount of an additional anticancer agent, an immunosuppressant agent or an anti-infectious agent.

In another aspect, a method for treating an autoimmune disease is provided. The method includes administering to a patient an amount of ligand drug conjugate compound, or a pharmaceutically acceptable salt or solvate thereof, the amount being effective to treat the autoimmune disease.

In another aspect, a method for treating an infectious disease is provided. The method generally includes administering to a patient an amount of the ligand drug conjugate compound or a pharmaceutically acceptable salt or solvate thereof, the amount being effective to treat the infectious disease.

These and other aspect of the invention will best be understood by reference to the following detailed description of the preferred embodiment, taken in conjunction with the accompanying drawings. The discussion below is descriptive, illustrative and exemplary and is not to be taken as limiting the scope defined by any appended claims.

DETAILED DESCRIPTION

Figure 1:
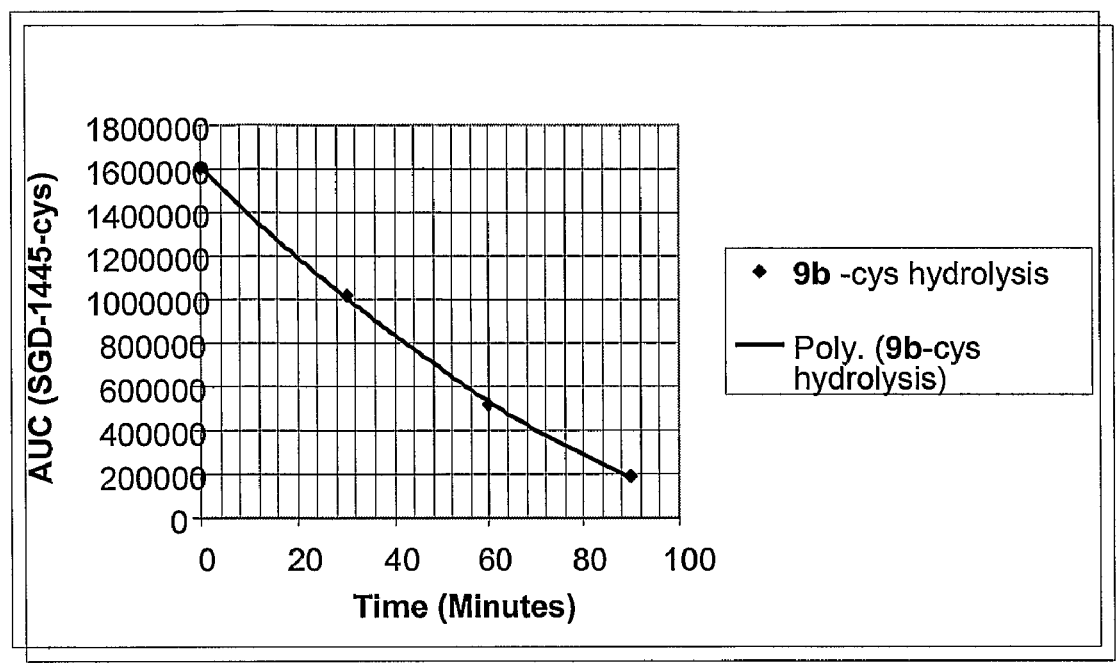
FIG. 1 shows the reactivity of a cysteine-quenched Glucuronide linker-MMAF conjugate with *E. coli* β-glucuronidase. Cysteine-quenched c1F6-9b was added to the enzyme and incubated at 37° C. Hydrolysis to free drug was monitored by HPLC (254 nm) with sampling every 30 min. Digestion half-life was 41 min.

For clarity of disclosure, and not by way of limitation, the detailed description of the invention is divided into the subsections which follow.

Definitions

Unless stated otherwise, the following terms and phrases as used herein are intended to have the following meanings. When trade names are used herein, the trade names includes the trade name product formulation, the generic drug, and the active pharmaceutical ingredient(s) of the trade name product, unless otherwise indicated by context.

The term "antibody" herein is used in the broadest sense and refers to intact monoclonal antibodies, polyclonal antibodies, multispecific antibodies (e.g., bispecific antibodies), and to antibody fragments that exhibit the desired biological activity (e.g., antigen binding). The antibody can be of any type or class (e.g., IgG, IgE, IgM, IgD, and IgA) or sub-class (e.g., IgG1, IgG2, IgG3, IgG4, IgA1 and IgA2).

An "intact" antibody is one which comprises an antigen-binding variable region as well as a light chain constant domain ($C_L$) and heavy chain constant domains, $C_H1$, $C_H2$, $C_H3$, and/or $C_H4$, as appropriate for the antibody class. The constant domains may be native sequence constant domains (e.g., human native sequence constant domains) or amino acid sequence variant thereof.

An antibody may have one or more "effector functions" which refer to those biological activities attributable to the Fc region (a native sequence Fc region or amino acid sequence variant Fc region) of an antibody. Examples of antibody effector functions include C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc.

"Single-chain Fv" or "scFv" antibody fragments comprise the $V_H$ and $V_L$ domains of an antibody, wherein these domains are present in a single polypeptide chain. The $F_v$ polypeptide typically further comprises a polypeptide linker between the $V_H$ and $V_L$ domains which enables the scFv to form the desired structure for antigen binding. For a review of scFv, see Plüuckthun in *The Pharmacology of Monoclonal Antibodies*, vol. 113, Rosenburg and Moore, eds., Springer-Verlag, New York, pp. 269-315 (1994).

The term "diabody" refers to a small antibody fragment with two antigen-binding sites, which fragment comprises a variable heavy domain ($V_H$) connected to a variable light domain ($V_L$) in the same polypeptide chain. By using a linker that is too short to allow pairing between the two domains ($V_H$–$V_L$) of the same chain, the domains are forced to pair with the complementary domains of another chain and create two antigen-binding sites. Diabodies are described more fully in, for example, EP 0 404 097; WO 93/11161; and Hollinger et al., 1993, *Proc. Natl. Acad. Sci. USA* 90:6444-6448. The two antigen-binding sites can be the same or different.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In some embodiments, the antibody will be purified (1) to greater than 95% by weight of antibody as determined by the Lowry method, or to greater than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or silver stain. Isolated antibody includes the antibody in situ within recombinant cells since at least one component of the antibody's natural environment will not be present. Ordinarily, however, isolated antibody will be prepared by at least one purification step.

An antibody "which binds" an antigen of interest is one capable of binding that antigen with sufficient affinity such that the antibody is useful in targeting a cell expressing the antigen.

The terms "specifically binds" and "specific binding" refer to antibody binding to a predetermined antigen. Typically, the antibody binds with an affinity of at least about $1 \times 10^7$ M$^{-1}$, and binds to the predetermined antigen with an affinity that is at least two-fold greater than its affinity for binding to a non-specific antigen (e.g., BSA, casein) other than the predetermined antigen or a closely-related antigen.

The term "therapeutically effective amount" refers to an amount of a drug (e.g., a ligand drug conjugate or linker drug conjugate) effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can, for example, be measured by assessing the time to disease progression (TTP) and/or determining the response rate (RR).

The terms "target polypeptide," "target protein" and "target antigen" refer to a protein, polypeptide, and in addition in the case of a "target antigen," another molecule on the surface of or associated with a target cell.

"Compound", as in the terms "compound of the formula", "compound of the formula", and the like, refers to and encompasses the chemical compound itself as well as, whether explicitly stated or not, and unless the context makes clear that the following are to be excluded: amorphous and crystalline forms of the compound, including polymorphic forms, where these forms may be part of a mixture or in isolation; free acid and free base forms of the compound, which are typically the forms shown in the structures provided herein; isomers of the compound, which refers to optical isomers, and tautomeric isomers, where optical isomers include enantiomers and diastereomers, chiral isomers and non-chiral isomers, and the optical isomers include isolated optical isomers as well as mixtures of optical isomers including racemic and non-racemic mixtures; where an isomer may be in isolated form or in admixture with one or more other isomers; isotopes of the compound, including deuterium- and tritium-containing compounds, and including compounds containing radioisotopes, including therapeutically- and diagnostically-effective radioisotopes; multimeric forms of the compound, including dimeric, trimeric, etc. forms; salts of the compound, preferably pharmaceutically acceptable salts, including acid addition salts and base addition salts, including salts having organic counterions and inorganic counterions, and including zwitterionic forms, where if a compound is associated with two or more counterions, the two or more counterions may be the same or different; and solvates of the compound, including hemisolvates, monosolvates, disolvates, etc., including organic solvates and inorganic solvates, said inorganic solvates including hydrates; where if a compound is associated with two or more solvent molecules, the two or more solvent molecules may be the same or different. In some instances, reference made herein to a compound of the invention will include an explicit reference to one or of the above forms, e.g., salts and solvates, however, this reference is for emphasis only, and is not to be construed as excluding other of the above forms as identified above.

The term "alkyl" refers to a straight chain or branched, saturated or unsaturated hydrocarbon having the indicated number of carbon atoms (e.g., "$C_1$-$C_8$ alkyl" refers to an alkyl group having from 1 to 8 carbon atoms). When the number of carbon atoms is not indicated, the alkyl group has from 1 to 8 carbon atoms. Representative "$C_1$-$C_8$ alkyl" groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)$—$CH(CH_3)_2$), 2,3-dimethyl-2-butyl (—$C(CH_3)_2CH(CH_3)_2$), and 3,3-dimethyl-2-butyl (—$CH(CH_3)C(CH_3)_3$). An alkyl group can be unsubstituted or substituted with one or more groups including, but not limited to, —O—($C_1$-$C_8$ alkyl), aryl, —C(O)R', —OC(O)R', —C(O)OR', —C(O)$NH_2$, —C(O)NHR', —C(O)N(R')$_2$—NHC(O)R', —$SO_3$R', —S(O)$_2$R', —S(O)$_2$R', —S(O)R', —OH, -halogen, —$N_3$, —$NH2$, —NH(R'), —N(R')$_2$ and —CN; where each R' is independently selected from H, unsubstituted $C_1$-$C_8$ alkyl and aryl.

The term "alkenyl" refers to a $C_2$-$C_{18}$ hydrocarbon containing normal, secondary, tertiary or cyclic carbon atoms with at least one site of unsaturation, I.e., a carbon-carbon, $sp^2$ double bond. Examples include, but are not limited to: ethylene or vinyl (—CH=$CH_2$), allyl (—$CH_2$CH=$CH_2$), cyclopentenyl (—$C_5H_7$), and 5-hexenyl (—$CH_2CH_2CH_2CH_2$CH=$CH_2$).

The term "alkynyl" refers to a $C_2$-$C_{18}$ hydrocarbon containing normal, secondary, tertiary or cyclic carbon atoms with at least one site of unsaturation, i.e., a carbon-carbon, sp triple bond. Examples include, but are not limited to: acetylenic (—C≡CH) and propargyl (—$CH_2$C≡CH).

The term "alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylenes include, but are not limited to: methylene (—$CH_2$—) 1,2-ethyl (—$CH_2CH_2$—), 1,3-propyl (—$CH_2CH_2CH_2$—), 1,4-butyl (—$CH_2CH_2CH_2CH_2$—), and the like.

The term "alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to: 1,2-ethylene (—CH=CH—).

The term "alkynylene" refers to an unsaturated, branched or straight chain or cyclic hydrocarbon radical of 2-18 carbon atoms, and having two monovalent radical centers derived by the removal of two hydrogen atoms from carbon atoms of a parent alkyne. Typical alkynylene radicals include, but are not limited to: acetylene (—C≡C—), propargyl (—$CH_2$C≡C—), and 4-pentynyl (—$CH_2CH_2CH_2$C≡C—).

The term "aryl" refers to a monovalent aromatic hydrocarbon radical of 6-20 carbon atoms derived by the removal of one hydrogen atom from a single carbon atom of a parent aromatic ring system. Some aryl groups are represented in the exemplary structures as "Ar". An aryl group can be unsubstituted or substituted. Typical aryl groups include, but are not limited to, radicals derived from benzene, substituted benzene, phenyl, naphthalene, anthracene, biphenyl, and the like. An aryl can be substituted with one or more groups including, but not limited to, —$C_1$-$C_8$ alkyl, —O—($C_1$-$C_8$ alkyl), —C(O)R', —OC(O)R', —C(O)OR', —C(O)$NH_2$, —C(O)NHR', —C(O)N(R')$_2$ —NHC(O)R', —S(O)$_2$R', —S(O)R', —OH, -halogen, —$N_3$, —$NH_2$, —NH(R'), —N(R')$_2$ and —CN; wherein each R' is independently selected from H, —$C_1$-$C_8$ alkyl and unsubstituted aryl.

The term "arylalkyl" refers to an acyclic alkyl radical in which one of the hydrogen atoms bonded to a carbon atom, typically a terminal or $sp^3$ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl, and the like. The arylalkyl group comprises 6 to 20 carbon atoms, e.g., the alkyl moiety, including alkanyl, alkenyl or alkynyl groups, of the arylalkyl group is 1 to 6 carbon atoms and the aryl moiety is 5 to 14 carbon atoms.

The term "heteroarylalkyl" refers to an acyclic alkyl radical in which one of the hydrogen atoms bonded to a carbon atom, typically a terminal or $sp^3$ carbon atom, is replaced with a heteroaryl radical. Typical heteroarylalkyl groups include, but are not limited to, 2-benzimidazolylmethyl, 2-furylethyl, and the like. The heteroarylalkyl group comprises 6 to 20 carbon atoms, e.g., the alkyl moiety, including alkanyl, alkenyl or alkynyl groups, of the heteroarylalkyl group is 1 to 6 carbon atoms and the heteroaryl moiety is 5 to 14 ring atoms, typically 1 to 3 heteroatoms selected from N, O, P, and S, with the remainder being carbon atoms. The heteroaryl moiety of the heteroarylalkyl group may be a monocycle having 3 to 7 ring members (2 to 6 carbon atoms) or a bicycle having 7 to 10 ring members (4 to 9 carbon atoms) and 1 to 3 heteroatoms selected from N, O, P, and S, for example: a bicyclo [4,5], [5,5], [5,6], or [6,6] system.

The term "arylene" refers to an aryl group which has two covalent bonds and can be in the para, meta, or ortho configurations as shown in the following structures:

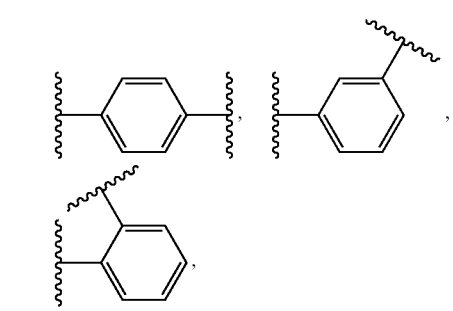

in which the phenyl group can be unsubstituted or substituted with up to four groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N(R')$_2$ —NHC(O)R', —S(O)$_2$R', —S(O)R', —OH, -halogen, —$N_3$, —NH$_2$, —NH(R'), —N(R')$_2$ and —CN; wherein each R' is independently selected from H, —C$_1$-C$_8$ alkyl and aryl.

The terms "substituted alkyl", "substituted aryl", and "substituted arylalkyl" refer to alkyl, aryl, and arylalkyl, respectively, in which one or more hydrogen atoms are each independently replaced with a substituent. Typical substituents include, but are not limited to, —X, —R, —O$^-$, —OR, —SR, —S$^-$, —NR$_2$, —NR$_3$, =NR, —CX$_3$, —CN, —OCN, —SCN, —N=C=O, —NCS, —NO, —NO$_2$, =N$_2$, —N$_3$, NRC(=O)R, —C(=O)R, —C(=O)NR$_2$, —SO$_3^-$, -SO$_3$H, —S(=O)$_2$R, —OS(=O)$_2$OR, —S(=O)$_2$NR, —S(=O)R, —OP(=O)(OR)$_2$, —P(=O)(OR)$_2$, —PO$^-_3$, —PO$_3$H$_2$, —C(=O)R, —C(=O)X, —C(=S)R, —CO$_2$R, —CO$_2^-$, —C(=S)OR, —C(=O)SR, —C(=S)SR, —C(=O)NR$_2$, —C(=S)NR$_2$, and —C(=NR)NR$_2$, where each X is independently a halogen: F, Cl, Br, or I; and each R is independently —H, C$_2$-C$_{18}$ alkyl, C$_6$-C$_{20}$ aryl, C$_3$-C$_{14}$ heterocycle, protecting group or prodrug moiety. Alkylene, alkenylene, and alkynylene groups as described above may also be similarly substituted.

The terms "heteroaryl" and "heterocycle" refer to a ring system in which one or more ring atoms is a heteroatom, e.g., nitrogen, oxygen, phosphate and sulfur. The heterocycle radical comprises 1 to 20 carbon atoms and 1 to 3 heteroatoms selected from N, O, P, and S. A heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo [4,5], [5,5], [5,6], or [6,6] system. Heterocycles are described in Paquette, "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. 82:5566 (1960).

Examples of heterocycles include, by way of example and not limitation, pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon-bonded heterocycles are bonded at the following positions: position 2, 3, 4, 5, or 6 of a pyridine; position 3, 4, 5, or 6 of a pyridazine; position 2, 4, 5, or 6 of a pyrimidine; position 2, 3, 5, or 6 of a pyrazine; position 2, 3, 4, or 5 of a furan, tetrahydrofuran, thiofuran, thiophene, pyrrole or tetrahydropyrrole; position 2, 4, or 5 of an oxazole, imidazole or thiazole; position 3, 4, or 5 of an isoxazole, pyrazole, or isothiazole; position 2 or 3 of an aziridine; position 2, 3, or 4 of an azetidine; position 2, 3, 4, 5, 6, 7, or 8 of a quinoline; or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl and 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, or 1H-indazole; position 2 of a isoindole or isoindoline; position 4 of a morpholine; and position 9 of a carbazole or β-carboline. Still more typically, nitrogen bonded heterocycles include 1-aziridyl, 1-azetedyl, 1-pyrrolyl, 1-imidazolyl, 1-pyrazolyl and 1-piperidinyl.

The term "carbocycle" refers to a saturated or unsaturated ring having 3 to 7 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cycloheptyl and cyclooctyl.

A "C$_3$-C$_8$ carbocycle" is a 3-, 4-, 5-, 6-, 7- or 8-membered saturated or unsaturated non-aromatic carbocyclic ring. Representative C$_3$-C$_8$ carbocycles include, but are not limited to, -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl and -cyclooctadienyl. A C$_3$-C$_8$ carbocycle group can be unsubstituted or substituted with one or more groups including, but not limited to, —C$_1$-C$_8$ alkyl, —O—(C$_1$-C$_8$ alkyl), -aryl, —C(O)R', —OC(O)R', —C(O)OR', —C(O)NH$_2$, —C(O)NHR', —C(O)N(R')$_2$, —NHC(O)R', —S(O)$_2$R', —S(O)R', —OH, -halogen, —N$_3$, —NH$_2$, —NH(R'), —N(R')$_2$ and —CN; where each R' is independently selected from H, -C$_1$-C$_8$ alkyl and aryl.

A "C$_3$-C$_8$ carbocyclo" refers to a C$_3$-C$_8$ carbocycle group defined above wherein one of the carbocycle groups' hydrogen atoms is replaced with a bond.

A "C$_1$-C$_{10}$ alkylene" is a straight chain, saturated hydrocarbon group of the formula —(CH$_2$)$_{1-10}$—. Examples of a C$_1$-C$_{10}$ alkylene include methylene, ethylene, propylene, butylene, pentylene, hexylene, heptylene, ocytylene, nonylene and decalene.

A "C$_3$-C$_8$ heterocycle" refers to an aromatic or non-aromatic C$_3$-C$_8$ carbocycle in which one to four of the ring carbon atoms are independently replaced with a heteroatom from the group consisting of O, S and N. Representative examples of a C$_3$-C$_8$ heterocycle include, but are not limited to, benzofuranyl, benzothiophene, indolyl, benzopyrazolyl, coumarinyl, isoquinolinyl, pyrrolyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl and tetrazolyl. A C$_3$-C$_8$ heterocycle can be unsubstituted or substituted with up to seven groups including, but not limited to, —C$_1$-C$_8$ alkyl, —O—(C$_1$-C$_8$ alkyl), -aryl, —C(O)R', —OC(O)R', —C(O)OR', —C(O)NH$_2$, —C(O)NHR', —C(O)N(R')$_2$, —NHC(O)R', —S(O)$_2$R', —S(O)R', —OH, -halogen, —N$_3$, —NH$_2$, —NH(R'), —N(R')$_2$ and —CN; wherein each R' is independently selected from H, —C$_1$-C$_8$ alkyl and aryl.

"C$_3$-C$_8$ heterocyclo" refers to a C$_3$-C$_8$ heterocycle group defined above wherein one of the heterocycle group's hydrogen atoms is replaced with a bond. A C$_3$-C$_8$ heterocyclo can be unsubstituted or substituted with up to six groups including, but not limited to, —C$_1$-C$_8$ alkyl, —O—(C$_1$-C$_8$ alkyl), -aryl, —C(O)R', —OC(O)R', —C(O)OR', —C(O)NH$_2$, —C(O)NHR', —C(O)N(R')$_2$ —NHC(O)R', —S(O)$_2$R', —S(O)R', —OH, -halogen, —N$_3$, —NH$_2$, —NH(R'), —N(R')$_2$ and —CN; wherein each R' is independently selected from H, —C$_1$-C$_8$ alkyl and aryl.

The phrase "pharmaceutically acceptable salt" refers to a pharmaceutically acceptable organic or inorganic salt of a ligand drug conjugate or linker drug conjugate. The conjugates may contain at least one amino group, and accordingly acid addition salts can be formed with the amino group. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate (i.e., 1,1' methylene bis -(2 hydroxy 3 naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

The phrases "pharmaceutically acceptable solvate" or "solvate" refer to an association of one or more solvent molecules and a ligand drug conjugate or linker drug conjugate. Examples of solvents that form pharmaceutically acceptable solvates include, but are not limited to, water, isopropanol, ethanol, methanol, DMSO, ethyl acetate, acetic acid, and ethanolamine.

Examples of a "patient" or "subject" include, but are not limited to, a human, rat, mouse, guinea pig, monkey, pig, goat, cow, horse, dog, cat, bird and fowl. In an exemplary embodiment, the patient or subject is a human.

The terms "treat" or "treatment," unless otherwise indicated by context, refer to both therapeutic treatment and prophylactic or preventative measures, wherein the object is to prevent or slow down (lessen) an undesired physiological change or disorder, such as the development or spread of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

In the context of cancer, the term "treating" includes any or all of: preventing growth of tumor cells, cancer cells, or of a tumor; preventing replication of tumor cells or cancer cells, lessening of overall tumor burden or decreasing the number of cancerous cells, and ameliorating one or more symptoms associated with the disease.

In the context of an autoimmune disease, the term "treating" includes any or all of: preventing replication of cells associated with an autoimmune disease state including, but not limited to, cells that produce an autoimmune antibody, lessening the autoimmune-antibody burden and ameliorating one or more symptoms of an autoimmune disease.

In the context of an infectious disease, the term "treating" includes any or all of: preventing the growth, multiplication or replication of the pathogen that causes the infectious disease and ameliorating one or more symptoms of an infectious disease.

The following abbreviations are used herein: MMAE is mono-methyl auristatin E (MW 718); MMAF is N-methylvaline-valine-dolaisoleuine-dolaproine-phenylalanine (MW 731.5); AEVB is auristatin E valeryl benzylhydrazone, acid labile linker through the C-terminus of AE (MW 732); DMSO is dimethylsulfoxide; DMF is N,N dimethylformamide; HPLC is high pressure liquid chromatography, THF is tetrahydrofuran; and Mc-OSu is maleimidocaproyl N-hydroxysuccimidyl ester.

Ligand Drug Conjugates

The present invention is drawn to a series of drug linker compounds and conjugate compounds containing a Drug compound (-D) and a Linker unit comprising a Glucuronide unit (—W—). The drug-linker compounds are useful as discrete entities, or can be conjugated to Ligands (L, in some embodiments, antibodies). The Linker unit can operate to provide a suitable, targeted release of a Drug compound(s). Additionally, some Linker Units can have multiple attached drugs (e.g., one to four attached drugs can be represented as -LU-(D)$_{1-4}$).

In one group of embodiments, the ligand drug conjugate compounds generally comprise the following formula I:

$$L-(A_a-W_w-Y_y-D_{1-4})_p \qquad I$$

or a pharmaceutically acceptable salt or solvate thereof, wherein:

L- is a Ligand unit,

-A$_a$—W$_w$—Y$_y$- is a Linker unit (LU),

-A- is an optional Stretcher unit, a is 0, 1 or 2, each —W— is independently a Glucuronide unit, w is an integer ranging from 1 to 2, —Y— is an optional self-immolative spacer unit, y is 0, 1 or 2, p ranges from 1 to 20, and -D is a Drug unit.

In some embodiments, a is 0 or 1, w is 1, and y is 0, 1 or 2. In some embodiments, a is 0 or 1, w is 1, and y is 0 or 1. In some embodiments, a is 0, w is 1, and y is 0. In some embodiments, a is 0 or 1, w is 1, and y is 1. In some embodiments, a is 1, w is 1, and y is 0. In some embodiments, a is 1, w is 1, and y is 1. In some embodiments, p is 1 to 10, 1 to 8, 1 to 6, 1 to 4, 6, 4 or 2. Each of these units is described in more detail herein.

Linker Units

A "Linker unit" (LU) is a bifunctional compound which can be used to link a Drug unit and a Ligand unit to form a Ligand Drug Conjugate compound (also referred to as a Ligand-Linker-Drug conjugate compound), to a Drug unit to form a Linker-Drug unit, or which is useful in the formation of immunoconjugates. In some embodiments, the Linker unit has the formula:

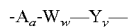

wherein: -A- is an optional Stretcher unit, a is 0, 1 or 2, each -W- is independently a Glucuronide unit, w is an integer ranging from 1 to 2, -Y- is an optional self-immolative Spacer unit, and y is 0, 1 or 2.

In some embodiments, a is 0 or 1, w is 1, and y is 0, 1 or 2. In some embodiments, a is 0 or 1, w is 1, and y is 0 or 1.

The Glucuronide Unit

The Glucuronide unit (—W—) links a Stretcher unit to a Spacer unit if the Stretcher and Spacer units are present, links a Stretcher unit to the Drug moiety if the Spacer unit is absent, and links the Ligand unit to the Drug unit if the Stretcher and Spacer units are absent. The Glucuronide unit includes a site that can be cleaved by a β-glucuronidase enzyme.

In some embodiments, the Glucuronide unit comprises a sugar moiety (Su) linked via a glycoside bond (—O'—) to a self-immolative group (Z) of the formula:

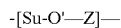    IIa

The glycosidic bond (—O'—) is typically a β-glucuronidase-cleavage site, such as a bond cleavable by human, lysosomal β-glucuronidase.

In the context of a Glucuronide unit, the term "self-immolative group" refers to a di- or tri-functional chemical moiety that is capable of covalently linking together two or three spaced chemical moieties (i.e., the sugar moiety (via a glycosidic bond), a Drug unit (directly or indirectly via a Spacer unit), and, in some embodiments, a Ligand unit (directly or indirectly via a Stretcher unit) into a stable molecule. The self-immolative group will spontaneously separate from the first chemical moiety (e.g., the Spacer or Drug unit) if its bond to the Sugar moiety is cleaved.

In some embodiments, the Sugar moiety (Su) is cyclic hexose, such as a pyranose, or a cyclic pentose, such as a furanose. In some embodiments, the pyranose is a glucuronide or hexose. The Sugar moiety is usually in the β-D conformation. In a specific embodiment, the pyranose is a β-D-glucuronide moiety (i.e., β-D-glucuronic acid linked to the self-immolative group —Z— via a glycosidic bond that is cleavable by β-glucuronidase). In some embodiments, the sugar moiety is unsubstituted (e.g., a naturally occurring cyclic hexose or cyclic pentose). In other embodiments, the sugar moiety can be a substituted β-D-glucuronide (i.e., glucuronic acid substituted with one or more group, such hydrogen, hydroxyl, halogen, sulfur, nitrogen or lower alkyl.

In some embodiments, the self-immolative group Z is a p-aminobenzyl alcohol (PAB) unit, as further described herein. Other suitable self immolative groups are known in the art.

In some embodiments, the Glucuronide unit has one of the following formulae:

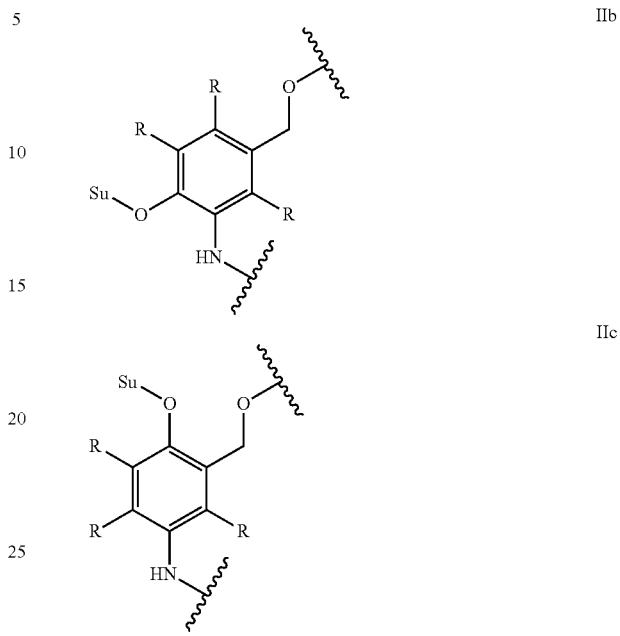

wherein Su is the Sugar moiety, the glycosidic bond comprises the oxygen bond between Su and the self immolative group Z, and each R is independently hydrogen, halo (e.g., chloro, bromo, fluoro, etc), —CN, —NO$_2$, or other electron withdrawing or donating group, provided that the Glucuronide unit (and Z in particular) undergoes self-immolation upon cleavage of the glycosidic bond. In some embodiments, each R is independently hydrogen, halo (e.g., chloro, bromo, fluoro, etc), —CN or —NO$_2$.

In some embodiments, the Glucuronide unit has one of the following formulae:

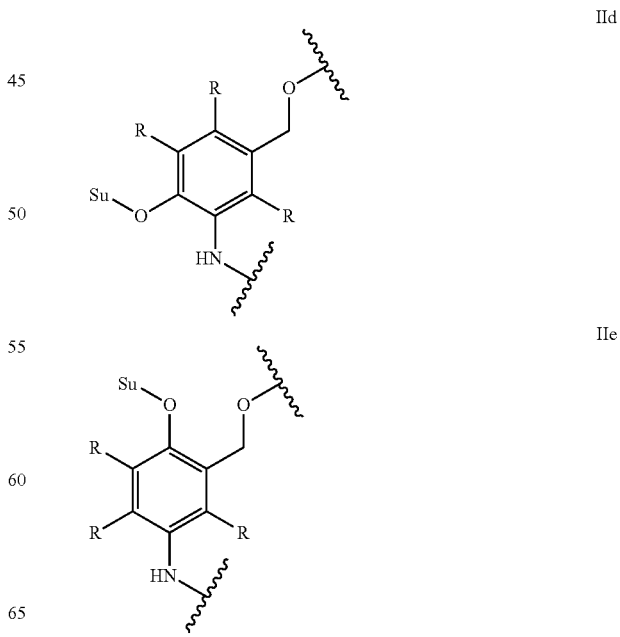

wherein Su is the Sugar moiety, the glycosidic bond (—O'—) comprises the oxygen bond between Su and the self immolative group Z, and each R is independently hydrogen.

In some embodiments, the self-immolative group (Z) is covalently linked to the Sugar moiety, to the Drug unit (directly or indirectly via the Spacer unit(s)), and to the Ligand unit (directly or indirectly via the Stretcher unit(s)). In some embodiments, a Drug Linker conjugate has the following formula:

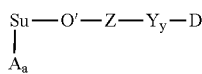

IIf wherein Su, O', Z, Y, y, D, A and a are defined as above. Typically from 1 to 20 of such Drug-Linker conjugates can be linked to a Ligand unit.

In some embodiments, a Ligand Drug conjugate compound (e.g., an antibody drug conjugate (ADC)) comprising the Glucuronide unit has one of the following formulae:

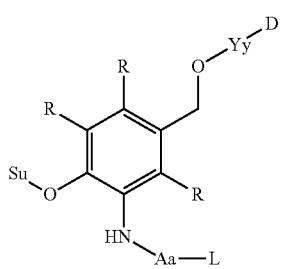

IIg

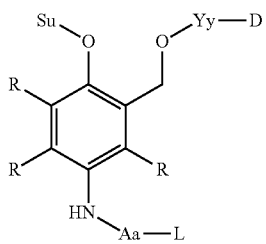

IIh wherein Su, Y, y, D, A, a, R and L are defined as described above.

In some embodiments, a Ligand Drug conjugate compound comprising the Glucuronide unit has the following formula:

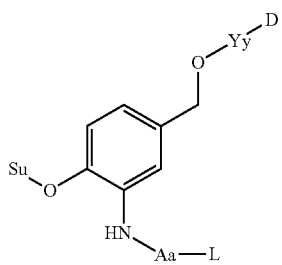

IIi wherein Su, Y, y, D, A, a and L are defined as described above.

In some embodiments, a Ligand Drug conjugate compound comprising the Glucuronide unit has the following formula:

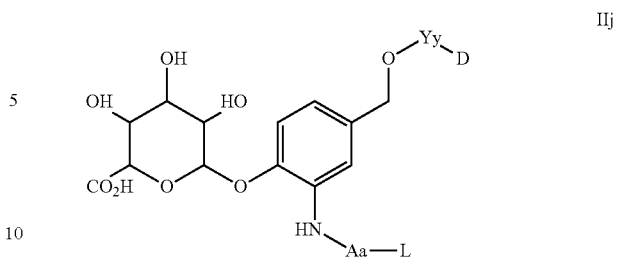

IIj wherein Y, y, D, A, a and L are defined as above.

In some embodiments, a Ligand Drug conjugate compound comprising the Glucuronide unit has the following formula:

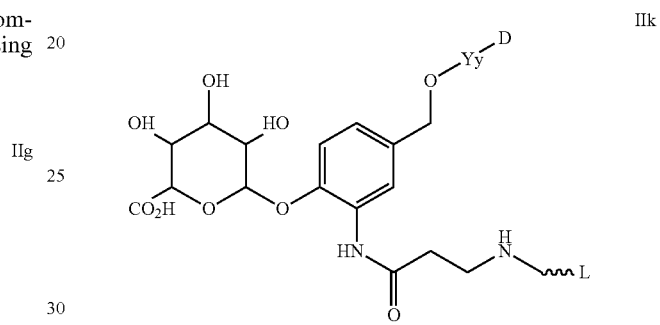

IIk wherein Y, y, D and L are defined as described above.

In some embodiments, a Ligand Drug conjugate compound comprising the Glucuronide unit has the following formula:

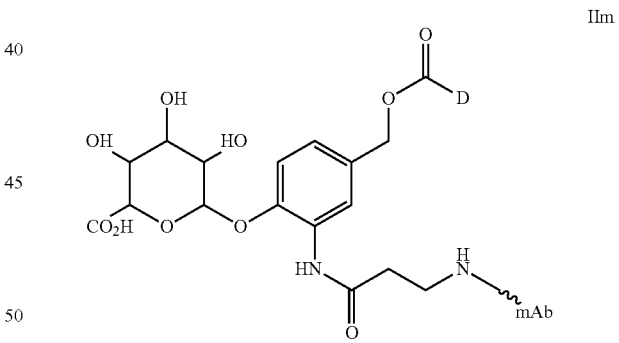

IIm wherein D is as described above and mAb is a monoclonal antibody.

In another group of embodiments, the Ligand unit is linked (directly or indirectly) to the Sugar moiety (S), which is linked to the self-immolative group (Z) which is linked (directly or indirectly) to the Drug unit, according to the following formula.

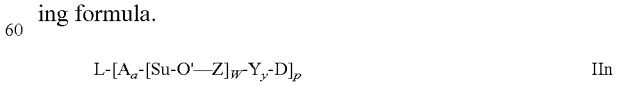

IIn wherein A, a, Su, O', Z, w, Y, y, D and L are defined as described above. For example, the Sugar moiety (Su) can be linked directly to the Ligand unit or indirectly via a Stretcher unit. The self-immolative group (Z) can be linked directly to the Drug unit or indirectly via a Spacer unit.

In related embodiments, a Drug-Linker compound has the following formula:

$$A_a\text{-}[Su\text{-}O'\text{---}Z]_w\text{-}Y_y\text{-}D \qquad \text{IIo}$$

wherein A, a, Su, O', Z, w, Y, y and D are defined as above. Typically from 1 to 20 of such Drug-Linker compounds can be linked to a Ligand unit.

The Stretcher Unit

The Stretcher unit (-A-), when present, is capable of linking a Ligand unit to a Glucuronide unit (—W—). In this regard, a Ligand unit (L) has a functional group that can form a bond with a functional group of a Stretcher. Useful functional groups that can be present on a Ligand unit, either naturally or via chemical manipulation include, but are not limited to, sulfhydryl (—SH), amino, hydroxyl, carboxy, the anomeric hydroxyl group of a carbohydrate, and carboxyl. In some embodiments, the Ligand unit functional groups are sulfhydryl and/or amino. Sulfhydryl groups can be generated by reduction of an intramolecular disulfide bond of a Ligand. Sulfhydryl groups also can be generated by reaction of an amino group of a lysine moiety of a Ligand using 2-iminothiolane (Traut's reagent) or another sulfhydryl generating reagent.

In one embodiment, the Stretcher unit forms a bond with a sulfur atom of the Ligand unit. The sulfur atom can be derived from a sulfhydryl group of a Ligand. Representative Stretcher units of this embodiment are depicted within the square brackets of Formulas IIIa and IIIb, wherein L-, —W—, —Y—, -D, w and y are as defined above, and $R_{17}$ is direct bond or selected from —$C_1$-$C_{10}$ alkylene-, —$C_3$-$C_8$ carbocyclo-, —O—($C_1$-$C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$ alkylene-, —($CH_2CH_2O)_r$—, —($CH_2CH_2O)_r$—$CH_2$—, and —($CH_2CH_2O)_r$—$CH_2$—$CH_2$—; and r is an integer ranging from 1-10. It is to be understood from all the exemplary embodiments of Formula I, such as III-VI, that even where not denoted expressly, from 1 to 20 drug moieties are linked to a Ligand (p=1-20).

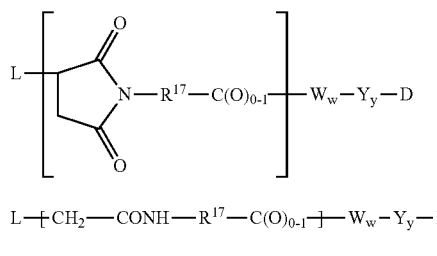

IIIa

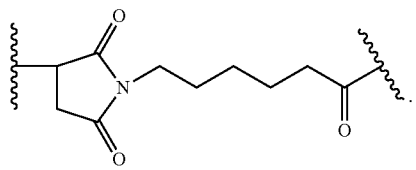

IIIb

An illustrative Stretcher unit is that of Formula IIIa wherein $R^{17}$ is —$(CH_2)_5$—:

Another illustrative Stretcher unit is that of Formula IIa wherein $R^{17}$ is —$(CH_2CH_2O)_r$—$CH_2$—; and r is 2:

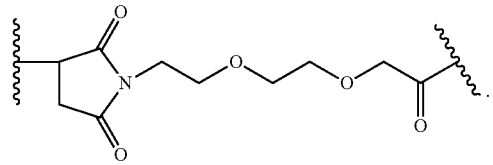

Another illustrative Stretcher unit is that of Formula IIIa wherein $R^{17}$ is —$(CH_2CH_2O)_r$—$CH_2$—$CH_2$—; and r is 2:

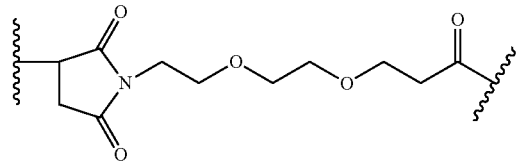

Another illustrative Stretcher unit is that of Formula III wherein $R^{17}$ is —$(CH_2CH_2O)_r$—$CH_2$—$CH_2$—; and r is 2

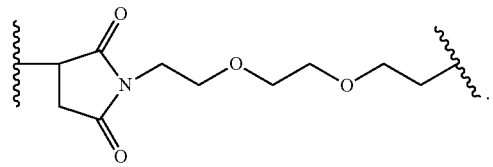

Still another illustrative Stretcher unit is that of Formula IIIb wherein $R^{17}$ is —$(CH_2)_5$—:

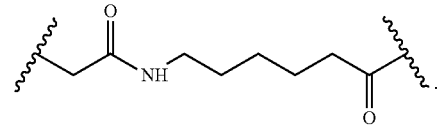

In another embodiment, the Stretcher unit is linked to the Ligand unit via a disulfide bond between a sulfur atom of the Ligand unit and a sulfur atom of the Stretcher unit. A representative Stretcher unit of this embodiment is depicted within the square brackets of Formula IV, wherein $R_{17}$, L-, —W—, —Y—, -D, w and y are as defined above.

IV

In yet another embodiment, the reactive group of the Stretcher contains a reactive site that can form a bond with a primary or secondary amino group of a Ligand. Examples of these reactive sites include, but are not limited to, activated esters such as succinimide esters, 4-nitrophenyl esters, pentafluorophenyl esters, tetrafluorophenyl esters, anhydrides, acid chlorides, sulfonyl chlorides, isocyanates and isothiocyanates. Representative Stretcher units of this embodiment are depicted within the square brackets of Formulas Va and Vb, wherein —$R_{17}$—, L-, —W—, —Y—, -D, w and y are as defined above;

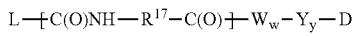    (Va)

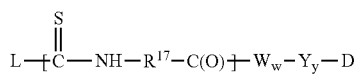    (Vb)

In some embodiments, the reactive group of the Stretcher contains a reactive site that is reactive to a modified carbohydrate (—CHO) group that can be present on a Ligand. For example, a carbohydrate can be mildly oxidized using a reagent such as sodium periodate and the resulting (—CHO) unit of the oxidized carbohydrate can be condensed with a Stretcher that contains a functionality such as a hydrazide, an oxime, a primary or secondary amine, a hydrazine, a thiosemicarbazone, a hydrazine carboxylate, and an arylhydrazide such as those described by Kaneko et. al., 1991, Bioconjugate Chem. 2:133 41. According to another example, a modified carbohydrate can be prepared by reductive amination. Representative Stretcher units of this embodiment are depicted within the square brackets of Formulas VIa, VIb, and VIc, wherein —$R_{17}$—, L-, —W—, —Y—, -D, w and y are as defined above.

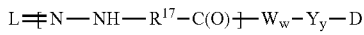    (VIa)

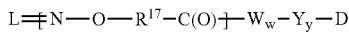    (VIb)

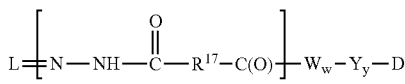    (VIc)

The Spacer Unit

The Spacer unit (—Y—), when present, links a Glucuronide unit to the Drug moiety. In some embodiments, the Spacer unit(s) is a self-immolative spacer. In this context, the term "self-immolative spacer" refers to a bifunctional chemical moiety that is capable of covalently linking together two spaced chemical moieties into a normally stable tripartite molecule. It will spontaneously separate from the second chemical moiety if its bond to the first moiety is cleaved.

In some embodiments, —Y—is linked to -Ww - via the methylene carbon atom of the self-immolative group, and linked connected directly to -D via a carbonate, carbamate or ether group. Without being bound by any particular theory or mechanism, Scheme 1 depicts a mechanism of Drug release of a glucuronide-based linker which is attached directly to -D via a carbonate group.

In some embodiments, —Yy- is a p-aminobenzyl alcohol (PAB) unit (see, e.g., Schemes 1 and 2, infra) whose phenylene portion is substituted with $Q_m$ wherein Q is —C1-C8 alkyl, —O—(C1-C8 alkyl), -halogen, -nitro or -cyano; and m is an integer ranging from 0-4. In another embodiment, —Yy- can be a carbonate group.

Other examples of self-immolative spacers include, but are not limited to, aromatic compounds that are electronically similar to the PAB group such as 2-aminoimidazol-5-methanol derivatives (see, e.g., Hay et. al., 1999, Bioorg. Med. Chem. Lett. 9:2237) and ortho or para-aminobenzylacetals. Spacers can be used that undergo cyclization upon amide bond hydrolysis, such as substituted and unsubstituted 4-aminobutyric acid amides (see, e.g., Rodrigues et. al., 1995, Chemistry Biology 2:223), appropriately substituted bicyclo [2.2.1] and bicyclo[2.2.2] ring systems (see, e.g., Storm et al., 1972, J. Amer. Chem. Soc. 94:5815) and 2-aminophenylpropionic acid amides (see, e.g., Amsberry et. al., 1990, J. Org. Chem. 55:5867). Elimination of amine-containing drugs that are substituted at the a-position of glycine (see, e.g., Kingsbury et al., 1984, J. Med. Chem. 27:1447) are also examples of self-immolative spacers.

In one embodiment, the Spacer unit is a branched bis (hydroxymethyl)styrene (BHMS) unit as depicted in the following Scheme, which can be used to incorporate and release multiple drugs.

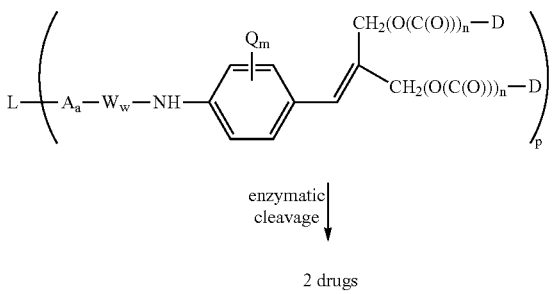

wherein Q is -$C_1$-$C_8$ alkyl, —O—($C_1$-$C_8$ alkyl), -halogen, -nitro or -cyano; m is an integer ranging from 0-4; n is 0 or 1; and p ranges raging from 1 to 20. In one embodiment, the -D moieties are the same. In yet another embodiment, the -D moieties are different.

Other suitable Spacer units are disclosed in Published U.S. Patent Application No. 2005-0238649, the disclosure of which is incorporated by reference herein.

The Ligand Unit

A Ligand unit includes within its scope any molecule that binds or reactively associates or complexes with a receptor, antigen or other receptive moiety associated with a given target-cell or cell population. In one aspect, the Ligand unit acts to deliver a Drug unit (infra) to the particular target cell or cell population with which the Ligand unit reacts. Such Ligand units include, but are not limited to, large molecular weight proteins such as, for example, full-length antibodies, antibody fragments, smaller molecular weight proteins, polypeptides or peptides, lectins, glycoproteins, non-peptides, vitamins, nutrient-transport molecules, and any other cell binding molecule or substance.

Useful non-immunoreactive proteins, polypeptides, or peptide ligands include, but are not limited to, transferrin, epidermal growth factors ("EGF"), bombesin, gastrin, gastrin-releasing peptide, platelet-derived growth factor, IL-2, IL-6, transforming growth factors ("TGF"), such as TGF-α and TGF-β, vaccinia growth factor ("VGF"), insulin and insulin-like growth factors I and II, lectins, somatostatin and apoprotein from low density lipoprotein.

Useful polyclonal antibodies are heterogeneous populations of antibody molecules, such as those derived from the sera of immunized animals. Various procedures known in the art may be used for the production of polyclonal antibodies to an antigen-of-interest. For example, for the production of polyclonal antibodies, various host animals can be immunized by injection with an antigen of interest or derivative thereof, including but not limited to rabbits, mice, rats, and guinea pigs. Various adjuvants can be used to increase the immunological response, depending on the host species, and including but not limited to Freund's (complete and incomplete) adjuvant, mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum. Such adjuvants are also well known in the art.

Useful monoclonal antibodies are homogeneous populations of antibodies to a particular antigenic determinant (e.g., a cell antigen (such as a cancer or autoimmune cell antigen), a viral antigen, a microbial antigen, a protein, a peptide, a carbohydrate, a chemical, a nucleic acid, or antigen-binding fragments thereof. A monoclonal antibody (mAb) to an antigen-of-interest can be prepared by using any technique known in the art. These include, but are not limited to, the hybridoma technique originally described by Köhler and Milstein (1975, Nature 256, 495-497), the human B cell hybridoma technique (Kozbor et al., 1983, Immunology Today 4:72), and the EBV-hybridoma technique (Cole et al., 1985, Monoclonal Antibodies and Cancer Therapy, Alan R. Liss, Inc., pp. 77-96). Such antibodies may be of any immunoglobulin class including IgG, IgM, IgE, IgA, and IgD and any subclass thereof. The hybridoma producing the mAbs of use in this invention may be cultivated in vitro or in vivo.

Useful monoclonal antibodies include, but are not limited to, human monoclonal antibodies, humanized monoclonal antibodies, chimeric monoclonal antibodies and functionally active antibody fragments. Human monoclonal antibodies may be made by any of numerous techniques known in the art (see, e.g., Teng et al., 1983, Proc. Natl. Acad. Sci. USA. 80:7308-7312; Kozbor et al., 1983, Immunology Today 4:72-79; Olsson et al., 1982, Meth. Enzymol. 92:3-16; and U.S. Pat. Nos. 5,939,598 and 5,770,429).

Additionally, recombinant antibodies, such as chimeric and humanized monoclonal antibodies, comprising both human and non-human portions, which can be made using standard recombinant DNA techniques, are useful antibodies. (See, e.g., Cabilly et a., U.S. Pat. No. 4,816,567; and Boss et a., U.S. Pat. No. 4,816,397, which are incorporated herein by reference in their entirety.) Humanized antibodies are antibody molecules from non-human species having one or more complementarity determining regions (CDRs) from the non-human species and a framework region from a human immunoglobulin molecule. (See, e.g., Queen, U.S. Pat. No. 5,585,089, which is incorporated herein by reference in its entirety.) Such chimeric and humanized monoclonal antibodies can be produced by recombinant DNA techniques known in the art, for example using methods described in International Publication No. WO 87/02671; European Patent Publication No. 0 184 187; European Patent Publication No. 0 171 496; European Patent Publication No. 0 173 494; International Publication No. WO 86/01533; U.S. Pat. No. 4,816,567; European Patent Publication No. 012 023; Berter et al, 1988, Science 240:1041-1043; Liu et a., 1987, Proc. Natl. Acad. Sci. USA 84:3439-3443; Liu et al., 1987, J. Immunol. 139:3521-3526; Sun et al., 1987, Proc. Natl. Acad. Sci. USA 84:214-218; Nishimura et al., 1987, Cancer. Res. 47:999-1005; Wood et al., 1985, Nature 314:446-449; Shaw et a., 1988, J. Natl. Cancer Inst. 80:1553-1559; Morrison, 1985, Science 229:1202-1207; Oi et al., 1986, BioTechniques 4:214; U.S. Pat. No. 5,225,539; Jones et a., 1986, Nature 321:552-525; Verhoeyan et a., 1988, Science 239:1534; and Beidler et al., 1988, J. Immunol. 141:4053-4060; each of which is incorporated herein by reference in its entirety.

Completely human antibodies can be produced using transgenic mice that are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see, e.g., Lonberg and Huszar (1995, Int. Rev. Immunol. 13:65-93). For a detailed discussion of this technology for producing human antibodies and human monoclonal antibodies and protocols for producing such antibodies (see, e.g., U.S. Pat. Nos. 5,625,126; 5,633,425; 5,569,825; 5,661,016; and 5,545,806; each of which is incorporated herein by reference in its entirety). Other human antibodies can be obtained commercially from, for example, Abgenix, Inc. (Freemont, Calif.) and Medarex (Sunnyvale, Calif.).

Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope. (see, e.g., Jespers et al., 1994, Biotechnology 12:899-903). Human antibodies also can be produced using various techniques known in the art, including phage display libraries (Hoogenboom and Winter, 1991, J. Mol. Biol. 227: 381; Marks et al., 1991, J. Mol. Biol. 222:581; Quan and Carter, 2002, The rise of monoclonal antibodies as therapeutics, In Anti-IgE and Allergic Disease, Jardieu and Fick Jr., eds., Marcel Dekker, New York, N.Y., Chapter 20, pp. 427-469).

In some embodiments, the antibody is monospecific. The antibody can also be a bispecific antibody. Methods for making bispecific antibodies are known in the art. Traditional production of full-length bispecific antibodies is based on the coexpression of two immunoglobulin heavy chain-light chain pairs, where the two chains have different specificities (see, e.g., Milstein et al., 1983, Nature 305:537-539). Because of the random assortment of immunoglobulin heavy and light chains, these hybridomas (quadromas) produce a potential mixture of 10 different antibody molecules, of which only one has the correct bispecific structure. Similar procedures are disclosed in International Publication No. WO 93/08829, and in Traunecker et al., 1991, EMBO J. 10:3655-3659.

According to a different approach, antibody variable domains with the desired binding specificities (antibody-antigen combining sites) are fused to immunoglobulin constant domain sequences. The fusion typically is with an immunoglobulin heavy chain constant region, comprising at least part of the hinge, $C_H2$, and $C_H3$ domains. It is preferred to have the first heavy-chain constant region ($C_H1$) containing the site necessary for light chain binding, present in at least one of the fusions. Nucleic acids with sequences encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

For example, the bispecific antibodies can have a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation (International Publication No. WO 94/04690; which is incorporated herein by reference in its entirety).

For further details for generating bispecific antibodies see, for example, Suresh et al., 1996, *Methods in Enzymology* 121:210; Rodrigues et al., 1993, *J. Immunology* 151:6954-6961; Carter et al., 1992, *Bio/Technology* 10:163-167; Carter et al., 1995, *J. Hematotherapy* 4:463-470; Merchant et al., 1998, *Nature Biotechnology* 16:677-681. Using such techniques, bispecific antibodies can be prepared for use in the treatment or prevention of disease as defined herein.

Bifunctional antibodies are also described in European Patent Publication No. 0 105 360. As disclosed in this reference, hybrid or bifunctional antibodies can be derived either biologically, e.g., by cell fusion techniques, or chemically, especially with cross-linking agents or disulfide-bridge forming reagents, and may comprise whole antibodies or fragments thereof. Methods for obtaining such hybrid antibodies are disclosed for example, in International Publication WO 83/03679, and European Patent Publication No. 0 217 577, both of which are incorporated herein by reference.

The antibody also can be a functionally active fragment, derivative or analog of an antibody that immunospecifically binds to a desired target antigen (e.g., a cancer cell antigen, a viral antigen, or a microbial antigen) or other antibodies bound to a target cell(s) or matrix. In this regard, "functionally active" means that the fragment, derivative or analog is able to elicit anti-anti-idiotype antibodies that recognize the same antigen that the antibody from which the fragment, derivative or analog is derived recognized. In an exemplary embodiment the antigenicity of the idiotype of the immunoglobulin molecule can be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art (e.g., the BIAcore assay) (see, e.g., Kabat et al., 1991, *Sequences of Proteins of Immunological Interest*, Fifth Edition, National Institute of Health, Bethesda, Md.; Kabat et al., 1980, *J. Immunology* 125(3):961-969).

Other useful antibodies include fragments of antibodies such as, but not limited to, F(ab')$_2$ fragments, Fab' fragments, Fab fragments, Fvs, single chain antibodies (SCAs) (e.g., as described in U.S. Pat. No. 4,946,778; Bird, 1988, *Science* 242:423-42; Huston et al., 1988, *Proc. Natl. Acad. Sci. USA* 85:5879-5883; and Ward et al., 1989, *Nature* 334:544-54), scFv, sc-Fv-Fc, FvdsFv, minibodies, diabodies, triabodies, tetrabodies, and any other molecule comprising CDRs and that have the same specificity as the antibody.

In other embodiments, the antibody is a fusion protein of an antibody, or a functionally active fragment thereof, for example in which the antibody is fused via a covalent bond (e.g., a peptide bond), at either the N-terminus or the C-terminus to an amino acid sequence of another protein (or portion thereof, typically at least a 10, 20 or 50 amino acid portion of the protein) that is not the antibody. In some embodiments, the antibody or fragment thereof can be covalently linked to the other protein at the N-terminus of the constant domain.

Antibodies can also include analogs and derivatives that are either modified, e.g., by the covalent attachment of any type of molecule as long as such covalent attachment permits the antibody to retain its antigen binding immunospecificity. For example, the derivatives and analogs of the antibodies include those that have been further modified, e.g., by glycosylation, acetylation, pegylation, phosphorylation, amidation, derivatization by known protecting/blocking groups, proteolytic cleavage, linkage to a cellular antibody unit or other protein, etc. Any of numerous chemical modifications can be carried out by known techniques, including, but not limited to specific chemical cleavage, acetylation, formylation, metabolic synthesis in the presence of tunicamycin, or the like. Additionally, the analog or derivative can contain one or more unnatural amino acids.

In specific embodiments, it may be desirable to improve the binding affinity and/or other biological properties of the antibody. See, e.g., U.S. Patent Publication Nos. 2006-0003412 and 2006-0008882. Amino acid sequence variants of the antibodies are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid changes also may alter post-translational processes of the antibody, such as changing the number or position of glycosylation sites.

A useful method for identification of certain residues or regions of the antibody that are favored locations for mutagenesis is called "alanine scanning mutagenesis" as described by Cunningham and Wells (1989, *Science* 244:1081-1085). Here, a residue or group of target residues are identified (e.g., charged residues such as arg, asp, his, lys, and glu) and replaced by a neutral or negatively charged amino acid (typically alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis is conducted at the target codon or region and the expressed antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide.

Another type of variant is an amino acid substitution variant. These variants have at least one amino acid residue in the antibody molecule replaced by a different residue. The sites of greatest interest for substitutional mutagenesis include the hypervariable regions, but framework region alterations are also contemplated.

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally-occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gin, his, lys, arg;
(5) residues that influence chain orientation: gly, pro; and
(6) aromatic: trp, tyr, phe.
Non-conservative substitutions will entail exchanging a member of one of these classes for another class.

A particularly type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity). In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and the antigen. Such contact residues and neighboring residues are candidates for substitution according to the techniques elaborated herein. Once such variants are generated, the panel of variants is subjected to screening and antibodies with superior properties in one or more relevant assays may be selected for further development.

It may be desirable to modify the antibody with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See, e.g., Caron et al., 1992, *J. Exp Med.* 176:1191-1195; and Shopes, 1992, *J. Immunol.* 148: 2918-2922. Homodimeric antibodies with enhanced anti-tumor activity may also be prepared using heterobifunctional cross-linkers as described in Wolff et al., 1993, *Cancer Research* 53:2560-2565. Alternatively, an antibody can be engineered which has dual Fc regions and may thereby have enhanced complement lysis and ADCC capabilities. See, e.g., Stevenson et al., 1989, *Anti-Cancer Drug Design* 3:219-230.

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Antibodies may be glycosylated at conserved positions in their constant regions (see, e.g., Jefferis and Lund, 1997, *Chem. Immunol.* 65:111-128; Wright and Morrison, 1997, *TibTECH* 15:26-32). The oligosaccharide side chains of the immunoglobulins affect the protein's function (see, e.g., Boyd et al., 1996, *Mol. Immunol,* 32:1311-1318; Wittwe and Howard, 1990, *Biochem.* 29:4175-4180), and the intramolecular interaction between portions of the glycoprotein which can affect the conformation and presented three-dimensional surface of the glycoprotein (see, e.g., Jefferis and Lund, supra; Wyss and Wagner, 1996, *Current Opin. Biotech.* 7:409-416). Oligosaccharides may also serve to target a given glycoprotein to certain molecules based upon specific recognition structures. For example, it has been reported that in agalactosylated IgG, the oligosaccharide moiety 'flips' out of the inter-$C_H2$ space and terminal N-acetylglucosamine residues become available to bind mannose binding protein (see, e.g., Malhotra et al., 1995, *Nature Med.* 1:237-243). Removal by glycopeptidase of the oligosaccharides from CAMPATH-1H (a recombinant humanized murine monoclonal IgG1 antibody which recognizes the CDw52 antigen of human lymphocytes) produced in Chinese Hamster Ovary (CHO) cells resulted in a complete reduction in complement mediated lysis (CMCL) (Boyd et al., 1996, *Mol. Immunol.* 32:1311-1318), while selective removal of sialic acid residues using neuraminidase resulted in no loss of CMCL. Glycosylation of antibodies has also been reported to affect antibody-dependent cellular cytotoxicity (ADCC). In particular, CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (see, e.g., Umana et al., 1999, *Mature Biotech.* 17:176-180).

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Glycosylation variants of antibodies are variants in which the glycosylation pattern of an antibody is altered. By altering is meant deleting one or more carbohydrate moieties found in the antibody, adding one or more carbohydrate moieties to the antibody, changing the composition of glycosylation (glycosylation pattern), the extent of glycosylation, or the like.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites). Similarly, removal of glycosylation sites can be accomplished by amino acid alteration within the native glycosylation sites of the antibody.

The amino acid sequence is usually altered by altering the underlying nucleic acid sequence. These methods include, but are not limited to, isolation from a natural source (in the case of naturally-occurring amino acid sequence variants) or preparation by oligonucleotide-mediated (or site-directed) mutagenesis, PCR mutagenesis, and cassette mutagenesis of an earlier prepared variant or a non-variant version of the antibody.

The glycosylation (including glycosylation pattern) of antibodies may also be altered without altering the amino acid sequence or the underlying nucleotide sequence. Glycosylation largely depends on the host cell used to express the antibody. Since the cell type used for expression of recombinant glycoproteins, e.g., antibodies, as potential therapeutics is rarely the native cell, significant variations in the glycosylation pattern of the antibodies can be expected. See, e.g., Hse et al., 1997, *J. Biol. Chem.* 272:9062-9070. In addition to the choice of host cells, factors which affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (see, e.g., U.S. Pat. Nos. 5,047,335; 5,510,261; and 5,278,299). Glycosylation, or certain types of glycosylation, can be enzymatically removed from the glycoprotein, for example using endoglycosidase H (Endo H). In addition, the recombinant host cell can be genetically engineered, e.g., make defective in processing certain types of polysaccharides. These and similar techniques are well known in the art.

The glycosylation structure of antibodies can be readily analyzed by conventional techniques of carbohydrate analysis, including lectin chromatography, NMR, mass spectrometry, HPLC, GPC, monosaccharide compositional analysis, sequential enzymatic digestion, and HPAEC-PAD, which uses high pH anion exchange chromatography to separate oligosaccharides based on charge. Methods for releasing oligosaccharides for analytical purposes are also known, and include, without limitation, enzymatic treatment (commonly performed using peptide-N-glycosidase F/endo-β-galactosidase), elimination using harsh alkaline environment to release mainly O-linked structures, and chemical methods using anhydrous hydrazine to release both N- and O-linked oligosaccharides.

The antibodies also can have modifications (e.g., substitutions, deletions or additions) in amino acid residues that interact with Fc receptors. In particular, antibodies include antibodies having modifications in amino acid residues identified as involved in the interaction between the anti-Fc domain and the FcRn receptor (see, e.g., International Publication No. WO 97/34631, which is incorporated herein by reference in its entirety).

Antibodies immunospecific for a cancer cell antigen can be obtained commercially, for example, from commercial companies or produced by any method known to one of skill in the art such as, e.g., chemical synthesis or recombinant expression techniques. The nucleotide sequence encoding antibodies immunospecific for a cancer cell antigen can be obtained, e.g., from the GenBank database or a database like it, the literature publications, or by routine cloning and sequencing.

In a specific embodiment, known antibodies for the treatment or prevention of cancer can be used. Antibodies immunospecific for a cancer cell antigen can be obtained commercially or produced by any method known to one of skill in the art such as, erg., recombinant expression techniques. The nucleotide sequence encoding antibodies immunospecific for a cancer cell antigen can be obtained, e.g., from the GenBank database or a database like it, the literature publications, or by routine cloning and sequencing.

Virtually any target protein can be targeted by an antibody, including any target protein which expression is correlated with expression on cells of a cancer, cell proliferative disorder or tumor. In some embodiments, the antigen is a tumor-associated antigen, such as a polypeptide, protein or other molecule that is specifically expressed on the surface of one or more particular type(s) of cancer cell as compared to on one or more normal non-cancerous cell(s). Often, such tumor-associated antigens are more abundantly expressed on the surface of the cancer cells as compared to on the surface of the non-cancerous cells. The identification of such tumor-associated cell surface antigens has given rise to the ability to specifically target cancer cells for destruction via antibody-based therapies.

Suitable target proteins include human tumor antigens recognized by T cells (Robbins and Kawakami, 1996, *Curr. Opin. Immunol* 8:628-636, incorporated herein by reference in its entirety), melanocyte lineage proteins, including gp100, MART-1/MelanA, TRP-1 (gp75), tyrosinase; Tumor-specific widely shared antigens, MAGE-1, MAGE-3, BAGE, GAGE-1, GAGE-1, N-acetylglucosaminyltransferase-V, p15; Tumor-specific mutated antigens, beta-catenin, MUM-1, CDK4; Nonmelanoma antigens for breast, ovarian, cervical and pancreatic carcinoma, HER-2/neu, human papillomavirus-E6, -E7, MUC-1; cancer antigens, such as KS 1/4 pan-carcinoma antigen (Perez and Walker, 1990, *J. Immunol.* 142:3662-3667; Bumal, 1988, *Hybridoma* 7(4):407-415); ovarian carcinoma antigen (CA125) (Yu et al., 1991, *Cancer Res,* 51(2):468-475); prostatic acid phosphate (Tailor et al., 1990, *Nucl. Acids Res.* 18(16):4928); prostate specific antigen (Henttu and Vihko, 1989, *Biochem. Biophys. Res. Comm.* 160(2):903-910; Israeli et al., 1993, *Cancer Res.* 53:227-230); melanoma-associated antigen p97 (Estin et al., 1989, *J. Natl. Cancer Instit.* 81(6):445-446); melanoma antigen gp75 (Vijayasardahl et al., 1990, *J. Exp. Med.* 171(4):1375-1380); high molecular weight melanoma antigen (HMW-MM) (Natali et al., 1987, *Cancer* 59:55-63; Mittelman et al., 1990, *J. Clin. Invest* 86:2136-2144); prostate specific membrane antigen; carcinoembryonic antigen (CEA) (Foon et al., 1994, *Proc. Am. Soc. Clin. Oncol.* 13:294); polymorphic epithelial mucin antigen; human milk fat globule antigen; a colorectal tumor-associated antigen, such as CEA, TAG-72 (Yokata et al., 1992, *Cancer Res.* 52:3402-3408), CO 17-1A (Ragnhammar et al., 1993, *Int. J. Cancer* 53:751-758); GICA 19-9 (Herlyn et al., 1982, *J. Clin. Immunol* 2:135), CTA-1 and LEA; Burkitt's lymphoma antigen-38.13; CD19 (Ghetie et al., 1994, *Blood* 83:1329-1336); human B-lymphoma antigen-CD20 (Reff et al., 1994, *Blood* 83:435-445); CD33 (Sgouros et al., 1993, *J. Nucl. Med.* 34:422-430); melanoma specific antigens such as ganglioside GD2 (Saleh et al., 1993, *J. Immunol.* 151, 3390-3398), ganglioside GD3 (Shitara et al., 1993, *Cancer Immunol. Immunother.* 36:373-380), ganglioside GM2 (Livingston et al., 1994, *J. Clin. Oncol.* 12:1036-1044), ganglioside GM3 (Hoon et al., 1993, *Cancer Res.* 53:5244-5250); tumor-specific transplantation type of cell-surface antigen (TSTA) such as virally-induced tumor antigens including T-antigen DNA tumor viruses and envelope antigens of RNA tumor viruses; oncofetal antigen-alpha-fetoprotein such as CEA of colon, bladder tumor oncofetal antigen (Hellstrom et al., 1985, *Cancer. Res.* 45:2210-2188); differentiation antigen such as human lung carcinoma antigen L6, L20 (Hellstrom et al., 1986, *Cancer Res.* 46:3917-3923); antigens of fibrosarcoma, human leukemia T cell antigen-Gp37 (Bhattacharya-Chatterjee et al., 1988, *J. Immunol.* 141: 1398-1403); neoglycoprotein, sphingolipids, breast cancer antigen such as EGFR (Epidermal growth factor receptor), HER2 antigen (p185HER2), polymorphic epithelial mucin (PEM) (Hilkens et al., 1992, *Trends in Bio. Chem. Sci.* 17:359); malignant human lymphocyte antigen-APO-1 (Bernhard et al., 1989, *Science* 245:301-304); differentiation antigen (Feizi, 1985, *Nature* 314:53-57) such as I antigen found in fetal erythrocytes, primary endoderm, I antigen found in adult erythrocytes and preimplantation embryos, I(Ma) found in gastric adenocarcinomas, M18, M39 found in breast epithelium, SSEA-1 found in myeloid cells, VEP8, VEP9, Myl, VIM-D5, D156-22 found in colorectal cancer, TRA-1-85 (blood group H), C14 found in colonic adenocarcinoma, F3 found in lung adenocarcinoma, AH6 found in gastric cancer, Y hapten, Ley found in embryonal carcinoma cells, TL5 (blood group A), EGF receptor found in A431 cells, E1 series (blood group B) found in pancreatic cancer, FC10.2 found in embryonal carcinoma cells, gastric adenocarcinoma antigen, CO-514 (blood group Lea) found in Adenocarcinoma, NS-10 found in adenocarcinomas, CO-43 (blood group Leb), G49 found in EGF receptor of A431 cells, MH2 (blood group ALeb/Ley) found in colonic adenocarcinoma, 19.9 found in colon cancer, gastric cancer mucins, T5A7 found in myeloid cells, R24 found in melanoma, 4.2, GD3, D1.1, OFA-1, GM2, OFA-2, GD2, and M1:22:25:8 found in embryonal carcinoma cells, and SSEA-3 and SSEA-4.

In some embodiments, the antibody is useful for the treatment of cancer. Examples of antibodies available for the treatment of cancer include, but are not limited to R ITUXAN® (rituximab; Genentech) which is a chimeric anti-CD20 monoclonal antibody for the treatment of patients with non-Hodgkin's lymphoma; OVAREX (AltaRex Corporation, Mass.) which is a murine antibody for the treatment of ovarian cancer; PANOREX (Glaxo Wellcome, NC) which is a murine IgG$_{2a}$ antibody for the treatment of colorectal cancer; CETUXIMAB ERBITUX (Imclone Systems Inc., NY) which is an anti-EGFR IgG chimeric antibody for the treatment of epidermal growth factor positive cancers, such as head and neck cancer; VITAXIN (Medimmune, Inc., MD) which is a humanized antibody for the treatment of sarcoma; CAMPATH I/H (Leukosite, Mass.) which is a humanized IgG$_1$ antibody for the treatment of chronic lymphocytic leukemia (CLL); Smart M195 (Protein Design Labs, Inc., CA) which is a humanized anti-CD33 IgG antibody for the treatment of acute myeloid leukemia (AML); LYMPHOCIDE (Immunomedics, Inc., NJ) which is a humanized anti-CD22 IgG antibody for the treatment of non-Hodgkin's lymphoma; Smart ID10 (Protein Design Labs, Inc., CA) which is a humanized anti-HLA-DR antibody for the treatment of non-Hodgkin's lymphoma; Oncolym (Techniclone, Inc., CA) which is a radiolabeled murine anti-HLA-Dr10 antibody for the treatment of non-Hodgkin's lymphoma; ALLOMUNE (BioTransplant, CA) which is a humanized anti-CD2 mAb for the treatment of Hodgkin's Disease or non-Hodgkin's lymphoma; AVASTIN (Genentech, Inc., CA) which is an anti-VEGF humanized antibody for the treatment of lung and colorectal cancers; Epratuzamab (Immunomedics, Inc., NJ and Amgen, CA) which is an anti-CD22 antibody for the treatment of non-Hodgkin's lymphoma; and CEAcide (Immunomedics, NJ) which is a humanized anti-CEA antibody for the treatment of colorectal cancer.

In some embodiments, the antibody is an antibody against the following antigens (where exemplary cancers are indicated in parentheses): CA125 (ovarian), CA15-3 (carcinomas), CA19-9 (carcinomas), L6 (carcinomas), Lewis Y (carcinomas), Lewis X (carcinomas), alpha fetoprotein (carcinomas), CA 242 (colorectal), placental alkaline phosphatase (carcinomas), prostate specific membrane antigen (prostate), EphB2, TMEFF2, prostatic acid phosphatase (prostate), epidermal growth factor (carcinomas), MAGE-1 (carcinomas), MAGE-2 (carcinomas), MAGE-3 (carcinomas), MAGE-4 (carcinomas), anti-transferrin receptor (carcinomas), p97 (melanoma), MUC1-KLH (breast cancer), CEA (colorectal), gp100 (melanoma), MART1 (melanoma), prostate specific antigen (prostate), IL-2 receptor (T-cell leukemia and lymphomas), CD20 (non-Hodgkin's lymphoma), CD52 (leukemia), CD33 (leukemia), CD22 (lymphoma), human chorionic gonadotropin (carcinoma), CD38 (multiple myeloma), CD40 (lymphoma), mucin (carcinomas), P21 (carcinomas), MPG (melanoma), and Neu oncogene product (carcinomas). Some specific, useful antibodies include, but are not limited to, BR96 mAb (Trail et. al., 1993, *Science* 261:212-215), BR64 (Trail et al., 1997, *Cancer Research* 57:100-105), mAbs against the CD40 antigen, such as S2C6 mAb (Francisco et al., 2000, *Cancer Res.* 60:3225-3231) or other anti-CD40 antibodies, such as those disclosed in U.S Patent Publication Nos. 2003-0211100 and 2002-0142358; mAbs against the CD70 antigen, such as 1F6 mAb and 2F2 mAb, and mAbs against the CD30 antigen, such as AC10 (Bowen et al., 1993, *J. Immunol.* 151:5896-5906; Wahl et al., 2002, *Cancer Res.* 62(13):3736-42) or MDX-0060 (U.S. Patent Publication No. 2004-0006215). Other internalizing antibodies that bind to tumor associated antigens can be used and have been reviewed (Franke et al., 2000, *Cancer Biother. Radiopharm.* 15:459 76; Murray, 2000, *Semin. Oncol.* 27:64 70; Breitling, F., and Dubel, S., Recombinant Antibodies, John Wiley, and Sons, New York, 1998).

In another specific embodiment, known antibodies for the treatment or prevention of an autoimmune disease are used. Antibodies immunospecific for an antigen of a cell that is responsible for producing autoimmune antibodies can be obtained from any organization (e.g., a university scientist or a company) or produced by any method known to one of skill in the art such as, e.g., chemical synthesis or recombinant expression techniques.

Useful antibodies are immunospecific for the treatment of autoimmune diseases include, but are not limited to, anti-nuclear antibody; anti-ds DNA antibody; anti-ss DNA antibody; anti-cardiolipin antibody IgM, IgG; anti-phospholipid antibody IgM, IgG; anti-SM antibody; anti-mitochondrial antibody; anti-thyroid antibody; anti-microsomal antibody; anti-thyroglobulin antibody; anti-SCL-70 antibody; anti-Jo antibody; anti-U$_1$RNP antibody; anti-La/SSB antibody; anti-SSA antibody; anti-SSB antibody; anti-perital cells antibody; anti-histone antibody; anti-RNP antibody; anti-C-ANCA antibody; anti-P-ANCA antibody; anti-centromere antibody; anti-Fibrillarin antibody, and anti-GBM antibody.

In certain embodiments, useful antibodies can bind to a receptor or a receptor complex expressed on a target cell. The receptor or receptor complex can comprise an immunoglobulin gene superfamily member, a TNF receptor superfamily member, an integrin, a cytokine receptor, a chemokine receptor, a major histocompatibility protein, a lectin, or a complement control protein. Non-limiting examples of suitable immunoglobulin superfamily members are CD2, CD3, CD4, CD8, CD19, CD22, CD28, CD79, CD90, CD152/CTLA-4, PD-1, and ICOS. Non-limiting examples of suitable TNF receptor superfamily members are CD27, CD40, CD95/Fas, CD134/OX40, CD137/4-1BB, TNF-R1, TNFR-2, RANK, TACI, BCMA, osteoprotegerin, Apo2/TRAIL-R1, TRAIL-R2, TRAIL-R3, TRAIL-R4, and APO-3. Non-limiting examples of suitable integrins are CD11a, CD11b, CD11c, CD18, CD29, CD41, CD49a, CD49b, CD49c, CD49d, CD49e, CD49f, CD103, and CD104. Non-limiting examples of suitable lectins are C-type, S-type, and I-type lectin.

In an embodiment, the ligand binds to an activated lymphocyte that is associated with an autoimmune disease.

In another specific embodiment, useful ligands immunospecific for a viral or a microbial antigen are monoclonal antibodies. As used herein, the term "viral antigen" includes, but is not limited to, any viral peptide, polypeptide protein (e.g., HIV gp120, HIV nef, RSV F glycoprotein, influenza virus neuraminidase, influenza virus hemagglutinin, HTLV tax, herpes simplex virus glycoprotein (e.g., gB, gC, gD, and gE) and hepatitis B surface antigen) that is capable of eliciting an immune response. As used herein, the term "microbial antigen" includes, but is not limited to, any microbial peptide, polypeptide, protein, saccharide, polysaccharide, or lipid molecule (e.g., a bacterial, fungi, pathogenic protozoa, or yeast polypeptide including, e.g., LPS and capsular polysaccharide 5/8) that is capable of eliciting an immune response.

Antibodies immunospecific for a viral or microbial antigen can be obtained commercially or produced by any method known to one of skill in the art such as, e.g., chemical synthesis or recombinant expression techniques. The nucleotide sequence encoding antibodies that are immunospecific for a viral or microbial antigen can be obtained, e.g., from the GenBank database or a database like it, literature publications, or by routine cloning and sequencing.

In a specific embodiment, useful ligands are those that are useful for the treatment or prevention of viral or microbial infection in accordance with the methods disclosed herein. Examples of antibodies available useful for the treatment of viral infection or microbial infection include, but are not limited to, SYNAGIS (Medimmune, Inc., MD) which is a humanized anti-respiratory syncytial virus (RSV) monoclonal antibody useful for the treatment of patients with RSV infection; PRO542 (Progenics) which is a CD4 fusion antibody useful for the treatment of HIV infection; OSTAVIR (Protein Design Labs, Inc., CA) which is a human antibody useful for the treatment of hepatitis B virus; PROTOVIR (Protein Design Labs, Inc., CA) which is a humanized IgG$_1$ antibody useful for the treatment of cytomegalovirus (CMV); and anti-LPS antibodies.

Other antibodies useful in the treatment of infectious diseases include, but are not limited to, antibodies against the antigens from pathogenic strains of bacteria (e.g., *Streptococcus pyogenes, Streptococcus pneumoniae, Neisseria gonorrheae, Neisseria meningitidis, Corynebacterium diphtheriae, Clostridium botulinum, Clostridium perfringens, Clostridium tetani, Hemophilus influenzae, Klebsiella pneumoniae, Klebsiella ozaenas, Klebsiella rhinoscleromotis, Staphylococc aureus, Vibrio colerae, Escherichia coli, Pseudomonas aeruginosa, Campylobacter* (Vibrio) *fetus, Aeromonas hydrophila, Bacillus cereus, Edwardsiella tarda, Yersinia enterocolitica, Yersinia pestis, Yersinia pseudotuberculosis, Shigella dysenteriae, Shigella flexneri, Shigella sonnei, Salmonella typhimurium, Treponema pallidum, Treponema pertenue, Treponema carateneum, Borrelia vincentii, Borrelia burgdofferi, Leptospira icterohemorrhagiae, Mycobacterium tuberculosis, Pneumocystis carinii, Francisella tularensis, Brucella abortus, Brucella suis, Brucella melitensis, Mycoplasma* spp., *Rickettsia prowazeki, Rickettsia tsutsugumushi*, and *Chlamydia* spp.); pathogenic fungi (e.g., *Coccidioides immitis, Aspergillus fumigatus, Candida albicans, Blastomyces dermatitidis, Cryptococcus neoformans, Histoplasma capsulatum*); protozoa (*Entomoeba histolytica, Toxoplasma gondii, Trichomonas tenas, Trichomonas hominis, Trichomonas vaginalis, Tryoanosoma gambiense, Trypanosoma rhodesiense, Trypanosoma cruzi, Leishmania donovani, Leishmania tropica, Leishmania braziliensis, Pneumocystis pneumonia, Plasmodium vivax, Plasmodium falciparum*, or *Plasmodium malaria*); or Helminths (*Enterobius vermicularis, Trichuris trichiura, Ascaris lumbricoides, Trichinella spiralis, Strongyloides stercoralis, Schistosoma japonicum, Schistosoma mansoni, Schistosoma haematobium*, and hookworms).

Other antibodies useful in this invention for treatment of viral disease include, but are not limited to, antibodies against antigens of pathogenic viruses, such as for example: Poxviridae, Herpesviridae, Herpes Simplex virus 1, Herpes Simplex virus 2, Adenoviridae, Papovaviridae, Enteroviridae, Picornaviridae, Parvoviridae, Reoviridae, Retroviridae, influenza viruses, parainfluenza viruses, mumps, measles, respiratory syncytial virus, rubella, Arboviridae, Rhabdoviridae, Arenaviridae, Hepatitis A virus, Hepatitis B virus, Hepatitis C virus, Hepatitis E virus, Non-A/Non-B Hepatitis virus, Rhinoviridae, Coronaviridae, Rotoviridae, and Human Immunodeficiency Virus.

The Drug Unit

The Drug unit can be any cytotoxic, cytostatic or immunomodulatory drug. D is a Drug unit (moiety) having an atom that can form a bond with the Spacer unit when y=1 or 2 or with the Glucuronide moiety when y=0. In some embodiments, the Drug unit D has a nitrogen atom that can form a bond with the Spacer unit. As used herein, the terms "Drug unit" and "Drug moiety" are synonymous and used interchangeably.

Useful classes of cytotoxic or immunomodulatory agents include, for example, antitubulin agents, auristatins, DNA minor groove binders, DNA replication inhibitors, alkylating agents (e.g., platinum complexes such as cis-platin, mono (platinum), bis(platinum) and tri-nuclear platinum complexes and carboplatin), anthracyclines, antibiotics, antifolates, antimetabolites, calmodulin inhibitors, chemotherapy sensitizers, duocarmycins, etoposides, fluorinated pyrimidines, ionophores, lexitropsins, maytansinoids, nitrosoureas, platinols, pore-forming compounds, purine antimetabolites, puromycins, radiation sensitizers, rapamycins, steroids, taxanes, topoisomerase inhibitors, vinca alkaloids, or the like.

Individual cytotoxic or immunomodulatory agents include, for example, an androgen, anthramycin (AMC), asparaginase, 5-azacytidine, azathioprine, bleomycin, busulfan, buthionine sulfoximine, calicheamicin, calicheamicin derivatives, camptothecin, carboplatin, carmustine (BSNU), CC-1065, chlorambucil, cisplatin, colchicine, cyclophosphamide, cytarabine, cytidine arabinoside, cytochalasin B, dacarbazine, dactinomycin (formerly actinomycin), daunorubicin, decarbazine, DM1, DM4, docetaxel, doxorubicin, etoposide, an estrogen, 5-fluordeoxyuridine, 5-fluorouracil, gemcitabine, gramicidin D, hydroxyurea, idarubicin, ifosfamide, irinotecan, lomustine (CCNU), maytansine, mechlorethamine, melphalan, 6-mercaptopurine, methotrexate, mithramycin, mitomycin C, mitoxantrone, nitroimidazole, paclitaxel, palytoxin, plicamycin, procarbizine, rhizoxin, streptozotocin, tenoposide, 6-thioguanine, thioTEPA, topotecan, vinblastine, vincristine, vinorelbine, VP-16 and VM-26.

In some typical embodiments, suitable cytotoxic agents include, for example, DNA minor groove binders (e.g., enediynes and lexitropsins, a CBI compound; see also U.S. Pat. No. 6,130,237), duocarmycins, taxanes (e.g., paclitaxel and docetaxel), puromycins, vinca alkaloids, CC-1065, SN-38, topotecan, morpholino-doxorubicin, rhizoxin, cyanomorpholino-doxorubicin, echinomycin, combretastatin, netropsin, epothilone A and B, estramustine, cryptophycins, cemadotin, maytansinoids, discodermolide, eleutherobin, and mitoxantrone.

In some embodiments, the Drug is an anti-tubulin agent. Examples of anti-tubulin agents include, but are not limited to, taxanes (e.g., Taxol® (paclitaxel), Taxotere® (docetaxel)), T67 (Tularik) and vinca alkyloids (e.g., vincristine, vinblastine, vindesine, and vinorelbine). Other antitubulin agents include, for example, baccatin derivatives, taxane analogs, epothilones (e.g., epothilone A and B), nocodazole, colchicine and colcimid, estramustine, cryptophycins, cemadotin, maytansinoids, combretastatins, discodermolide, and eleutherobin.

In certain embodiments, the cytotoxic agent is a maytansinoid, another group of anti-tubulin agents. For example, in specific embodiments, the maytansinoid can be maytansine or DM-1 (ImmunoGen, Inc.; see also Chari et al., 1992, Cancer Res. 52:127-131).

In some embodiments, the Drug is an auristatin, such as auristatin E or a derivative thereof. For example, the auristatin E derivative can be an ester formed between auristatin E and a keto acid. For example, auristatin E can be reacted with paraacetyl benzoic acid or benzoylvaleric acid to produce AEB and AEVB, respectively. Other typical auristatin derivatives include AFP, MMAF, and MMAE. The synthesis and structure of auristatin derivatives are described in U.S. Patent Application Publication Nos. 2003-0083263, 2005-0238649 and 2005-0009751; International Patent Publication No. WO 04/010957, International Patent Publication No. WO 02/088172, and U.S. Pat. Nos. 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414.

In some embodiments, -D is either formula $D_E$ or $D_F$:

dently selected from H, $C_1$-$C_8$ alkyl and $C_3$-$C_8$ carbocycle and n is selected from 2, 3, 4, 5 and 6;

$R^6$ is selected from H and $C_1$-$C_8$ alkyl;

$R^7$ is selected from H, $C_1$-$C_8$ alkyl, $C_3$-$C_8$ carbocycle, aryl, $X^1$-aryl, $X^1$—($C_3$-$C_8$ carbocycle), $C_3$-$C_8$ heterocycle and $X^1$—($C_3$-$C_8$ heterocycle);

each $R^8$ is independently selected from H, OH, $C_1$-$C_8$ alkyl, $C_3$-$C_8$ carbocycle and O—($C_1$-$C_8$ alkyl);

$R^9$ is selected from H and $C_1$-$C_8$ alkyl;

$R^{10}$ is selected from aryl and $C_3$-$C_8$ heterocycle;

Z is O, S, NH, or $NR^{12}$, wherein $R^{12}$ is $C_1$-$C_8$ alkyl;

$R^{11}$ is selected from H, $C_1$-$C_{20}$ alkyl, aryl, $C_3$-$C_8$ heterocycle, —($R^{13}O)_m$—$R^{14}$, and —($R^{13}O)_m$—$CH(R^{15})_2$;

m is an integer ranging from 1-1000;

$R^{13}$ is $C_2$-$C_8$ alkyl;

$R^{14}$ is H or $C_1$-$C_8$ alkyl;

each occurrence of $R^{15}$ is independently H, COOH, —$(CH_2)_n$—$N(R^{16})_2$, —$(CH_2)_n$—$SO_3H$, or —$(CH_2)_n$—$SO_3$-$C_1$-$C_8$ alkyl;

each occurrence of $R^{16}$ is independently H, $C_1$-$C_8$ alkyl, or —$(CH_2)_n$—COOH;

$R^{18}$ is selected from —$C(R^8)_2$—$C(R^8)_2$-aryl, —$C(R^8)_2$—$C(R^8)_2$—($C_3$-$C_8$ heterocycle), and —$C(R^8)_2$—$C(R^8)_2$—($C_3$-$C_8$ carbocycle);

$X^1$ is C1-C10 alkylene; and n is an integer ranging from 0 to 6.

In one embodiment, $R^3$, $R^4$ and $R^7$ are independently isopropyl or sec-butyl and $R^5$ is —H. In an exemplary embodiment, $R^3$ and $R^4$ are each isopropyl, $R^5$ is H, and $R^7$ is sec-butyl.

In another embodiment, $R^2$ and $R^6$ are each methyl, and $R^9$ is H.

In still another embodiment, each occurrence of $R^8$ is —$OCH_3$.

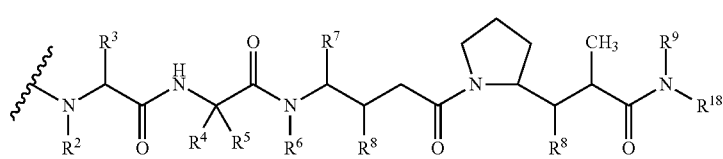

$D_E$

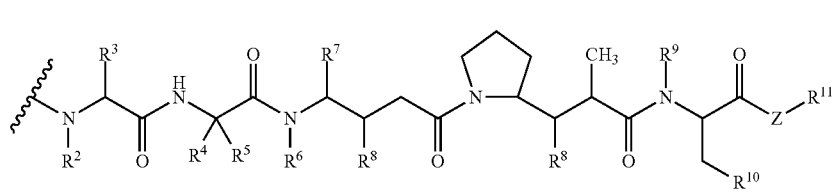

$D_F$ wherein, independently at each location:

$R^2$ is selected from H and $C_1$-$C_8$ alkyl;

$R^3$ is selected from H, $C_1$-$C_8$ alkyl, $C_3$-$C_8$ carbocycle, aryl, $X^1$-aryl, $X^1$—($C_3$-$C_8$ carbocycle), $C_3$-$C_8$ heterocycle and $X^1$-($C_3$-$C_8$ heterocycle);

$R^4$ is selected from H, $C_1$-$C_8$ alkyl, $C_3$-$C_8$ carbocycle, aryl, $X^1$-aryl, $X^1$-($C_3$-$C_8$ carbocycle), $C_3$-$C_8$ heterocycle and $X^1$-($C_3$-$C_8$ heterocycle);

$R^5$ is selected from H and methyl;

or $R^4$ and $R^5$ jointly form a carbocyclic ring and have the formula —$(CR^aR^b)_n$—, wherein $R^a$ and $R^b$ are independently In an exemplary embodiment, $R^3$ and $R^4$ are each isopropyl, $R^2$ and $R^6$ are each methyl, $R^5$ is H, $R^7$ is sec-butyl, each occurrence of $R^8$ is —$OCH_3$, and $R^9$ is H.

In one embodiment, Z is —O— or —NH—.

In one embodiment, $R^{10}$ is aryl.

In an exemplary embodiment, $R^{10}$ is -phenyl.

In an exemplary embodiment, when Z is —O—, $R^{11}$ is H, methyl or t-butyl.

In one embodiment, when Z is —NH, $R^{11}$ is —$CH(R^{15})_2$, wherein $R^{15}$ is —$(CH_2)_n$—$N(R^{16})_2$, and $R^{16}$ is —$C_1$-$C_8$ alkyl or —$(CH_2)_n$—COOH.

In another embodiment, when Z is —NH, $R^{11}$ is —$CH(R^{15})_2$, wherein $R^{15}$ is —$(CH_2)_n$—$SO_3H$.

Illustrative Drug units (-D) include the drug units having the following structures:
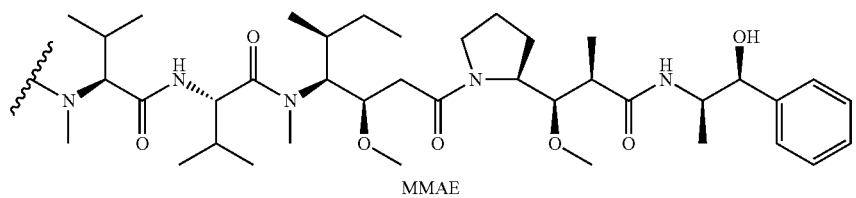
MMAE
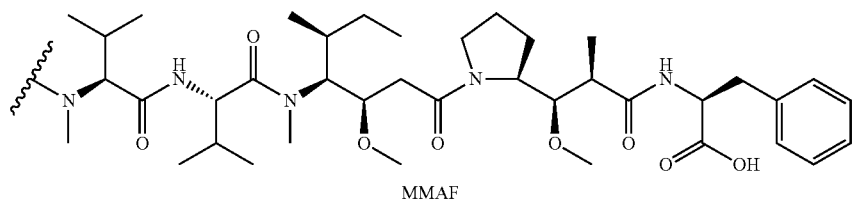
MMAF
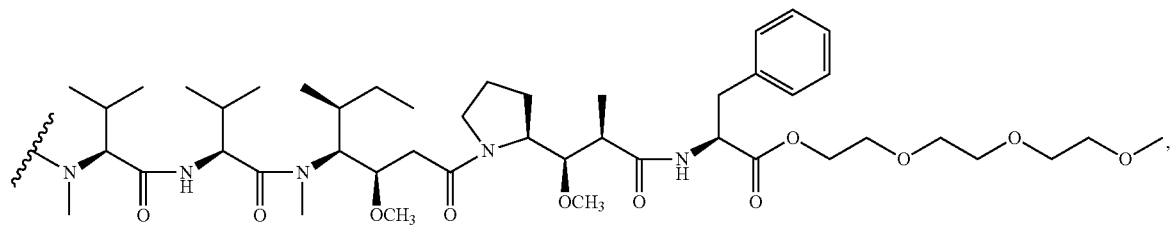
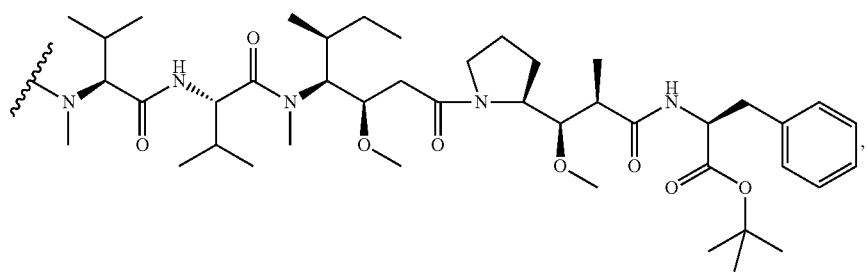
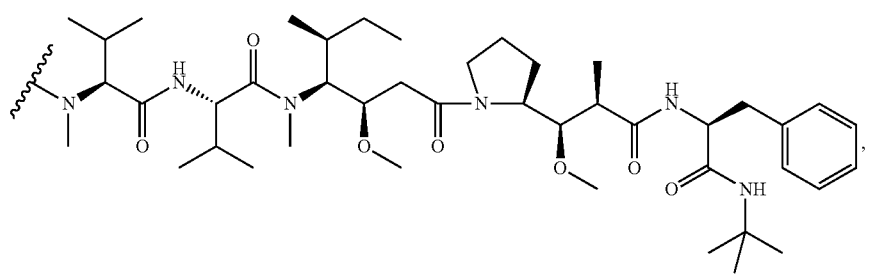
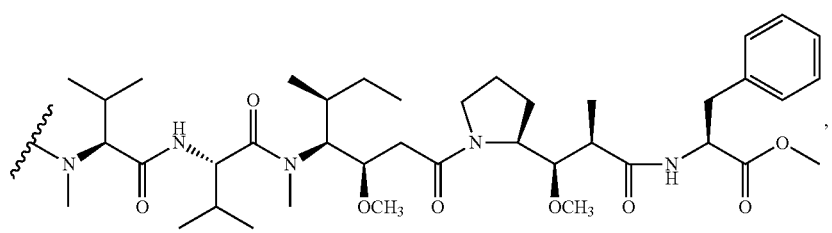

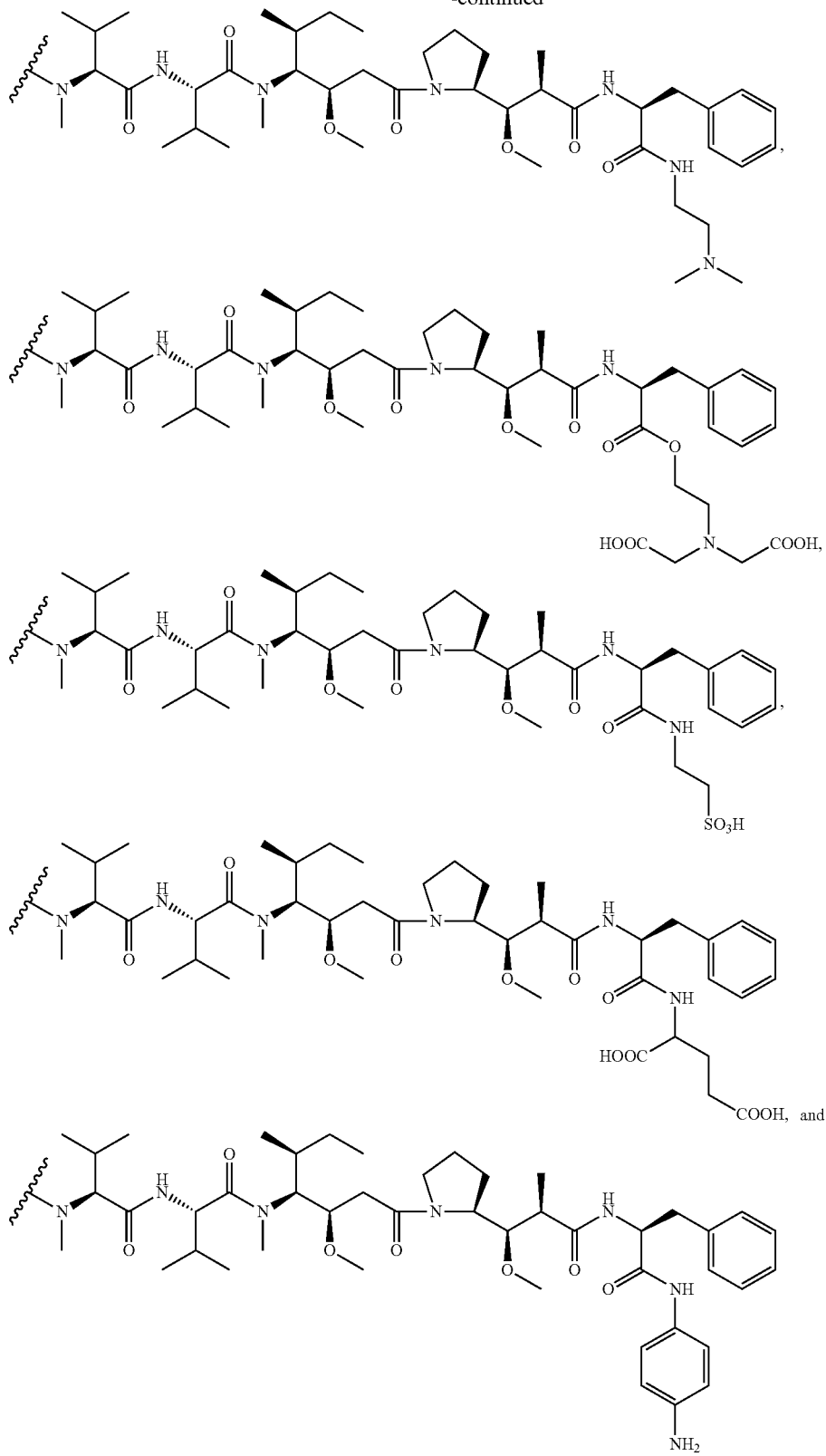
and pharmaceutically acceptable salts or solvates thereof.
In one aspect, hydrophilic groups, such as but not limited to triethylene glycol esters (TEG), as shown above, can be attached to the Drug Unit at $R^{11}$. Without being bound by theory, the hydrophilic groups assist in the internalization and non-agglomeration of the Drug Unit.

In another aspect, the Drug unit is an amino-benzoic acid derivative of an auristatin of the following formula:

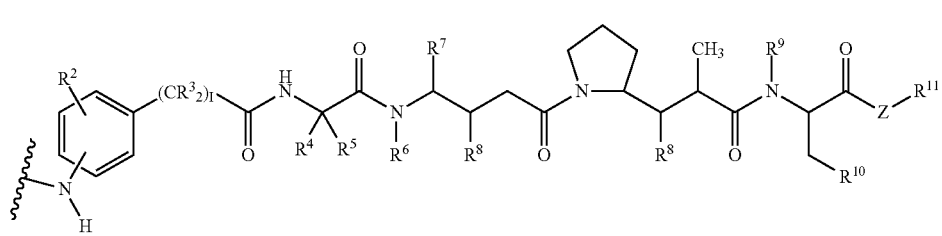

wherein, independently at each location:
$R^2$ is selected from -hydrogen, —$C_1$-$C_8$ alkyl, —O—($C_1$-$C_8$ alkyl), -halogen, —$NO_2$, —COOH, and —C(O)$OR^{11}$;
each $R^3$ is selected independently from -hydrogen and —$C_1$-$C_8$ alkyl;
I is an integer ranging from 0-10;
$R^4$ is selected from -hydrogen, —$C_1$-$C_8$ alkyl, —$C_3$-$C_8$ carbocycle, -aryl, $X^1$-aryl, $X^1$—($C_3$-$C_8$ carbocycle), —$C_3$-$C_8$ heterocycle and $X^1$-($C_3$-$C_8$ heterocycle), and $R^5$ is selected from —H and -methyl; or $R^4$ and $R^5$ jointly have the formula —$(CR^aR^b)_n$—, wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the carbon atom to which they are attached;
$R^6$ is selected from —H and —$C_1$-$C_8$ alkyl;
$R^7$ is selected from -H, —$C_1$-$C_8$ alkyl, —$C_3$-$C_8$ carbocycle, aryl, $X^1$-aryl, $X^1$—($C_3$-$C_8$ carbocycle), —$C_3$-$C_8$ heterocycle and $X^1$-($C_3$-$C_8$ heterocycle);
each $R^8$ is independently selected from —H, —OH, —$C_1$-$C_8$ alkyl, —$C_3$-$C_8$ carbocycle, —O-alkyl-($C_1$-$C_8$ carbocycle) and —O—($C_1$-$C_8$ alkyl);
$R^9$ is selected from —H and —$C_1$-$C_8$ alkyl;
$R^{10}$ is selected from aryl and —$C_3$-$C_8$ heterocycle;
Z is —O—, —S—, —NH—, or —$NR^{12}$— where $R^{12}$ is $C_1$-$C_8$ alkyl or aryl;
$R^{11}$ is selected from —H, $C_1$-$C_8$ alkyl, aryl, —$C_3$-$C_8$ heterocycle, —$(CH_2CH_2O)_r$—H, —$(CH_2CH_2O)_r$—$CH_3$, and —$(CH_2CH_2O)_r$—$CH_2CH_2C(O)OH$; wherein r is an integer ranging from 1-10; and
$X^1$ is $C_1$-$C_{10}$ alkylene.
In some embodiments, the Drug unit is of the following formula:

wherein, independently at each location:
$R^4$ is selected from -hydrogen, —$C_1$-$C_8$ alkyl, —$C_3$-$C_8$ carbocycle, -aryl, $X^1$-aryl, $X^1$—($C_3$-$C_8$ carbocycle), —$C_3$-$C_8$ heterocycle and $X^1$—($C_3$-$C_8$ heterocycle), and $R^5$ is selected from —H and -methyl; or $R^4$ and $R^5$ jointly have the formula —$(CR^aR^b)_n$—, wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the carbon atom to which they are attached;
$R^6$ is selected from —H and —$C_1$-$C_8$ alkyl;
$R^7$ is selected from —H, —$C_1$-$C_8$ alkyl, —$C_3$-$C_8$ carbocycle, aryl, $X^1$-aryl, $X^1$—($C_3$-$C_8$ carbocycle), —$C_3$-$C_8$ heterocycle and $X^1$-($C_3$-$C_8$ heterocycle);
each $R^8$ is independently selected from —H, —OH, —$C_1$-$C_8$ alkyl, —$C_3$-$C_8$ carbocycle, —O-alkyl-($C_1$-$C_8$ carbocycle) and —O—($C_1$-$C_8$ alkyl);
$R^9$ is selected from —H and —$C_1$-$C_8$ alkyl;
$R^{10}$ is selected from aryl and —$C_3$-$C_8$ heterocycle;
Z is —O—, —S—, —NH—, or —$NR^{12}$— where $R^{12}$ is $C_1$-$C_8$ alkyl or aryl;
$R^{11}$ is selected from —H, $C_1$-$C_8$ alkyl, aryl, —$C_3$-$C_8$ heterocycle, —$(CH_2CH_2O)_r$—H, —$(CH_2CH_2O)_r$—$CH_3$, and —$(CH_2CH_2O)_r$—$CH_2CH_2C(O)OH$; wherein r is an integer ranging from 1-10; and
$X^1$ is $C_1$-$C_{10}$ alkylene.

I

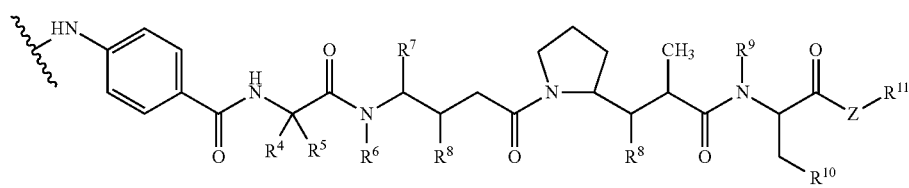

In some embodiments, the Drug unit is of the following formula:

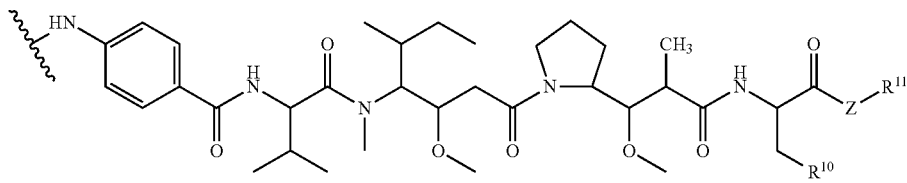

wherein, independently at each location:
$R^{10}$ is selected from aryl group and —$C_3$-$C_8$ heterocycle;
Z is —O—, —S—, —NH—, or —$NR^{12}$— where $R^{12}$ is $C_1$-$C_8$ alkyl or aryl; and
$R^{11}$ is selected from —H, $C_1$-$C_8$ alkyl, aryl, —$C_3$-$C_8$ heterocycle, —$(CH_2CH_2O)_r$—H, —$(CH_2CH_2O)_r$—$CH_3$, and —$(CH_2CH_2O)_r$$CH_2CH_2C(O)OH$; wherein r is an integer ranging from 1-10.

In some embodiments, the Drug unit is of the following formula:

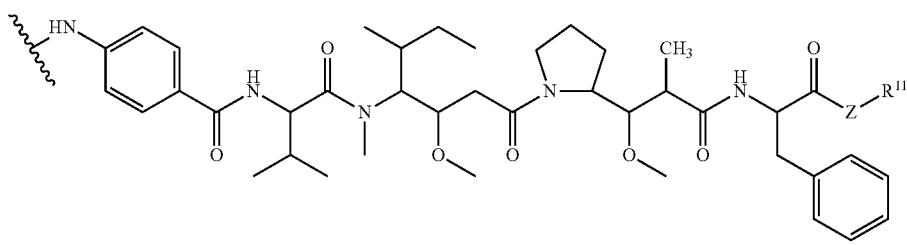

wherein:
Z is —O—, —S—, —NH—, or —$NR^{12}$— where $R^{12}$ is $C_1$-$C_8$ alkyl or aryl; and
$R^{11}$ is selected from —H, $C_1$-$C_8$ alkyl, aryl, —$C_3$-$C_8$ heterocycle, —$(CH_2CH_2O)_r$—H, —$(CH_2CH_2O)_r$—$CH_3$, and —$(CH_2CH_2O)_r$—$CH_2CH_2C(O)OH$; wherein r is an integer ranging from 1-10.

In some embodiments, the Drug unit is of the following formula:

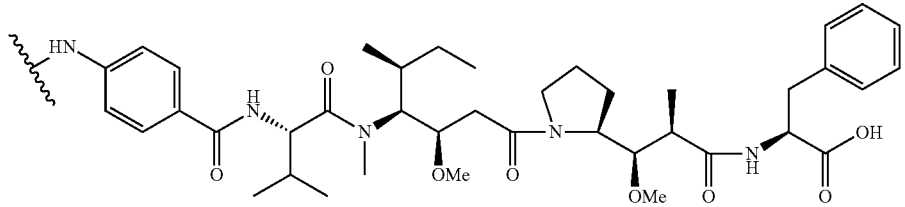

In some embodiments, the Drug unit is not a radioisotope. In some embodiments, the Drug unit is not radioactive.

In some embodiments, the Drug unit is an antimetabolite. The antimetabolite can be, for example, a purine antagonist (e.g., azothioprine or mycophenolate mofetil), a dihydrofolate reductase inhibitor (e.g., methotrexate), acyclovir, gangcyclovir, zidovudine, vidarabine, ribavarin, azidothymidine, cytidine arabinoside, amantadine, dideoxyuridine, iododeoxyuridine, poscarnet, or trifluridine.

In other embodiments, the Drug unit is tacrolimus, cyclosporine, FU506 or rapamycin. In further embodiments, the Drug is aldesleukin, alemtuzumab, alitretinoin, allopurinol, altretamine, amifostine, anastrozole, arsenic trioxide, bexarotene, bexarotene, calusterone, capecitabine, celecoxib, cladribine, Darbepoetin alfa, Denileukin diftitox, dexrazoxane, dromostanolone propionate, epirubicin, Epoetin alfa, estramustine, exemestane, Filgrastim, floxuridine, fludarabine, fulvestrant, gemcitabine, gemtuzumab ozogamicin (MYLOTARG), goserelin, idarubicin, ifosfamide, imatinib mesylate, Interferon alfa-2a, irinotecan, letrozole, leucovorin, levamisole, meclorethamine or nitrogen mustard, megestrol, mesna, methotrexate, methoxsalen, mitomycin C, mitotane, nandrolone phenpropionate, oprelvekin, oxaliplatin, pamidronate, pegademase, pegaspargase, pegfilgrastim, pentostatin, pipobroman, plicamycin, porfimer sodium, procarbazine, quinacrine, rasburicase, Rituximab, Sargramostim, streptozocin, tamoxifen, temozolomide, teniposide, testolactone, thioguanine, toremifene, Tositumomab, Trastuzumab (HERCEPTIN), tretinoin, uracil mustard, valrubicin, vinblastine, vincristine, vinorelbine or zoledronate.

In some embodiments, the Drug moiety is an immunomodulatory agent. The immunomodulatory agent can be, for example, gangcyclovir, etanercept, tacrolimus, cyclosporine, rapamycin, cyclophosphamide, azathioprine, mycophenolate mofetil or methotrexate. Alternatively, the immunomodulatory agent can be, for example, a glucocorticoid (e.g., cortisol or aldosterone) or a glucocorticoid analogue (e.g., prednisone or dexamethasone).

In some embodiments, the immunomodulatory agent is an anti-inflammatory agent, such as arylcarboxylic derivatives, pyrazole-containing derivatives, oxicam derivatives and nicotinic acid derivatives. Classes of anti-inflammatory agents include, for example, cyclooxygenase inhibitors, 5-lipoxygenase inhibitors, and leukotriene receptor antagonists.

Suitable cyclooxygenase inhibitors include meclofenamic acid, mefenamic acid, carprofen, diclofenac, diflunisal, fenbufen, fenoprofen, indomethacin, ketoprofen, nabumetone, sulindac, tenoxicam and tolmetin.

Suitable lipoxygenase inhibitors include redox inhibitors (e.g., catechol butane derivatives, nordihydroguaiaretic acid (NDGA), masoprocol, phenidone, lanopalen, indazolinones, naphazatrom, benzofuranol, alkylhydroxylamine), and non-redox inhibitors (e.g., hydroxythiazoles, methoxyalkylthiazoles, benzopyrans and derivatives thereof, methoxytetrahydropyran, boswellic acids and acetylated derivatives of boswellic acids, and quinolinemethoxyphenylacetic acids substituted with cycloalkyl radicals), and precursors of redox inhibitors.

Other suitable lipoxygenase inhibitors include antioxidants (e.g., phenols, propyl gallate, flavonoids and/or naturally occurring substrates containing flavonoids, hydroxylated derivatives of the flavones, flavonol, dihydroquercetin, luteolin, galangin, orobol, derivatives of chalcone, 4,2',4'-trihydroxychalcone, ortho-aminophenols, N-hydroxyureas, benzofuranols, ebselen and species that increase the activity of the reducing selenoenzymes), iron chelating agents (e.g., hydroxamic acids and derivatives thereof, N-hydroxyureas, 2-benzyl-1-naphthol, catechols, hydroxylamines, carnosol trolox C, catechol, naphthol, sulfasalazine, zyleuton, 5-hydroxyanthranilic acid and 4-(omega-arylalkyl)phenylalkanoic acids), imidazole-containing compounds (e.g., ketoconazole and itraconazole), phenothiazines, and benzopyran derivatives.

Yet other suitable lipoxygenase inhibitors include inhibitors of eicosanoids (e.g., octadecatetraenoic, eicosatetraenoic, docosapentaenoic, eicosahexaenoic and docosahexaenoic acids and esters thereof, PGE1 (prostaglandin E1), PGA2 (prostaglandin A2), viprostol, 15-monohydroxyeicosatetraenoic, 15-monohydroxy-eicosatrienoic and 15-monohydroxyeicosapentaenoic acids, and leukotrienes B5, C5 and D5), compounds interfering with calcium flows, phenothiazines, diphenylbutylamines, verapamil, fuscoside, curcumin, chlorogenic acid, caffeic acid, 5,8,11,14-eicosatetrayenoic acid (ETYA), hydroxyphenylretinamide, lonapalen, esculin, diethylcarbamazine, phenantroline, baicalein, proxicromil, thioethers, diallyl sulfide and di-(1-propenyl) sulfide.

Leukotriene receptor antagonists include calcitriol, ontazolast, Bayer Bay-x-1005, Ciba-Geigy CGS-25019C, ebselen, Leo Denmark ETH-615, Lilly LY-293111, Ono ONO-4057, Terumo TMK-688, Boehringer Ingleheim BI-RM-270, Lilly LY 213024, Lilly LY 264086, Lilly LY 292728, Ono ONO LB457, Pfizer 105696, Perdue Frederick PF 10042, Rhone-Poulenc Rorer RP 66153, SmithKline Beecham SB-201146, SmithKline Beecham SB-201993, SmithKline Beecham SB-209247, Searle SC-53228, Sumitamo SM 15178, American Home Products WAY 121006, Bayer Bay-o-8276, Warner-Lambert CI-987, Warner-Lambert CI-987BPC-15LY 223982, Lilly LY 233569, Lilly LY-255283, MacroNex MNX-160, Merck and Co. MK-591, Merck and Co. MK-886, Ono ONO-LB-448, Purdue Frederick PF-5901, Rhone-Poulenc Rorer RG 14893, Rhone-Poulenc Rorer RP 66364, Rhone-Poulenc Rorer RP 69698, Shionoogi S-2474, Searle SC-41930, Searle SC-50505, Searle SC-51146, Searle SC-52798, SmithKline Beecham SK&F-104493, Leo Denmark SR-2566, Tanabe T-757 and Teijin TEI-1338.

Synthesis of the Ligand Drug Units

A Glucuronide unit and glucuronide-based Linker-Drug conjugate can be synthesized by any suitable technique. The synthesis of Glucuronide-based prodrugs is disclosed in, for example, Desbene et al., 1998, *Anticancer Drug Des.* 13:955-68.

A Ligand Drug compound conjugate comprising a glucuronide-based Linker-Drug conjugate can be synthesized by techniques in the art. For example, a glucuronide-based Linker-Drug conjugate can comprise an acetamide functionality for conjugation to a Ligand unit. Referring to Scheme 1, a β-glucuronide prodrug of doxorubicin (3) is shown in Scheme 1. The amide can be modified, via the amine precursor, to possess a reactive group such as a bromoacetamide or maleimide for attachment to a Ligand, such as an antibody. Further, as disclosed in Scheme 1, under the action of β-glucuronidase, the β-glucuronidase-labile drug linker system would result in glycosidic bond cleavage followed by 1,6-elimination and loss of carbon dioxide, to liberate drug from the Ligand Drug Conjugate.

In other exemplary embodiments, Scheme 2 discloses exemplary antibody drug conjugates of MMAE, and MMAF and another potent doxorubicin derivative; doxorubicin propyl oxazoline (DPO; 2) which is a precursor to 2-pyrrolino-doxorubicin (4) as shown in Scheme 2. Additionally, shown in Scheme 2a is a β-glucuronide prodrug of MMAE.

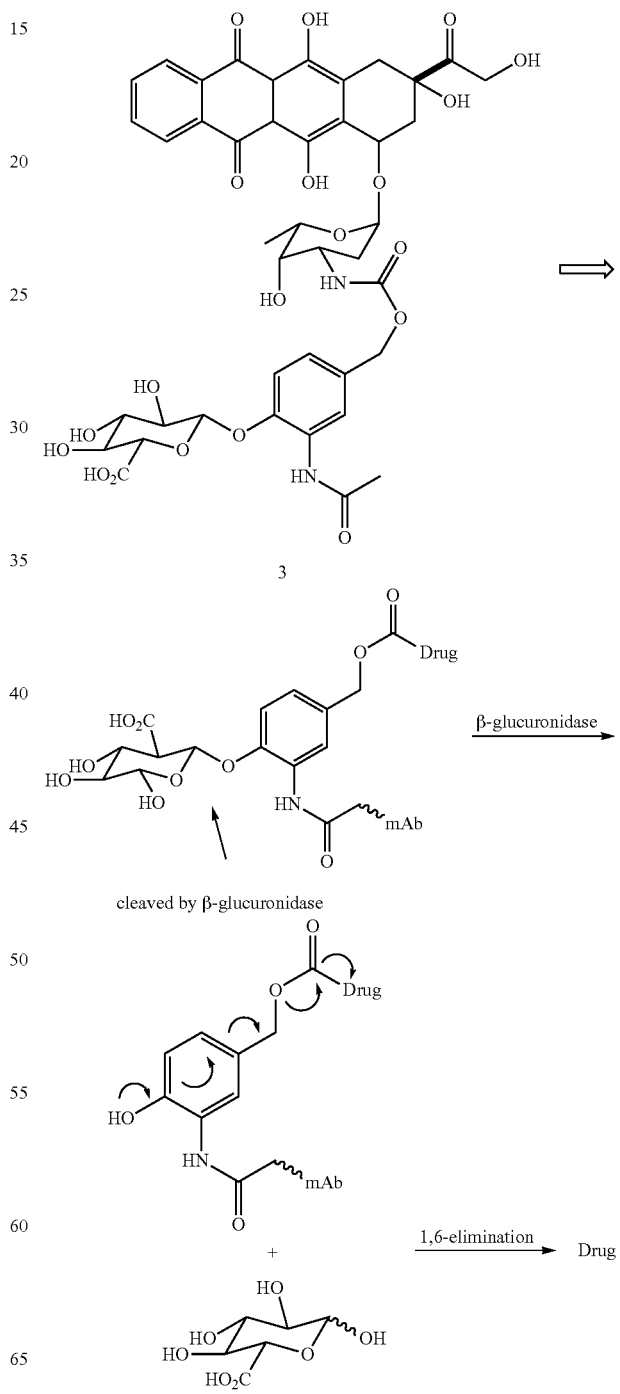

Scheme 1.

Scheme 2.
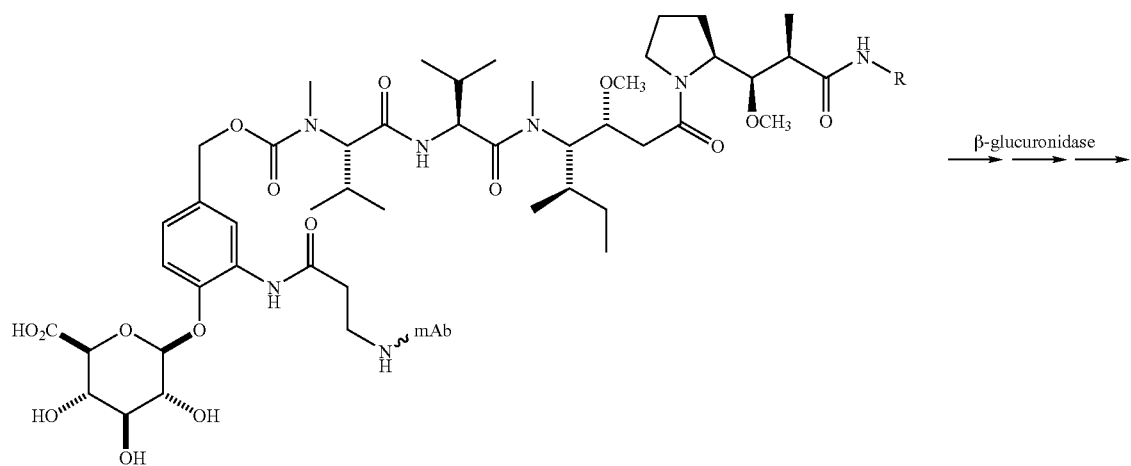
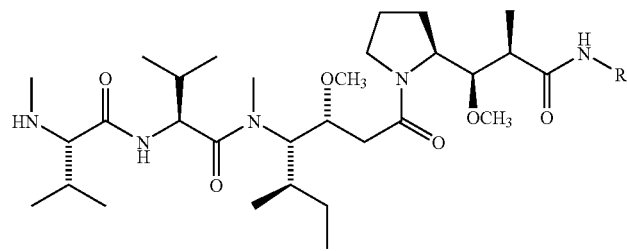
Monomethyl auristatin E (MMAE; 1a) R = 1S, 2R-norephedrine
Monomethyl auristatin F (MMAF; 1b) R = phenylalanine
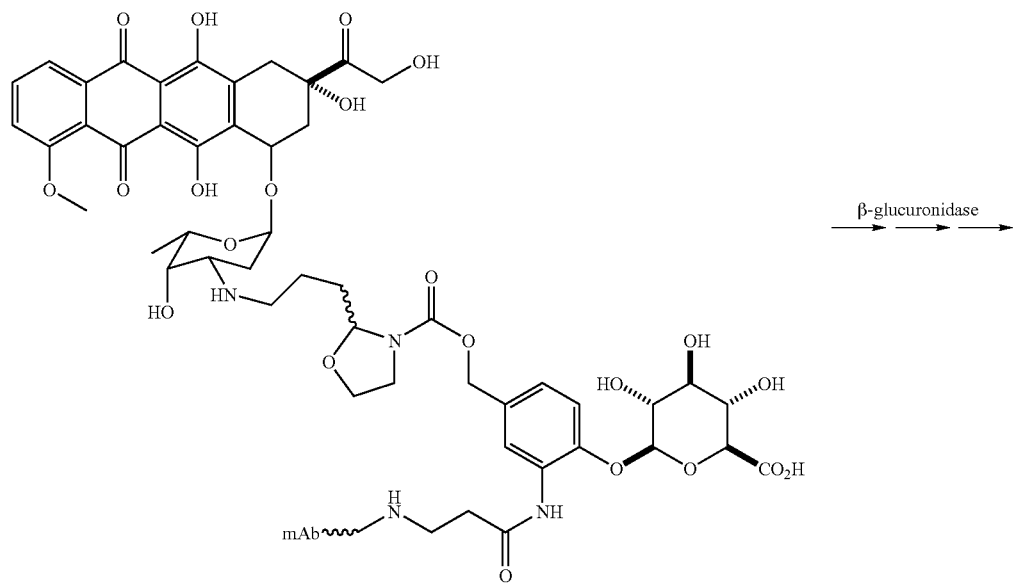

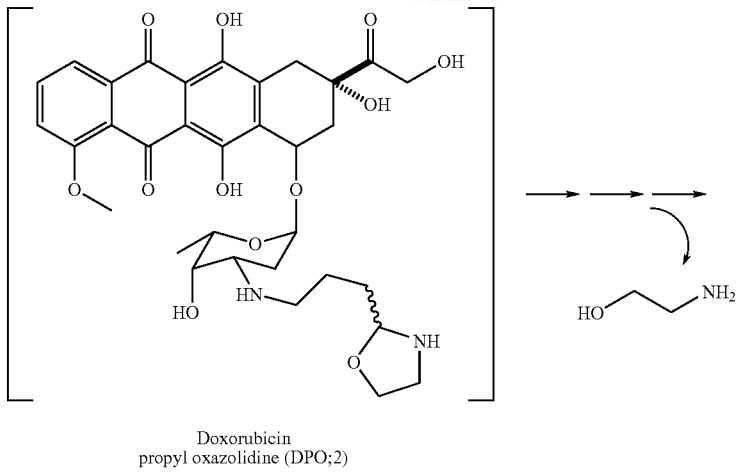
Doxorubicin
propyl oxazolidine (DPO;2)
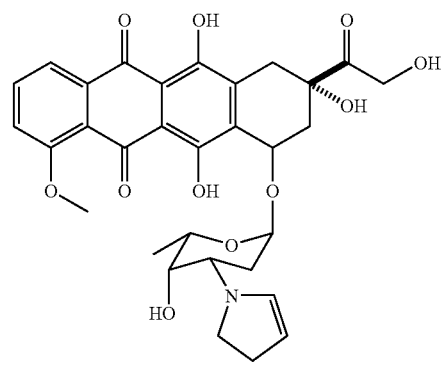
2-Pyrrolinodoxorubicin (4)
↑ esterase
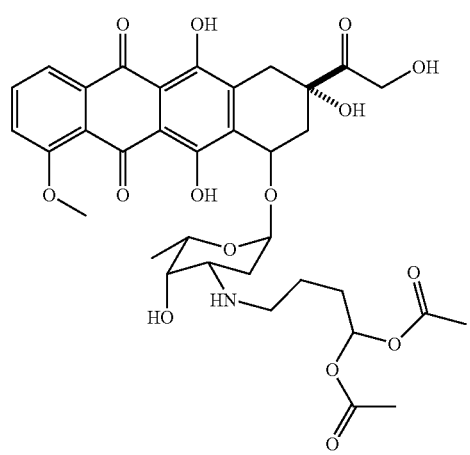

Scheme 2a
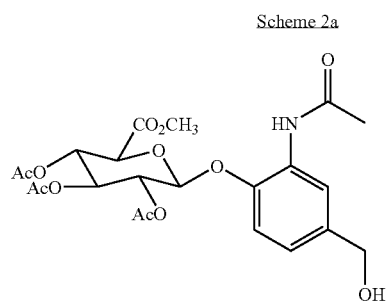
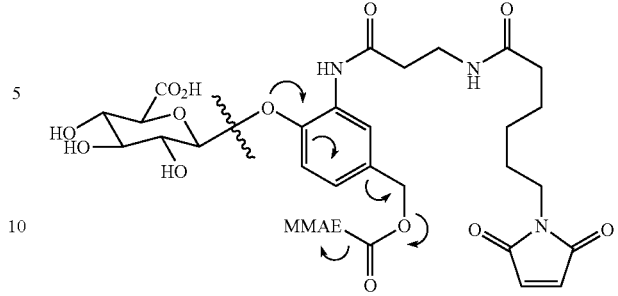
In other embodiments, the glucuronide-based Linker-Drug conjugate can be, for example, bromoacetamide-glucuronide-MMAE; bromoacetamide-glucuronide-MMAF; glucuronide-staurosporine; or glucuronide-amino CBI minor groove binder (SN26597), as shown in the following formula.
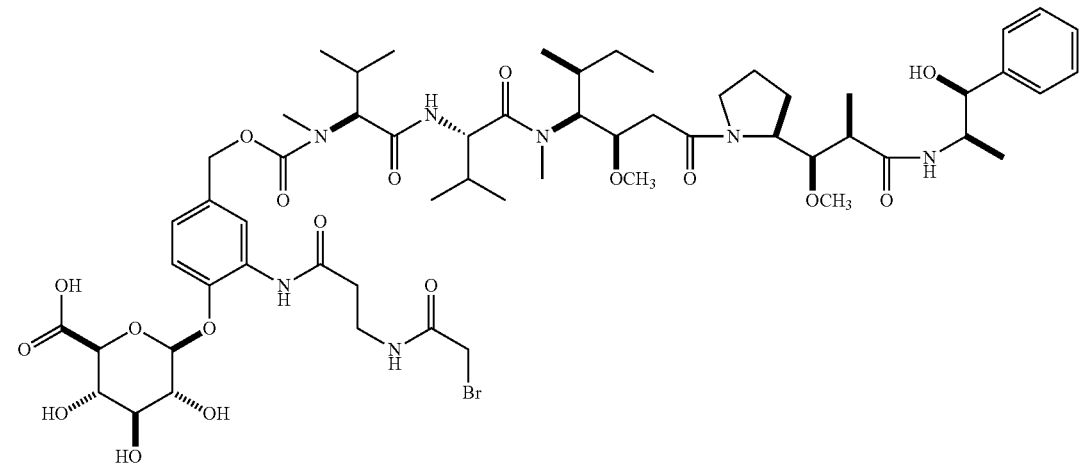
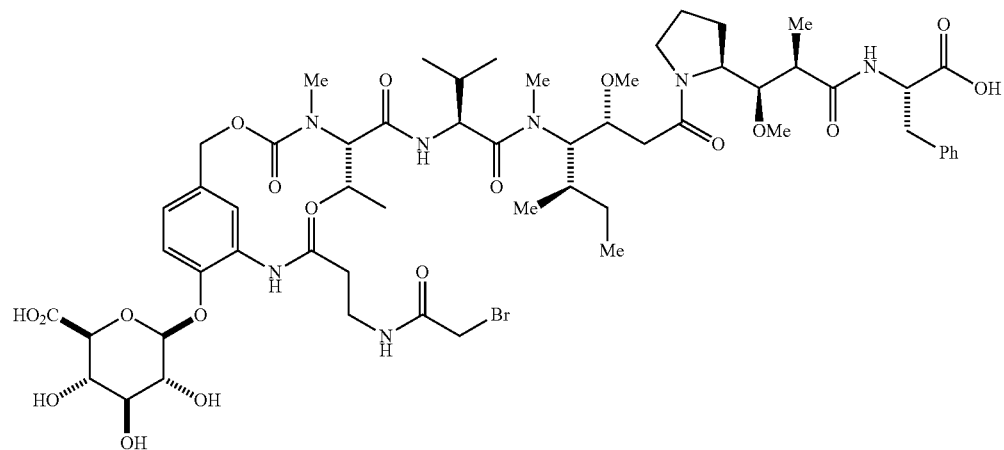

-continued

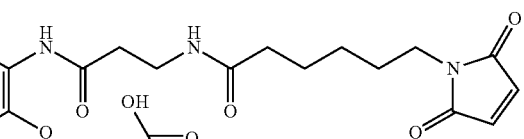
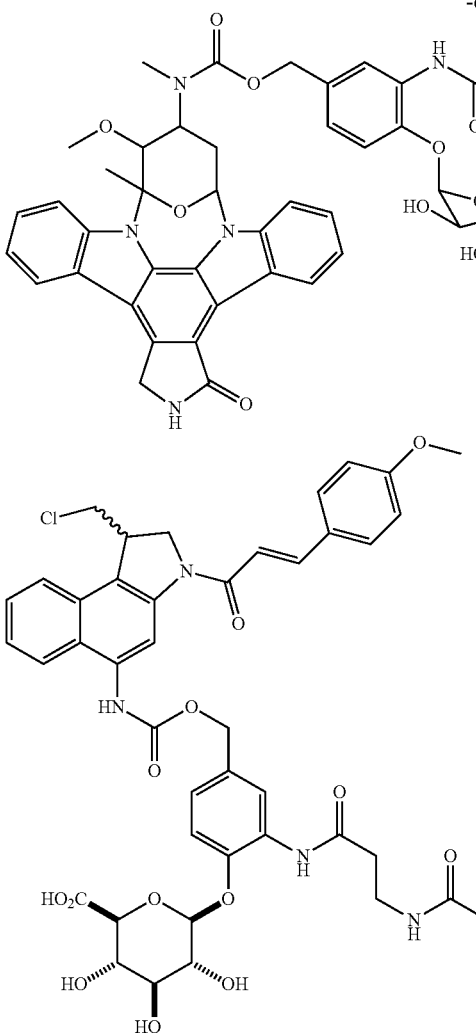

Compositions and Methods of Administration

The present compositions can be in any form that allows for the composition to be administered to a patient. For example, the composition can be in the form of a solid, liquid or gas (aerosol). Typical routes of administration include, without limitation, oral, topical, parenteral, sublingual, rectal, vaginal, ocular, intra-tumor, and intranasal. Parenteral administration includes subcutaneous injections, intravenous, intramuscular, intrasternal injection or infusion techniques. In one aspect, the compositions are administered parenterally. In yet another aspect, the compounds are administered intravenously. In some embodiments, a Ligand Drug conjugate compound is administered in the absence of an administration of a beta-glucuronidase.

Pharmaceutical compositions can be formulated so as to allow a compound to be bioavailable upon administration of the composition to a patient. Compositions can take the form of one or more dosage units, where for example, a tablet can be a single dosage unit, and a container of a compound in aerosol form can hold a plurality of dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of animal (e.g., human), the particular form of the compound, the manner of administration, and the composition employed.

The pharmaceutically acceptable carrier or vehicle can be particulate, so that the compositions are, for example, in tablet or powder form. The carrier(s) can be liquid, with the compositions being, for example, an oral syrup or injectable liquid. In addition, the carrier(s) can be gaseous or particulate, so as to provide an aerosol composition useful in, e.g., inhalatory administration.

When intended for oral administration, the composition is preferably in solid or liquid form, where semi-solid, semi-liquid, suspension and gel forms are included within the forms considered herein as either solid or liquid.

As a solid composition for oral administration, the composition can be formulated into a powder, granule, compressed tablet, pill, capsule, chewing gum, wafer or the like form. Such a solid composition typically contains one or more inert diluents. In addition, one or more of the following can be present: binders such as carboxymethylcellulose, ethyl cellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When the composition is in the form of a capsule, e.g., a gelatin capsule, it can contain, in addition to materials of the above type, a liquid carrier such as polyethylene glycol, cyclodextrin or a fatty oil.

The composition can be in the form of a liquid, e.g., an elixir, syrup, solution, emulsion or suspension. The liquid can be useful for oral administration or for delivery by injection. When intended for oral administration, a composition can comprise one or more of a sweetening agent, preservatives, dye/colorant and flavor enhancer. In a composition for administration by injection, one or more of a surfactant, preservative, wetting agent, dispersing agent, suspending agent, buffer, stabilizer and isotonic agent can also be included.

The liquid compositions, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. A parenteral composition can be enclosed in ampoule, a disposable syringe or a multiple-dose vial made of glass, plastic or other material. Physiological saline is an exemplary adjuvant. An injectable composition is preferably sterile.

The amount of the compound that is effective in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

The compositions comprise an effective amount of a compound such that a suitable dosage will be obtained. Typically, this amount is at least about 0.01% of a compound by weight of the composition. When intended for oral administration, this amount can be varied to range from about 0.1% to about 80% by weight of the composition. In one aspect, oral compositions can comprise from about 4% to about 50% of the compound by weight of the composition. In yet another aspect, present compositions are prepared so that a parenteral dosage unit contains from about 0.01% to about 2% by weight of the compound.

For intravenous administration, the composition can comprise from about 0.01 to about 100 mg of a compound per kg of the animal's body weight. In one aspect, the composition can include from about 1 to about 100 mg of a compound per kg of the animal's body weight. In another aspect, the amount administered will be in the range from about 0.1 to about 25 mg/kg of body weight of a compound.

Generally, the dosage of a compound administered to a patient is typically about 0.01 mg/kg to about 2000 mg/kg of the animal's body weight. In some embodiments, the dosage administered to a patient is between about 0.01 mg/kg to about 10 mg/kg of the animal's body weight. In some embodiments, the dosage administered to a patient is between about 0.1 mg/kg and about 250 mg/kg of the animal's body weight. In some embodiments, the dosage administered to a patient is between about 0.1 mg/kg and about 20 mg/kg of the animal's body weight. In some embodiments, the dosage administered is between about 0.1 mg/kg to about 10 mg/kg of the animal's body weight. In some embodiments, the dosage administered is between about 1 mg/kg to about 15 mg/kg of the animal's body weight. In some embodiments, the dosage administered is between about 1 mg/kg to about 10 mg/kg of the animal's body weight.

The compound or compositions can be administered by any convenient route, for example by infusion or bolus injection, by absorption through epithelial or mucocutaneous linings (e.g., oral mucosa, rectal and intestinal mucosa, etc.). Administration can be systemic or local. Various delivery systems are known, e.g., encapsulation in liposomes, microparticles, microcapsules, capsules, etc., and can be used to administer a compound. In certain embodiments, more than one compound or composition is administered to a patient.

In specific embodiments, it can be desirable to administer one or more compounds or compositions locally to the area in need of treatment. This can be achieved, for example, and not by way of limitation, by local infusion during surgery; topical application, e.g., in conjunction with a wound dressing after surgery; by injection; by means of a catheter; by means of a suppository; or by means of an implant, the implant being of a porous, non-porous, or gelatinous material, including membranes, such as sialastic membranes, or fibers. In one embodiment, administration can be by direct injection at the site (or former site) of a cancer, tumor or neoplastic or pre-neoplastic tissue. In another embodiment, administration can be by direct injection at the site (or former site) of a manifestation of an autoimmune disease.

In certain embodiments, it can be desirable to introduce one or more compounds or compositions into the central nervous system by any suitable route, including intraventricular and intrathecal injection. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant.

In yet another embodiment, the compound or compositions can be delivered in a controlled release system, such as but not limited to, a pump or various polymeric materials can be used. In yet another embodiment, a controlled-release system can be placed in proximity of the target of the compound or compositions, e.g., the brain, thus requiring only a fraction of the systemic dose (see, e.g., Goodson, in Medical Applications of Controlled Release, supra, vol. 2, pp. 115-138 (1984)). Other controlled-release systems discussed in the review by Langer (1990, *Science* 249:1527-1533) can be used.

The term "carrier" refers to a diluent, adjuvant or excipient, with which a compound is administered. Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. In one embodiment, when administered to a patient, the compound or compositions and pharmaceutically acceptable carriers are sterile. Water is an exemplary carrier when the compounds are administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. Other examples of suitable pharmaceutical carriers are described in "Remington's Pharmaceutical Sciences" by E. W. Martin.

In an embodiment, the compounds are formulated in accordance with routine procedures as a pharmaceutical composition adapted for intravenous administration to animals, particularly human beings. Typically, the carriers or vehicles for intravenous administration are sterile isotonic aqueous buffer solutions. Where necessary, the compositions can also include a solubilizing agent. Compositions for intravenous administration can optionally comprise a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where compound is to be administered by infusion, it can be dispensed, for example, with an infusion bottle containing sterile pharmaceutical grade water or saline. Where the compound is administered by injection, an ampoule of sterile water for injection or saline can be provided so that the ingredients can be mixed prior to administration.

Compositions for oral delivery can be in the form of tablets, lozenges, aqueous or oily suspensions, granules, powders, emulsions, capsules, syrups, or elixirs, for example. Orally administered compositions can contain one or more optionally agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compounds. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used.

The compositions can be intended for topical administration, in which case the carrier may be in the form of a solution, emulsion, ointment or gel base. If intended for transdermal administration, the composition can be in the form of a transdermal patch or an iontophoresis device. Topical formulations can comprise a concentration of a compound of from about 0.05% to about 50% w/v (weight per unit volume of composition), in another aspect, from 0.1% to 10% w/v.

The composition can be intended for rectal administration, in the form, e.g., of a suppository which will melt in the rectum and release the compound.

The composition can include various materials that modify the physical form of a solid or liquid dosage unit. For example, the composition can include materials that form a coating shell around the active ingredients. The materials that form the coating shell are typically inert, and can be selected from, for example, sugar, shellac, and other enteric coating agents. Alternatively, the active ingredients can be encased in a gelatin capsule.

The compositions can consist of gaseous dosage units, e.g., it can be in the form of an aerosol. The term aerosol is used to denote a variety of systems ranging from those of colloidal nature to systems consisting of pressurized packages. Delivery can be by a liquefied or compressed gas or by a suitable pump system that dispenses the active ingredients.

Whether in solid, liquid or gaseous form, the present compositions can include a pharmacological agent used in the treatment of cancer, an autoimmune disease or an infectious disease.

Therapeutic Uses of the Conjugates

The conjugates are useful for treating cancer, an autoimmune disease, an infectious disease or other disease in a patient. In some embodiments, the conjugates are administered alone. In other embodiments, the conjugates a co-administered with another therapeutic agent. In some embodiments, the conjugates are co-administered with standard of care chemotherapeutics.

Treatment of Cancer

The conjugates are useful for inhibiting the multiplication of a tumor cell or cancer cell, causing apoptosis in a tumor or cancer cell, or for treating cancer in a patient. The compounds can be used accordingly in a variety of settings for the treatment of animal cancers. Some exemplary particular types of cancers that can be treated with compounds include, but are not limited to, those disclosed in Table 1.

TABLE 1

Solid tumors, including but not limited to:

fibrosarcoma
myxosarcoma
liposarcoma
chondrosarcoma
osteogenic sarcoma
chordoma
angiosarcoma
endotheliosarcoma
lymphangiosarcoma
lymphangioendotheliosarcoma
synovioma
mesothelioma
Ewing's tumor
leiomyosarcoma
rhabdomyosarcoma
colon cancer
rectal cancer
colorectal cancer
kidney cancer
pancreatic cancer
bone cancer
breast cancer
ovarian cancer
prostate cancer
penile carcinoma
esophogeal cancer
gastric cancer
gastrointestinal cancer
stomach cancer
peritoneal cancer
hepatic carcinoma
hepatocellular cancer
liver cancer
oral cancer TABLE 1-continued nasal cancer
throat cancer
squamous cell carcinoma (e.g., epithelial)
basal cell carcinoma
adenocarcinoma
sweat gland carcinoma
sebaceous gland carcinoma
papillary carcinoma
papillary adenocarcinomas
cystadenocarcinoma
medullary carcinoma
bronchogenic carcinoma
renal cell carcinoma
hepatoma
bile duct carcinoma
choriocarcinoma
seminoma
embryonal carcinoma
Wilms' tumor
cervical cancer
uterine cancer
endometrial or uterine carcinoma
vulval cancer
testicular cancer
bladder carcinoma
lung cancer, including small cell lung carcinoma, non-small cell lung cancer, adenocarcinoma of the lung and squamous carcinoma of the lung
epithelial carcinoma
glioma
glioblastoma
glioblastoma multiforme
astrocytoma
medulloblastoma
craniopharyngioma
ependymoma
pinealoma
hemangioblastoma
acoustic neuroma
oligodendroglioma
meningioma
skin cancer
melanoma
neuroblastoma
retinoblastoma
salivary gland carcinoma
thyroid cancer
head cancer
neck cancer
anal cancer
blood-borne cancers, including but not limited to:

acute lymphoblastic leukemia "ALL"
acute lymphoblastic B-cell leukemia
acute lymphoblastic T-cell leukemia
acute myeloblastic leukemia "AML"
acute promyelocytic leukemia "APL"
acute monoblastic leukemia
acute erythroleukemic leukemia
acute megakaryoblastic leukemia
acute myelomonocytic leukemia
acute nonlymphocyctic leukemia
acute undifferentiated leukemia
chronic myelocytic leukemia "CML"
chronic lymphocytic leukemia "CLL"
hairy cell leukemia
multiple myeloma
acute and chronic leukemias:

lymphoblastic
myelogenous
lymphocytic
myelocytic leukemias

TABLE 1-continued

Lymphomas:

Hodgkin's disease
non-Hodgkin's Lymphoma
Multiple myeloma
Waldenström's macroglobulinemia
Heavy chain disease
Polycythemia vera The conjugates provide conjugation-specific tumor or cancer targeting,. thus reducing general toxicity of these compounds. The linker stabilizes the conjugates in blood, yet is cleavable by enzymes within the cell (e.g., lysosomal enzymes), liberating the Drug(s).

Multi-Modality Therapy for Cancer

Cancers, including, but not limited to, a tumor, metastasis, or other disease or disorder characterized by uncontrolled cell growth, can be treated or prevented by administration of a conjugate according to the present invention.

In some embodiments, methods for treating or preventing cancer are provided, including administering to a patient in need thereof an effective amount of a conjugate and a chemotherapeutic agent. In one embodiment, the chemotherapeutic agent is that with which treatment of the cancer has not been found to be refractory. In another embodiment, the chemotherapeutic agent is that with which the treatment of cancer has been found to be refractory. The conjugates can be administered to a patient that has also undergone surgery as treatment for the cancer.

In one embodiment, the additional method of treatment is radiation therapy.

In a specific embodiment, the conjugate is administered concurrently with the chemotherapeutic agent or with radiation therapy. In another specific embodiment, the chemotherapeutic agent or radiation therapy is administered prior or subsequent to administration of a conjugate. In some embodiments, the chemotherapeutic agent or radiation therapy is administered at least an hour, five hours, 12 hours, a day, a week, a month, several months (e.g., up to three months), prior or subsequent to administration of a conjugate.

A chemotherapeutic agent can be administered over a series of sessions. Any one or a combination of the following chemotherapeutic agents can be administered (see infra). With respect to radiation, any radiation therapy protocol can be used depending upon the type of cancer to be treated. For example, but not by way of limitation, x-ray radiation can be administered; in particular, high-energy megavoltage (radiation of greater that 1 MeV energy) can be used for deep tumors, and electron beam and orthovoltage x-ray radiation can be used for skin cancers. Gamma-ray emitting radioisotopes, such as radioactive isotopes of radium, cobalt and other elements, can also be administered.

Additionally, methods of treatment of cancer with a conjugate are provided as an alternative to chemotherapy or radiation therapy where the chemotherapy or the radiation therapy has proven or can prove to be too toxic, e.g., results in unacceptable or unbearable side effects, for the subject being treated. The animal being treated can, optionally, be treated with another cancer treatment such as surgery, radiation therapy or chemotherapy, depending on which treatment is found to be acceptable or bearable.

The conjugates can also be used in an in vitro or ex vivo fashion, such as for the treatment of certain cancers, including, but not limited to leukemias and lymphomas, such treatment involving autologous stem cell transplants. This can involve a multi-step process in which the animal's autologous hematopoietic stem cells are harvested and purged of all cancer cells, the animal's remaining bone-marrow cell population is then eradicated via the administration of a high dose of a conjugate with or without accompanying high dose radiation therapy, and the stem cell graft is infused back into the animal. Supportive care is then provided while bone marrow function is restored and the animal recovers.

Multi-Drug Therapy for Cancer

Methods for treating cancer including administering to a patient in need thereof an effective amount of a conjugate and another therapeutic agent that is an anti-cancer agent are disclosed.

Examples of chemotherapeutic agents include alkylating agents such as thiotepa and CYTOXAN® cyclosphosphamide; alkyl sulfonates such as busulfan, improsulfan, piposulfan and treosulfan; decarbazine; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; TLK 286 (TELCYTA™); acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; bisphosphonates, such as clodronate; antibiotics such as the enediyne antibiotics (e.g., calicheamicin, especially calicheamicin gamma1I and calicheamicin omega1I (see, e.g., Agnew, *Chem. Intl. Ed. Engl.* 33:183-186 (1994)) and anthracyclines such as annamycin, AD 32, alcarubicin, daunorubicin, dexrazoxane, DX-52-1, epirubicin, GPX-100, idarubicin, KRN5500, menogaril, dynemicin, including dynemicin A, an esperamicin, neocarzinostatin chromophore and related chromoprotein enediyne antibiotic chromophores, aclacinomysins, actinomycin, authramycin, azaserine, bleomycins (e.g., bleomycinA2, bleomycin B2 and peplomycin), cactinomycin, carabicin, carminomycin, carzinophilin, chromomycinis, dactinomycin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin, liposomal doxorubicin, and deoxydoxorubicin), esorubicin, marcellomycin, mitomycins such as mitomycin C, mycophenolic acid, tiazofurin, ribavarin, EICAR, nogalamycin, olivomycins, peplomycin, poffiromycin, puromycin, quelamycin, rodorubicin, streptonigrin, streptozocin, tubercidin, ubenimex, zinostatin, and zorubicin; folic acid analogues such as denopterin, pteropterin, and trimetrexate; purine analogs such as fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replenisher such as folinic acid (leucovorin); aceglatone; anti-folate antineoplastic agents such as ALIMTA®, LY231514 pemetrexed, dihydrofolate reductase inhibitors such as methotrexate and trimetrexate, anti-metabolites such as 5-fluorouracil (5-FU) and its prodrugs such as UFT, S-1 and capecitabine, and thymidylate synthase inhibitors and glycinamide ribonucleotide formyltransferase inhibitors such as raltitrexed (TOMUDEXRM, TDX); inhibitors of dihydropyrimidine dehydrogenase such as eniluracil; aldophosphamide glycoside; aminolevulinic acid; amsacrine; bestrabucil; bisantrene; edatraxate; defofamine; demecolcine; diaziquone; elfornithine; elliptinium acetate; an epothilone; etoglucid; gallium nitrate; hydroxyurea; deferoxamine; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®)); dacarbazine; mannomustine; mitobronitol; mitolactol; pipobroman; gacytosine; cytosine arabinoside ("Ara-C"); cyclophosphamide; thiotepa; taxoids and taxanes, e.g., TAXOL® paclitaxel (Bristol-Myers Squibb Oncology, Princeton, N.J.), ABRAXANETM Cremophorfree, albumin-engineered nanoparticle formulation of paclitaxel.(American Pharmaceutical Partners, Schaumberg, Ill.), and TAXOTERE® doxetaxel (Rhône-Poulenc Rorer, Antony, France); chloranbucil; gemcitabine (GEMZAR®); 6-thioguanine; mercaptopurine; platinum; platinum analogs or platinum-based analogs such as cisplatin, oxaliplatin and carboplatin; vinblastine (VELBAN®)); epipodophyllins such as etoposide (VP-16), teniposide, tepotecan, 9-aminocamptothecin, camptothecin and crisnatol; ifosfamide; mitoxantrone; vinca alkaloids such as vincristine (ONCOVIN®), vindesine, vinca alkaloid, and vinorelbine (NAVELBINE®)); novantrone; edatrexate; daunomycin; aminopterin; xeloda; ibandronate; topoisomerase inhibitor RFS 2000; difluorometlhylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATINTM) combined with 5-FU and leucovorin.

In some embodiments, the anticancer agent is methotrexate, taxol, L-asparaginase, mercaptopurine, thioguanine, hydroxyurea, cytarabine, cyclophosphamide, ifosfamide, nitrosoureas, cisplatin, carboplatin, mitomycin, dacarbazine, procarbizine, topotecan, nitrogen mustards, cytoxan, etoposide, 5-fluorouracil, BCNU, irinotecan, camptothecins, bleomycin, doxorubicin, idarubicin, daunorubicin, dactinomycin, plicamycin, mitoxantrone, asparaginase, vinblastine, vincristine, vinorelbine, paclitaxel, or docetaxel.

In some embodiments, the anti-cancer agent includes, but is not limited to, a drug listed in Table 2.

TABLE 2

| Alkylating agents | |
| --- | --- |
| Nitrogen mustards: | cyclophosphamide |
| | ifosfamide |
| | trofosfamide |
| | chlorambucil |
| | melphalan |
| Nitrosoureas: | carmustine (BCNU) |
| | lomustine (CCNU) |
| Alkylsulphonates | busulfan |
| | treosulfan |
| Triazenes: | decarbazine |
| Platinum containing compounds: | cisplatin |
| | carboplatin |

TABLE 2-continued

| Plant Alkaloids | |
| --- | --- |
| Vinca alkaloids: | vincristine |
| | vinblastine |
| | vindesine |
| | vinorelbine |
| Taxoids: | paclitaxel |
| | docetaxol |
| DNA Topoisomerase Inhibitors | |
| Epipodophyllins: | etoposide |
| | teniposide |
| | topotecan |
| | 9-aminocamptothecin |
| | camptothecin |
| | crisnatol |
| mitomycins: | mitomycin C |
| Anti-metabolites | |
| Anti-folates: | |
| DHFR inhibitors: | methotrexate |
| | trimetrexate |
| IMP dehydrogenase Inhibitors: | mycophenolic acid |
| | tiazofurin |
| | ribavirin |
| | EICAR |
| Ribonucleotide reductase Inhibitors: | hydroxyurea |
| | deferoxamine |
| Pyrimidine analogs: | |
| Uracil analogs | 5-Fluorouracil |
| | floxuridine |
| | doxifluridine |
| | ratitrexed |
| Cytosine analogs | cytarabine (ara C) |
| | cytosine arabinoside |
| | fludarabine |
| Purine analogs: | mercaptopurine |
| | thioguanine |
| Hormonal therapies: | |
| Receptor antagonists: | |
| Anti-estrogen | tamoxifen |
| | raloxifene |
| | megestrol |
| LHRH agonists: | goscrelin |
| | leuprolide acetate |
| Anti-androgens: | flutamide |
| | bicalutamide |
| Retinoids/Deltoids | |
| Vitamin D3 analogs: | EB 1089 |
| | CB 1093 |
| | KH 1060 |
| Photodynamic therapies: | vertoporfin (BPD-MA) |
| | phthalocyanine |
| | photosensitizer Pc4 |
| | demethoxy-hypocrellin A |
| | (2BA-2-DMHA) |
| Cytokines: | Interferon-α |
| | Interferon-γ |
| | tumor necrosis factor |
| Others: | Gemcitabine |
| | Velcade |
| | Revamid |
| | Thalamid |
| Isoprenylation inhibitors: | Lovastatin |
| Dopaminergic neurotoxins: | 1-methyl-4-phenylpyridinium ion |
| Cell cycle inhibitors: | staurosporine |
| Actinomycins: | Actinomycin D |
| | dactinomycin |
| Bleomycins: | bleomycin A2 |
| | bleomycin B2 |
| | peplomycin |

TABLE 2-continued

| Anthracyclines: | daunorubicin |
| --- | --- |
| | Doxorubicin (adriamycin) |
| | idarubicin |
| | epirubicin |
| | pirarubicin |
| | zorubicin |
| | mtoxantrone |
| MDR inhibitors: | verapamil |
| $Ca^{2+}$ATPase inhibitors: | thapsigargin |

Treatment of Autoimmune Diseases

The conjugates are useful for killing or inhibiting the replication of a cell that produces an autoimmune disease or for treating an autoimmune disease. The conjugates can be used accordingly in a variety of settings for the treatment of an autoimmune disease in a patient.

Particular types of autoimmune diseases that can be treated with the conjugates include, but are not limited to, Th2 lymphocyte related disorders (e.g., atopic dermatitis, atopic asthma, rhinoconjunctivitis, allergic rhinitis, Omenn's syndrome, systemic sclerosis, and graft versus host disease); Th1 lymphocyte-related disorders (e.g., rheumatoid arthritis, multiple sclerosis, psoriasis, Sjorgren's syndrome, Hashimoto's thyroiditis, Grave's disease, primary biliary cirrhosis, Wegener's granulomatosis, and tuberculosis); activated B lymphocyte-related disorders (e.g., systemic lupus erythematosus, Goodpasture's syndrome, rheumatoid arthritis, and type I diabetes); and those disclosed in Table 3.

TABLE 3

Active Chronic Hepatitis
Addison's Disease
Allergic Alveolitis
Allergic Reaction
Allergic Rhinitis
Alport's Syndrome
Anaphlaxis
Ankylosing Spondylitis
Anti-phosholipid Syndrome
Arthritis
Ascariasis
Aspergillosis
Atopic Allergy
Atropic Dermatitis
Atropic Rhinitis
Behcet's Disease
Bird-Fancier's Lung
Bronchial Asthma
Caplan's Syndrome
Cardiomyopathy
Celiac Disease
Chagas' Disease
Chronic Glomerulonephritis
Cogan's Syndrome
Cold Agglutinin Disease
Congenital Rubella Infection
CREST Syndrome
Crohn's Disease
Cryoglobulinemia
Cushing's Syndrome
Dermatomyositis
Discoid Lupus
Dressler's Syndrome
Eaton-Lambert Syndrome
Echovirus Infection
Encephalomyelitis
Endocrine opthalmopathy
Epstein-Barr Virus Infection
Equine Heaves
Erythematosis
Evan's Syndrome
Felty's Syndrome
Fibromyalgia

TABLE 3-continued

Fuch's Cyclitis
Gastric Atrophy
Gastrointestinal Allergy
Giant Cell Arteritis
Glomerulonephritis
Goodpasture's Syndrome
Graft v. Host Disease
Graves' Disease
Guillain-Barre Disease
Hashimoto's Thyroiditis
Hemolytic Anemia
Henoch-Schonlein Purpura
Idiopathic Adrenal Atrophy
Idiopathic Pulmonary Fibritis
IgA Nephropathy
Inflammatory Bowel Diseases
Insulin-dependent Diabetes Mellitus
Juvenile Arthritis
Juvenile Diabetes Mellitus (Type I)
Lambert-Eaton Syndrome
Laminitis
Lichen Planus
Lupoid Hepatitis
Lupus
Lymphopenia
Meniere's Disease
Mixed Connective Tissue Disease
Multiple Sclerosis
Myasthenia Gravis
Pernicious Anemia
Polyglandular Syndromes
Presenile Dementia
Primary Agammaglobulinemia
Primary Biliary Cirrhosis
Psoriasis
Psoriatic Arthritis
Raynauds Phenomenon
Recurrent Abortion
Reiter's Syndrome
Rheumatic Fever
Rheumatoid Arthritis
Sampter's Syndrome
Schistosomiasis
Schmidt's Syndrome
Scleroderma
Shulman's Syndrome
Sjorgen's Syndrome
Stiff-Man Syndrome
Sympathetic Ophthalmia
Systemic Lupus Erythematosis
Takayasu's Arteritis
Temporal Arteritis
Thyroiditis
Thrombocytopenia
Thyrotoxicosis
Toxic Epidermal Necrolysis
Type B Insulin Resistance
Type I Diabetes Mellitus
Ulcerative Colitis
Uveitis
Vitiligo
Waldenstrom's Macroglobulemia
Wegener's Granulomatosis Multi-Drug Therapy of Autoimmune Diseases Methods for treating an autoimmune disease are also disclosed, including administering to a patient in need thereof an effective amount of a conjugate and another therapeutic agent known for the treatment of an autoimmune disease. In one embodiment, the anti-autoimmune disease agent includes, but is not limited to, agents listed in Table 4.

TABLE 4 cyclosporine
cyclosporine A
mycophenylate mofetil

TABLE 4-continued sirolimus
tacrolimus
enanercept
prednisone
azathioprine
methotrexate cyclophosphamide
prednisone
aminocaproic acid
chloroquine
hydroxychloroquine
hydrocortisone
dexamethasone
chlorambucil
DHEA
danazol
bromocriptine
meloxicam
infliximab The conjugates are useful for killing or inhibiting the multiplication of a cell that produces an infectious disease or for treating an infectious disease.

In one embodiment, the conjugates kill or inhibit the multiplication of cells that produce a particular infectious disease.

Particular types of infectious diseases that can be treated with the conjugates include, but are not limited to, those disclosed in Table 5.

TABLE 5

Bacterial Diseases:

Diphtheria
Pertussis
Occult Bacteremia
Urinary Tract Infection
Gastroenteritis
Cellulitis
Epiglottitis
Tracheitis
Adenoid Hypertrophy
Retropharyngeal Abcess
Impetigo
Ecthyma
Pneumonia
Endocarditis
Septic Arthritis
*Pneumococcal*
Peritonitis
Bactermia
Meningitis
Acute Purulent Meningitis
Urethritis
Cervicitis
Proctitis
Pharyngitis
Salpingitis
Epididymitis
Gonorrhea
Syphilis
Listeriosis
Anthrax
Nocardiosis
Salmonella
Typhoid Fever
Dysentery
Conjunctivitis
Sinusitis
Brucellosis
Tullaremia
Cholera
Bubonic Plague
Tetanus
Necrotizing Enteritis
Actinomycosis
Mixed Anaerobic Infections TABLE 5-continued Syphilis
Relapsing Fever
Leptospirosis
Lyme Disease
Rat Bite Fever
Tuberculosis
Lymphadenitis
Leprosy
Chlamydia
Chlamydial Pneumonia
Trachoma
Inclusion Conjunctivitis
Systemic Fungal Diseases:

Histoplamosis
Coccidiodomycosis
Blastomycosis
Sporotrichosis
Cryptococcsis
Systemic Candidiasis
Aspergillosis
Mucormycosis
Mycetoma
Chromomycosis
Rickettsial Diseases:

Typhus
Rocky Mountain Spotted Fever
Ehrlichiosis
Eastern Tick-Borne Rickettsioses
Rickettsialpox
Q Fever
Bartonellosis
Parasitic Diseases:

Malaria
Babesiosis
African Sleeping Sickness
Chagas' Disease
Leishmaniasis
Dum-Dum Fever
Toxoplasmosis
Meningoencephalitis
Keratitis
Entamebiasis
Giardiasis
Cryptosporidiasis
Isosporiasis
Cyclosporiasis
Microsporidiosis
Ascariasis
Whipworm Infection
Hookworm Infection
Threadworm Infection
Ocular Larva Migrans
Trichinosis
Guinea Worm Disease
Lymphatic Filariasis
Loiasis
River Blindness
Canine Heartworm Infection
Schistosomiasis
Swimmer's Itch
Oriental Lung Fluke
Oriental Liver Fluke
Fascioliasis
Fasciolopsiasis
Opisthorchiasis
Tapeworm Infections
Hydatid Disease
Alveolar Hydatid Disease
Viral Diseases:

Measles
Subacute sclerosing panencephalitis
Common Cold
Mumps
Rubella
Roseola
Fifth Disease TABLE 5-continued Chickenpox
Respiratory syncytial virus infection
Croup
Bronchiolitis
Infectious Mononucleosis
Poliomyelitis
Herpangina
Hand-Foot-and-Mouth Disease
Bornholm Disease
Genital Herpes
Genital Warts
Aseptic Meningitis
Myocarditis
Pericarditis
Gastroenteritis
Acquired Immunodeficiency Syndrome (AIDS)
Human Immunodeficiency Virus (HIV)
Reye's Syndrome
Kawasaki Syndrome
Influenza
Bronchitis
Viral "Walking" Pneumonia
Acute Febrile Respiratory Disease
Acute pharyngoconjunctival fever
Epidemic keratoconjunctivitis
Herpes Simplex Virus 1 (HSV-1)
Herpes Simplex Virus 2 (HSV-2)
Shingles
Cytomegalic Inclusion Disease
Rabies
Progressive Multifocal Leukoencephalopathy
Kuru
Fatal Familial Insomnia
Creutzfeldt-Jakob Disease
Gerstmann-Straussler-Scheinker Disease
Tropical Spastic Paraparesis
Western Equine Encephalitis
California Encephalitis
St. Louis Encephalitis
Yellow Fever
Dengue
Lymphocytic choriomeningitis
Lassa Fever
Hemorrhagic Fever
Hantvirus Pulmonary Syndrome
Marburg Virus Infections
Ebola Virus Infections
Smallpox Multi-Drug Therapy of Infectious Diseases Methods for treating an infectious disease are disclosed, including administering to a patient in need thereof a conjugate and another therapeutic agent that is an anti-infectious disease agent. In one embodiment, the anti-infectious disease agent is, but not limited to, agents listed in Table 6.

TABLE 6

β-Lactam Antibiotics:

Penicillin G
Penicillin V
Cloxacilliin
Dicloxacillin
Methicillin
Nafcillin
Oxacillin
Ampicillin
Amoxicillin
Bacampicillin
Azlocillin
Carbenicillin
Mezlocillin
Piperacillin
Ticarcillin TABLE 6-continued Aminoglycosides:

Amikacin
Gentamicin
Kanamycin
Neomycin
Netilmicin
Streptomycin
Tobramycin
Macrolides:

Azithromycin
Clarithromycin
Erythromycin
Lincomycin
Clindamycin
Tetracyclines:

Demeclocycline
Doxycycline
Minocycline
Oxytetracycline
Tetracycline
Quinolones:

Cinoxacin
Nalidixic Acid
Fluoroquinolones:

Ciprofloxacin
Enoxacin
Grepafloxacin
Levofloxacin
Lomefloxacin
Norfloxacin
Ofloxacin
Sparfloxacin
Trovafloxicin
Polypeptides:

Bacitracin
Colistin
Polymyxin B
Sulfonamides:

Sulfisoxazole
Sulfamethoxazole
Sulfadiazine
Sulfamethizole
Sulfacetamide
Miscellaneous Antibacterial Agents:

Trimethoprim
Sulfamethazole
Chloramphenicol
Vancomycin
Metronidazole
Quinupristin
Dalfopristin
Rifampin
Spectinomycin
Nitrofurantoin
Antiviral Agents:
General Antiviral Agents:

Idoxuradine
Vidarabine
Trifluridine
Acyclovir
Famcicyclovir
Pencicyclovir
Valacyclovir
Gancicyclovir
Foscarnet
Ribavirin
Amantadine
Rimantadine
Cidofovir TABLE 6-continued Antisense Oligonucleotides
Immunoglobulins
Inteferons
Drugs for HIV infection:

Tenofovir
Emtricitabine
Zidovudine
Didanosine
Zalcitabine
Stavudine
Lamivudine
Nevirapine
Delavirdine
Saquinavir
Ritonavir
Indinavir
Nelfinavir

EXAMPLES

The invention is further described in the following examples, which are not intended to limit the scope of the invention. Cell lines described in the following examples were maintained in culture according to the conditions specified by the American Type Culture Collection (ATCC) or Deutsche Sammlung von Mikroorganismen und Zellkulturen GmbH, Braunschweig, Germany (DMSZ), unless otherwise specified. Cell culture reagents were obtained from Invitrogen Corp., Carlsbad, Calif. unless otherwise specified.

Unless otherwise indicated, all anhydrous solvents were commercially obtained and stored in Sure-seal® bottles under nitrogen. All other reagents and solvents were purchased as the highest grade available and used without further purification. NMR spectra were recorded on Varian Mercury 400 MHz Instrument. Chemical shifts ($\delta$) are reported in parts per million (ppm) referenced to tetramethylsilane at 0.00 and coupling constants (J) are reported in Hz. Low resolution mass spectral data were acquired on a Micromass ZMD mass spectrometer interfaced with an HP Agilent 1100 high performance liquid chromatography instrument for LC-MS. Products were eluted on a Phenomenex Synergi 2.0×150 mm, 4$\mu$, 80 Å MAX RP column using a linear gradient of mobile phase B ($CH_3CN$ with 0.05% $HCO_2H$) in A (0.05% aqueous $HCO_2H$) at 0.4 mL/min. Unless otherwise specified, the reported retention times ($t_R$) are those from LC-MS. High resolution (exact mass) data were obtained at the University of Washington Medicinal Chemistry Mass Spectrometry Center on a Bruker APEXIII 47e [FT(ICR)]MS. Analytical HPLC was conducted on a Waters 2695 instrument using a Waters 2996 PDA and Millenium software.

For analytical HPLC the stationary phase used was a Phenomenex Synergi 4.6×150 mm, 4$\mu$, 80 Å MAX RP column. Products were eluted on either acidic linear gradients (designated gradient A) of mobile phase B ($CH_3CN$ with 0.05% $HCO_2H$; 10% to 95% over 8 min) in A (0.05% aqueous TFA), or neutral linear gradients (designated gradient N) of mobile phase B ($CH_3CN$; 10% to 90% over 10 min, then hold at 90% for 5 min) in A (5.0 mM $NH_4H_2PO_4$) at a flow rate of 1.0 mL/min. Preparative HPLC purifications were performed on Varian instrument equipped with C12 Phenomenex Synergy MAX-RP 4$\mu$ reversed phase column, 250×21.2 mm, eluting with 0.1% TFA in a water-acetonitrile gradient. Radial chromatography was performed on a Chromatotron® instrument (Harrison Research, Palo Alto, Calif.) on normal phase silica plates (Analtech, Newark, Del.). Preparative thin layer chromatography was performed on Whatman 20×20 cm, 500$\mu$, 60

Å silica gel plates. All other preparative normal phase purifications were done by standard flash silica gel chromatography using Whatman Science 60 Å 230-400 mesh silica gel as adsorbent.

Example 1

Syntheses (2S,3S,4S,5R,6S)-methyl-6-(2-(3-(((9H-fluoren-9yl)methoxy)carbonyl-amino)propanamido)-4-(hydroxymethyl)phenoxy)-3,4,5-triacetoxy-tetrahydro-2H-pyran-2-carboxylate (11): To a solution of the aniline 5 (74 mg, 0.163 mmol) in dichloromethane (6 mL) was added DIPEA (57 µL, 0.33 mmol). The acid chloride 6 (65 mg, 0.20 mmol) was added and the mixture was stirred for 30 min. The mixture was poured into saturated aqueous sodium bicarbonate and was extracted with ethyl acetate (3×50 mL). The combined extracts were washed with water and brine and were dried over sodium sulfate. Filtration and concentration gave a residue that was purified via radial chromatography using 5% methanol in dichloromethane as mobile phase to give 106 mg (87%) of 11 as a white solid: $^1$H NMR (d6-DMSO) δ1.98 (s, 3H), 1.99 (s, 6H), 2.52 (m, 2H) 3.27 (m, 2H), 3.32 (s, 3H), 4.20 (m, 1H), 4.26 (m, 1H), 4.39 (d, 2H, J=6.3 Hz), 4.70 (d, 1H, J=9.7 Hz), 5.04 (t, 1H, J=9.6 Hz), 5.15 (m, 2H), 5.48 (t, 1H, J=9.4 Hz), 5.54 (d, 1H, J=7.6 Hz), 5.75 (s, 1H), 7.02 (q, 2H, J=4.3 Hz) 7.30 (m, 2H), 7.39 (t, 4H, J=7.72 Hz), 7.67 (d, 2H, J=7.6 Hz), 7.80 (s, 1H), 7.87 (d, 2H, J=7.6 Hz), 8.72 (s, 1H); LC-MS m/z (ES$^+$), 749.04 (M+H)$^+$.

(2S,3S,4S,5R,6S)-methyl-6-(2-(3-(((9H-fluoren-9yl)methoxy)carbonyl-amino)propanamido)-4-(((4-nitrophenoxy)carbonyloxy)methyl)phenoxy)-3,4,5-triacetoxy-tetrahydro-2H-pyran-2-carboxylate (7): To a mixture of benzyl alcohol 11 (105 mg, 0.14 mmol) in DMF (4 mL) was added bis p-nitrophenyl carbonate (85 mg, 0.28 mmol) and DIPEA (36 µL, 0.21 mmol). The mixture was stirred for 16 h at an ambient temperature and was concentrated under reduced pressure to an oily residue. This material was dissolved in dichloromethane and aspirated directly onto a 1 mm radial Chromatotron plate and eluted with 50% ethyl acetate in hexanes followed by ethyl acetate to give 83% (106 mg) of 7 as a solid: $^1$H NMR (d6-DMSO) δ1.98 (s, 3H), 1.99 (s, 3H), 1.99 (s, 3H), 2.52 (m, 2H), 3.28 (m, 2H), 3.62 (s, 3H), 4.20 (m, 1H), 4.27 (m, 2H), 4.73 (d, 1H, J=9.8 Hz), 5.05 (t, 1H, J=9.6 Hz), 5.18 (t, 1H, J=9.4 Hz), 5.21 (s, 2H), 5.49 (t, 1H, J=10.2 Hz), 7.10 (d, 1H, J=8.2 Hz), 7.22 (m, 1H), 7.30 (m, 2H), 7.39 (m, 4H, J=7.0 Hz), 7.55 (d, 2H, J=9.2 Hz), 7.67 (d, 2H, J=5.2 Hz), 7.87 (d, 2H, J=7.0 Hz), 7.97 (s, 1H), 8.29 (d, 2H, J=9.0 Hz), 8.83 (s, 1H); , LC-MS m/z (ES$^+$), 914.03 (M+H)$^+$.

Monomethyl Auristatin E (MMAE): MMAE (1a) was prepared at Albany Molecule Research, Inc (Albany, N.Y.). The synthesis of MMAE (1a) has been described previously (Doronina et al., Nat Biotechnol 21:778-84 (2003); the disclosure of which is incorporated by reference herein).

Monomethyl Auristatin F (MMAF): Intermediates for the synthesis of MMAF (1b) were prepared at Albany Molecule Research, Inc (Albany, N.Y.). The synthesis of MMAF (1b) has been described previously (Doronina et al., Bioconjug Chem. 17(1):114-124 (2006); and U.S. Patent Publication 2005-0238649; the disclosures of which are incorporated by reference herein).

MMAF Carbonate (8) To a mixture of the p-nitrophenyl carbonate 7 (30 mg, 0.033 mmol) and monomethyl auristatin F (MMAF) (1b; 29 mg, 0.039 mmol) was added DMF (0.8 mL) and pyridine (0.2 mL). (The synthesis of MMAF has been described previously (Doronina et al., Bioconjug Chem. 17(1):114-124 (2006); and U.S. Patent Publication 2005-0238649; the disclosures of which are incorporated by reference herein). DIPEA (7 µL, 0.04 mmol) was added followed by HOAt (1 mg, 7 µmol). The reaction mixture was stirred for 16 h at an ambient temperature. The mixture was concentrated under reduced pressure and was chromatographed on a 1 mm Chromatotron plate, eluting with a 1 to 5% methanol in dichloromethane gradient containing 1% acetic acid. The final UV active (254 nm) band to elute was product. This gave 44% (22 mg) of 8 as a solid material. The material was carried forward without analytical characterization.

MMAF glucuronide amine: To a mixture of the MMAF carbamate (22 mg, 0.015 mmol) in methanol (1 mL) at 0° C. was added a solution of LiOH monohydrate (5.5 mg, 0.132 mmol) in water (1 mL). The mixture was stirred for 15 min at 0° C. and the reaction mixture was neutralized using acetic acid (8 µL) and was concentrated under reduced pressure: LC-MS m/z (ES$^-$), 1364.09 (M–H)$^+$, 9.78 min.

The resulting material was dissolved in DMF (0.8 mL) and was treated with piperidine (0.2 mL). The mixture was stirred for 5 min and was concentrated under reduced pressure. The material was taken up in water and purified via preparative HPLC to give 12 mg (72%) as a white solid: $^1$H NMR (CD$_3$OD) (0.52 (d), 0.59 (d), 0.75-1.1 (m), 1.1-1.35 (m), 1.32-1.67 (m), 1.70-2.10 (m), 2.15-2.50 (m), 2.83-3.05 (m), 3.11 (s), 3.15-3.42 (m), 3.45-3.68 (m), 3.85 (m), 3.95 (m), 4.00-4.18 (m), 4.19-4.30 (m), 4.50-4.97 (m), 5.00-5.20 (m), 7.09-7.29 (m), 7.65 (d), 7.75 (d), 7.82 (d), 7.88 (d), 8.18 (d), 8.25 (m), 8.35 (d), 8.40 (d), 8.59 (d); LC-MS m/z (ES$^-$), 1144.66 (M–H)$^+$.

MMAE glucuronide maleimide (9a): Compound 9a was prepared in a manner identical to 9b (infra) starting with MMAE (1a) and compound 7. Compound 9a was obtained as a white solid: $^1$H NMR (CD$_3$OD); δ0.64-1.01 (m, 24H), 1.12 (t, J=6.9 Hz, 3H), 1.16 (d, J=6.5 Hz, 1H), 1.23 (m, 1H), 1.4 (m, 1H), 1.45-1.63 (m, 5H), 1.67-1.98 (m, 2H), 2.19 (m, 3H), 2.42-2.54 (m, 1H), 2.63 (m, 2H), 2.96 (m, 4H), 3.1 (s, 2H), 3.12-3.39 (m, 3H), 3.40-3.73 (m, 9H), 3.85-3.96 (m, 1H), 4.04 (m, 1H), 4.13-4.27 (m, 2H), 4.52 (m, 1H), 4.59-4.68 (m, 2H), 4.65-5.0 (m, 2H), 5.0-5.17 (m, 2H), 6.78 (s, 2H), 7.09 (m, 1H), 7.20 (m, 3H), 7.3 (m, 3H), 7.38 (d, J=7.6 Hz, 3H), 7.75-8.01 (m, 2H), 8.26 (d, J=9.0 Hz, 1H), 8.32 (m, 1H); LC-MS m/z (ES$^+$) 1323.01 (M+H), 6.88 min; HRMS m/z for $C_{66}H_{97}N_8O_{20}Na_2$ (M–H+2Na)$^+$ calcd, 1367.6615; found, 1367.6616.

MMAF glucuronide maleimide (9b): To a mixture of the amine (12 mg, 0.011 mmol) in DMF (1 mL) was added MC-OSu (10; 5.2 mg) followed by DIPEA (6 µL). After 15 min., the reaction mixture was concentrated under reduced pressure, was dissolved in a mixture of water and DMSO (1:1; 1 mL) and was purified via preparative HPLC. This gave 9.4 mg (64%) of 9b as a white solid: $^1$H NMR (CD$_3$OD) δ0.66-1.05 (m, 22H), 1.10-1.27 (m, 9H), 1.33-1.43 (m, 2H), 1.44-1.62 (m, 6H), 1.66-2.05 (m, 5H), 2.15-2.35 (m, 4H), 2.40-2.50 (m, 2H), 2.60-2.68 (m, 2H), 2.84-2.98 (m, 9H), 3.10 (s, 2H), 3.22 (s, 2H), 3.25-3.68 (m, 12H), 3.85 (dd, J=8.6, 2.0 Hz), 3.93 (d, J=10 Hz), 4.05 (m, 1H), 4.13 (m, 1H), 4.22 (q, J=10 Hz), 4.48-4.58 (m, 1H), 4.63-4.75 (m, 2H), 4.81 (d, J=7.8 Hz, 2H), 5.02-5.17 (m, 3H), 6.77 (s, 2H), 7.10 (m, 1H), 7.15-7.29 (m, 8H), 7.82-8.01 (m, 2H), 8.16 (d, J=8.4 Hz, 1H), 8.24 (s, 1H), 8.35 (m, 1H); LC-MS m/z (ES$^+$), 1337.03 (M+H)$^+$, 8.50 min; HRMS m/z for $C_{66}H_{95}N_8O_{21}Na_2$ (M–H+2Na)$^+$ calcd, 1381.6407; found, 1381.6428.

4-(tert-butyidiphenylsilyloxy)butan-1-ol: To a solution of 1,4-butanediol was added sodium hydride (1.0 g of a 60% dispersion in mineral oil). This mixture was allowed to stir at an ambient temperature for 1 h, before TBDPSCI (5.0 mL, 18.2 mmol) was added. The mixture was stirred overnight at an ambient temperature. The reaction mixture was poured into water and extracted with ether (3×100 mL). The combined extract was washed with water and brine and dried over sodium sulfate. Filtration and concentration gave an oily residue, which was purified via radial chromatography on a 4 mm plate eluting with 25% ethyl acetate in hexanes, followed by 50% ethyl acetate in hexane. This gave 3.36 g (56%) of desired product as clear oil. $^1$H NMR (CDCl$_3$); δ1.24 (s, 9H), 1.65 (m, 4h), 3.65 (m, 4H), 7.40 (m, 6H), 7.64 (d, 2H, J=1.5 Hz).

4-(tert-butyidiphenylsilyloxy)butanal: To a solution of the 4-(tert-butyidiphenylsilyloxy)butan-1-ol (0.5 g, 1.5 mmol) in dichloromethane (20 mL) was added Dess-Martin periodinane (775 mg, 1.83 mmol). The mixture was stirred for 1 h. The reaction mixture was poured into hexanes and the resulting white precipitant was removed via filtration. The solution was concentrated to give form a slurry, which was dissolved in dichloromethane (5 mL) and again poured into hexanes resulting in the precipitation of white solid. The solids were removed via filtration and the resulting solution was concentrated. This gave 475 mg (97%) of a clear oil: $^1$H NMR (CDCl$_3$); δ1.04 (s, 9H), 1.89 (m, 2H), 2.55 (m, 2H), 3.69 (t, 2H, J=6.1 Hz)), 7.38 (m, 6H), 7.63 (d, 4H, J=1.7 Hz), 9.79 (t, 1H, J=1.8 Hz).

2-(3-(tert-butyidiphenylsilyloxy)propyl)oxazolidine (12): A mixture of the 4-(tert-butyidiphenylsilyloxy)butanal (235 mg, 0.72 mmol) in benzene (3 ml) was added dropwise to a solution of hydroxy ethylamine (44 μL, 0.72 mmol) in benzene (3 mL). Powdered molecular sieves (4 Å, 600 mg) were added and the mixture was stirred for 1.5 h, before being filtered through a 20 μm Millipore syringe filter and concentrated. This gave 12 which was used directly and immediately in the synthesis of 13 (infra): $^1$H NMR (C$_6$D$_6$); δ1.18 (s, 9H), 1.65-1.82 (m, 2H), 2.62 (m, 2H), 3.33 (dd, 3H, J=6.1, 7.5 Hz), 3.69 (t, 3H, J=6.1 Hz), 4.26 (t, 1H), 7.23 (dd, 6H, J=1.9, 3.1 Hz), 7.79 (m, 4H).

3-(3-(((9H-fluoren-9-yl)methoxy)carbonylamino)propanamido)-4-((2S,3R,4S,5S,6S)-3,4,5-triacetoxy-6-(methoxycarbonyl)-tetrahydro-2H-pyran-2-yloxy)benzyl 2-(3-(tert-butyidiphenylsilyloxy)propyl)oxazolidine-3-carboxylate (13): To the benzyl alcohol (50 mg, 0.067 mmol) in dichloromethane (10 mL) was added pyridine (63 μL, 0.8 mmol). The mixture was cooled to −78° C. and diphosgene (16 μL, 0.134 mmol) was added. The mixture was stirred for 1 h. The oxazolidine 12 (formed from 65 mg of 4-(tert-butyidiphenylsilyloxy)butanal) was added as a dichloromethane solution (3 mL) dropwise down the cooled inside wall of the reaction flask. The reaction mixture was allowed to slowly warm to −20° C. over several hours. The reaction mixture was poured into ethyl acetate and washed with saturated aqueous sodium bicarbonate, water and brine. The organic phase was dried over sodium sulfate, filtered and concentrated. The resulting residue was purified via radial chromatography eluting with dichloromethane. The major UV active band (254 nm) was collected and concentrated to give 54 mg (70%) of 13: $^1$H NMR (d6-DMSO); δ0.95 (s, 9H), 1.55 (m, 2H), 1.63 (m, 1H), 1.82 (m, 1H), 1.98 (m, 9H), 2.4-2.52 (m, 2H), 3.27 (m, 2H), 3.54-3.66 (m, 6H), 3.70 (q, 1H, J=10.0 Hz), 3.98 (m, 1H), 4.20 (m, 1H), 4.26 (m, 3H), 4.70 (d, 1H, J=10.0 Hz), 4.90-5.10 (m, 4H), 5.16 (t, 1H, J=9.6 Hz), 5.48 (t, 1H, J=9.4 Hz), 5.57 (d, 1H, J=7.6 Hz), 7.0-7.15 (m, 3H), 7.29 (m, 2H), 7.36-7.45 (m, 8H), 7.57 (d, 4H, J=7.2 Hz), 7.66 (d, 2H, J=7.2 Hz), 7.86 (d, 3H, J=7.6 Hz), 8.75 (m, 1H); LC-MS m/z (ES$^+$), 1143.88 (M+H)$^+$, 13.76 min.

3-(3-(((9H-fluoren-9-yl)methoxy)carbonylamino)propanamido)-4-((2S,3R,4S,5S,6S)-3,4,5-triacetoxy-6-(methoxycarbonyl)-tetrahydro-2H-pyran-2-yloxy)benzyl 2-(3-hydroxypropyl)oxazolidine-3-carboxylate: To a mixture of the silyl ether 13 (52 mg, 0.042 mmol) in THF (2 mL) and pyridine (2 mL) was added HF-pyridine complex (400 μL). The reaction mixture was stirred for 3 h and was poured into saturated aqueous sodium bicarbonate and was extracted with ethyl acetate (3×100 mL). The combined extracts were washed with water and brine and dried over sodium sulfate, before being filtered and concentrated. The resulting oil was purified via radial chromatography on a 1 plate eluting with 5% methanol in dichloromethane to give 36 mg (86%) of a solid residue: $^1$H NMR (CD$_3$OD); δ1.55 (bs, 2H), 1.68 (m, 1H), 1.87 (m, 1H), 1.95 (s, 3H), 2.01 (m, 6H), 2.67 (oct, 2H, J=6.8 Hz), 3.30 (m, 1H), 3.50 (m, 3H), 3.65 (m, 1H), 3.69 (m, 3H), 3.82 (q, 1H, J=8.0 Hz), 4.01 (m, 1H), 4.23 (m, 1H, J=7.0 Hz), 4.25-4.40 (m, 2H), 4.47 (d, 1H, J=10.0 Hz), 5.0-5.15 (m, 3H), 5.19 (t, 1H, J=9.8 Hz), 5.28 (dd, 1H, J=6.0, 9.6 Hz), 5.39 (d, 1H, J=7.6 Hz), 5.49 (m, 3H), 7.11 (m, 2H), 7.17-7.32 (m, 3H), 7.34 (t, 2H, J=7.4 Hz), 7.62 (d, 2H, J=7.6 Hz), 7.77 (d, 2H, J=7.6 Hz), 8.07 (s, 1H); LC-MS m/z (ES$^+$), 927.87 (M+Na$^+$)$^+$, 9.79 min.

3-(3-(((9H-fluoren-9-yl)methoxy)carbonylamino)propanamido)-4-((2S,3R,4S,5S,6S)-3,4,5-triacetoxy-6-(methoxycarbonyl)-tetrahydro-2H-pyran-2-yloxy)benzyl 2-(3-oxopropyl)oxazolidine-3-carboxylate (14): To a solution of the alcohol (36 mg, 0.04 mmol) in dichloromethane (3 mL) was added Dess-Martin periodinane (20 mg, 0.048 mmol). After 1 h, an additional quantity of the Dess-Martin reagent was added (20 mg) and the reaction mixture was stirred for an additional 1 h. The reaction mixture was aspirated onto a 1 mm radial Chromatotron plate and eluted with 5% methanol in dichloromethane. This gave a quantitative yield (36 mg) of the aldehyde 14: $^1$H NMR (d6-DMSO); δ1.89 (s, 3H), 1.91 (m, 1H), 1.98 (s, 3H), 1.98 (s, 3H), 2.41 (m, 1H), 3.27 (m, 2H), 3.75 (m, 1H0, 3.61 (s, 3H), 3.77 (q, 1H, J=7.8 Hz), 3.95 (m, 1H), 4.15-4.30 (m, 3H), 4.71 (d, 2H, J=9.0 Hz), 4.97-5.13 (m, 4H), 5.16 (dd, 1H, J=7.8, 9.9 Hz), 5.45 (t, 1H, J=9.6 Hz), 5.58 (d, 1H, J=8.0 Hz), 7.05 (d, 1H, J=8.4 Hz), 7.12 (d, 1H, J=7.6 Hz), 7.29 (dd, 2H, J=5.3, 7.4 Hz), 7.39 (t, 2H, J=7.4 Hz), 7.67 (d, 2H, J=5.4 Hz), 8.77 (s, 1H), 9.57 (s, 1H), 11.97 (s, 1H); LC-MS m/z (ES$^+$), 903.96 (M+H)$^+$, 10.48 min.

3-(3-(((9H-fluoren-9-yl)methoxy)carbonylamino)propanamido)-4-((2S,3R,4S,5S,6S)-3,4,5-triacetoxy-6-(methoxycarbonyl)-tetrahydro-2H-pyran-2-yloxy)benzyl 2-(3-(3-hydroxy-2-methyl-6-((3S)-3,5,12-trihydroxy-3-(2-hydroxyacetyl)-10-methoxy-6,11-dioxo-1,2,3,4,6,11-hexahydrotetracen-1-yloxy)-tetrahydro-2H-pyran-4-ylamino)propyl)oxazolidine-3-carboxylate (16): To the aldehyde 14 (36 mg, 0.04 mmol) in a mix of acetonitrile and water (2:1; 4.5 mL total) at 0° C. was added doxorubicin-HCl (15) followed by stirring until all the solids were dissolved. The mixture was treated with a solution of sodium cyanoborohydride (1.0M solution in THF; 20 μL, 0.02 mmol)). The reaction mixture was stirred for 2 h and the mixture was poured into water and extracted repeatedly with dichloromethane (5×50 mL). The combined organics were washed with water and brine and were concentrated under reduced pressure. The resulting residue was dissolved in 5% methanol in dichloromethane and was aspirated directly onto a 1 mm radial Chromatotron plate and eluted with 20% methanol in dichloromethane. The first major band was collected to give 23.6 mg (41%) of 16: $^1$H NMR (d6-DMSO); δ1.14 (d, 3H, J=6.5 Hz), 1.36-1.60 (b, 2H), 1.62-1.78 (b, 2H), 1.97-1.99 (m, 9H), 2.14 (b, 3H), 2.95 (s, 3H), 3.18-3.32 (m, 2H), 3.52 (b, 1H), 3.60 (s, 3H), 3.75 (q, 1H, J=6.8 Hz), 4.95 (bs, 1H), 3.96 (s, 3H), 4.09 (b, 1H), 4.17 (t, 1H, J=6.5 Hz), 4.25 (d, 2H, J=6.1 Hz), 4.54 (d, 2H, J=6.3 Hz), 4.70 (d, 1H, J=10.0 Hz), 4.86 (t, 1H, J=5.9 hz), 4.92-5.07 (m, 3H), 5.15 (t, 1H, J=8.2 Hz), 5.25 (bs, 1H), 5.04 (d, 1H, J=2.0 Hz), 5.48 (t, 1H, J=10.0 Hz), 5.55 (d, 1H, J=8.0 Hz), 7.0-7.11 (m, 2H), 7.28 (m, 2H), 7.37 (t, 3H, J=7.3 Hz), 7.65 (d, 3H, J=7.0 Hz), 7.85 (d, 2H, J=7.6 Hz), 8.75 (b, 1H); LC-MS m/z (ES$^-$), 1428.9 (M−H)$^-$, 7.9 min.

(2S,3S,4S,5R,6S)-6-(2-(3-aminopropanamido)-4-((2-(3-(3-hydroxy-2-methyl-6-((3S)-3,5,12-trihydroxy-3-(2-hydroxyacetyl)-10-methoxy-6,11-dioxo-1,2,3,4,6,11-hexahydrotetracen-1-yloxy)-tetrahydro-2H-pyran-4-ylamino)propyl)oxazolidine-3-carbonyloxy)methyl)phenoxy)-3,4,5-trihydroxy-tetrahydro-2H-pyran-2-carboxylic acid: To a 0° C. mixture of the doxorubicin oxazolidine 16 (30 mg, 0.021 mmol) in methanol (4 mL) was added a solution of LiOH monohydrate (8.8 mg, 0.21 mmol) in water (2 mL). The mixture was stirred for 35 min and was neutralized with acetic acid (8 uL, 0.21 mmol) to a pH of approximately 7. The mixture was concentrated under reduced pressure to give a residue which was dissolved in DMF (4 mL) and treated with piperidine (1 mL). The reaction mixture was stirred for 5 min, before being concentrated under reduced pressure. The residue was purified via preparative HPLC to yield 6.1 mg (27%) of product: LC-MS m/z (ES$^+$), 1069.13 (M+H)$^+$, 5.64 min.

(2S,3S,4S,5R,6S)-6-(2-(3-(6-(2,5-dioxo-2H-pyrrol-1(5H)-yl)hexanamido)propanamido)-4-((2-(3-(3-hydroxy-2-methyl-6-((3S)-3,5,12-trihydroxy-3-(2-hydroxyacetyl)-10-methoxy-6,11-dioxo-1,2,3,4,6,11-hexahydrotetracen-1-yloxy)-tetrahydro-2H-pyran-4-ylamino)propyl)oxazolidine-3-carbonyloxy)methyl)phenoxy)-3,4,5-trihydroxy-tetrahydro-2H-pyran-2-carboxylic acid (17): To a mixture of the amine (6.1 mg, 5.7 µmol) in DMF (0.2 mL) was added MC-OSu (10; 4 mg, 14 µmol) followed by DIPEA (3 µL, 17 µmol). The reaction mixture was concentrated under reduced pressure and then dissolved in a mixture of water and DMSO (1:1, 2 mL). The mixture was purified via reverse-phase preparative HPLC to yield 2.1 mg (26%) of 17 as a red solid: $^1$H NMR (CD$_3$OD); 51.1-1.25 (b, 2H), 1.29 (d, 3H, J=6.6 Hz), 1.35-1.62(b, 3H), 1.65-1.90 (b, 3H), 2.02-2.13 (m, 4H), 2.67 (s, 4H, N-hydroxy succinimide impurity), 3.00-3.10 (m, 4H), 3.41-3.57 (m, 3H), 3.57-3.70 (m, 3H), 3.81 (m, 2H), 3.94 (d, 1H, J=9.6 Hz), 4.02 (b, 1H), 4.05 (s, 3H), 4.29 (q, 1H, J=7.0 Hz), 4.71 (s, 3H), 4.73 (m, 1H), 5.06 (m, 1H), 5.12 (b, 1H), 5.49 (s, 1H), 6.78 (s, 2H), 6.82-7.09 (b, 2H), 7.57 (d, 1H, J=6.4 Hz), 7.84 (t, 1H, J=7.4 Hz), 7.95 (sd, 1H, J=7.4 Hz), 8.08 (bs, 1H); LC-MS m/z (ES$^-$), 1260.24 (M−H)$^-$, 6.49 min.

Example 2

Synthesis of β-Glucuronic Acid-based Linkers and Antibody-Drug Conjugates

Drug-linkers employing a glucuronide-based linker unit with the antimitotic agents monomethyl auristatin E (MMAE; 1a) and monomethyl auristatin F (MMAF; 1b) and doxorubicin propyloxazoline (DPO; 2) were prepared and evaluated.

β-Glucuronide Drug-Linker Preparation: The starting point for the synthesis of a β-glucuronide drug-linker with MMAF (1b) was β-glucuronide 5 bearing the free aniline and hydroxy groups (Scheme 3, infra). This compound was acylated with the acid chloride 6, and then converted to the p-nitrophenyl (PNP) carbonate 7. Reaction with MMAF (1b) afforded the carbamate 8. This molecule was converted to the desired glucuronide drug-linker 9b by first saponifying the acetate and methyl ester protecting groups with lithium hydroxide (Leenders et al., 1999, *Bioorg. Med. Chem.* 7:1597-610), Fmoc removal with piperidine and capping of the resulting free amine with maleimidocaproyl N-hydroxysuccinimidyl ester (MC-OSu; 10). A final preparative HPLC purification afforded 9b. The glucuronide-MMAE drug linker (9a) was prepared in an identical fashion starting with 5 and 1a.

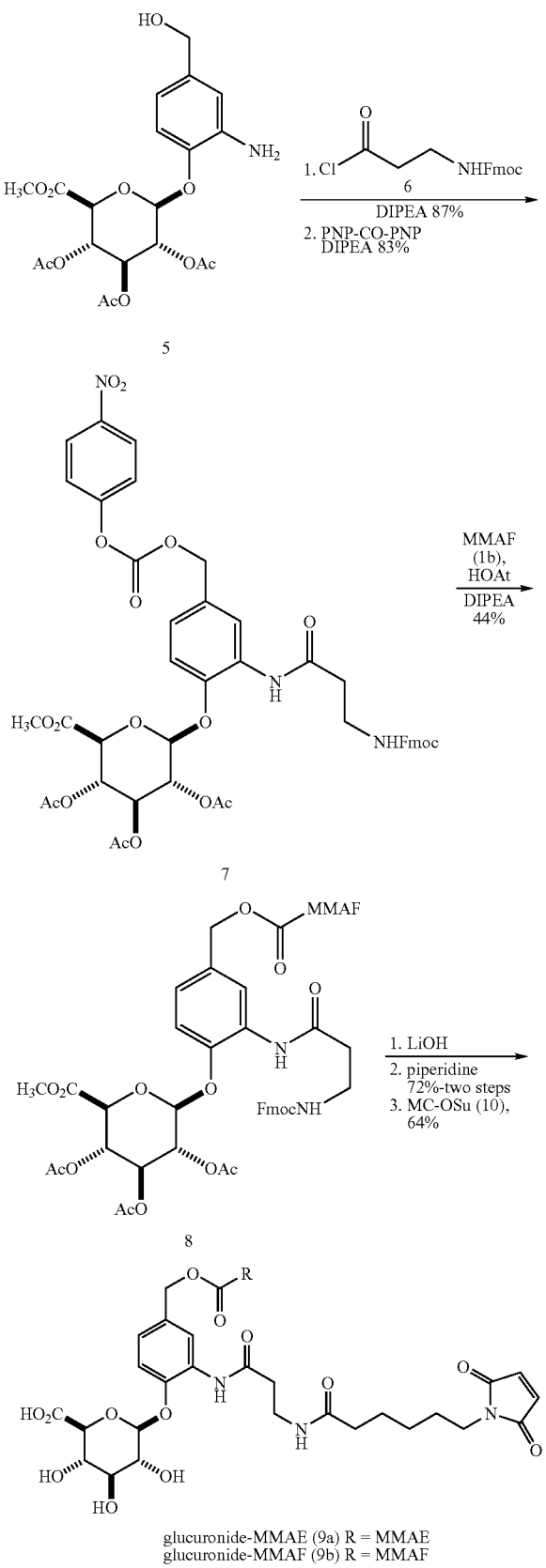

The construction of the glucuronide-based linker unit with DPO (2) involved a different strategy (Scheme 4). Intermediate 11 was activated with diphosgene and then reacted with oxazoline 12 (prepared in 3 steps from 1,4-butane diol) to afford the desired oxazoline carbamate 13. Removal of the silyl protecting group with fluoride was followed by oxidation to give aldehyde 14. This compound was used in a reductive alkylation reaction with doxorubicin-HCl (15) to give the doxorubicin derivative 16. Lastly, the β-glucuronide protecting groups and Fmoc group were removed in a 2-step sequence with lithium hydroxide and piperidine, and the resulting primary amine was capped with 10 to give the desired β-glucuronide DPO linker 17.

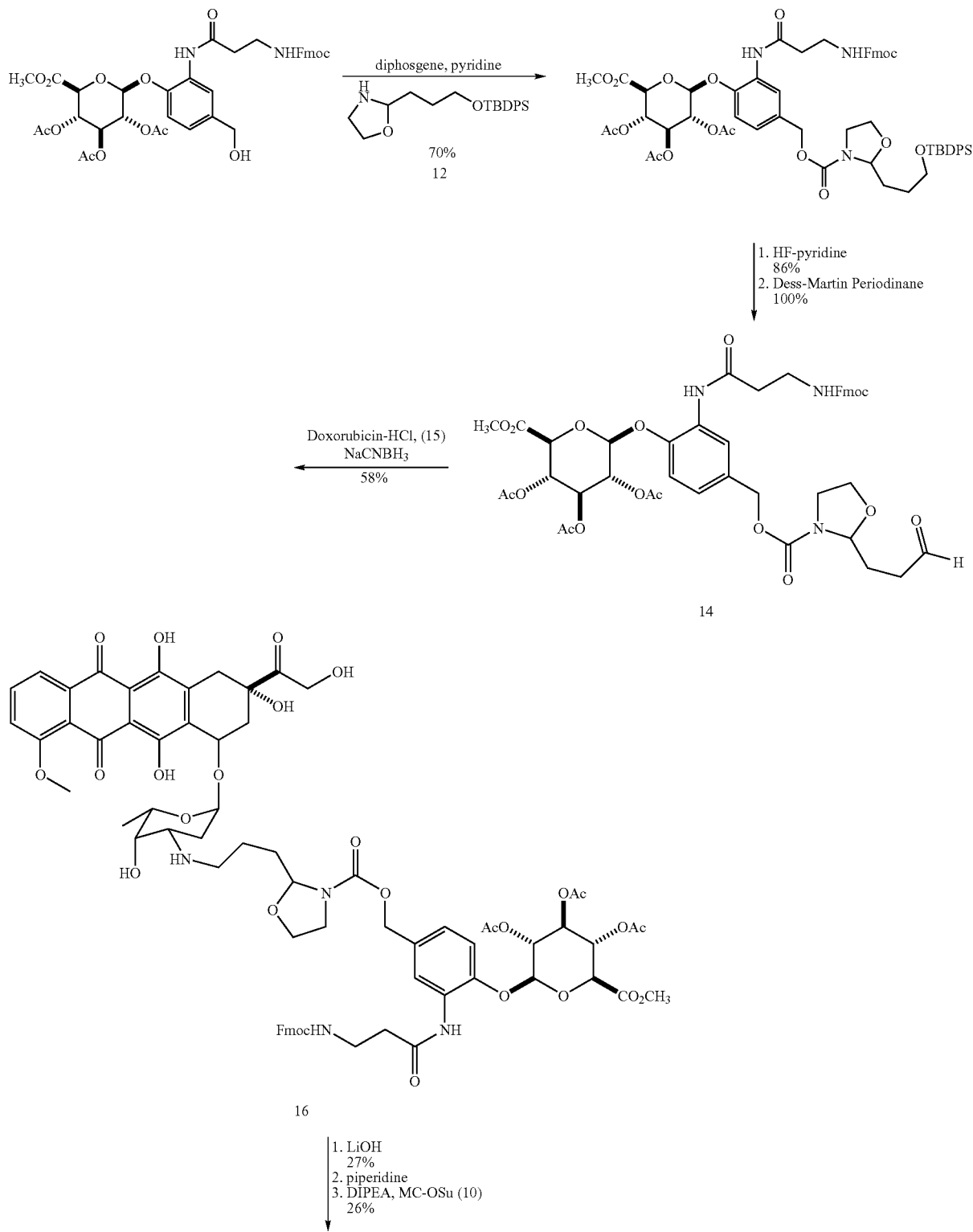

Scheme 4

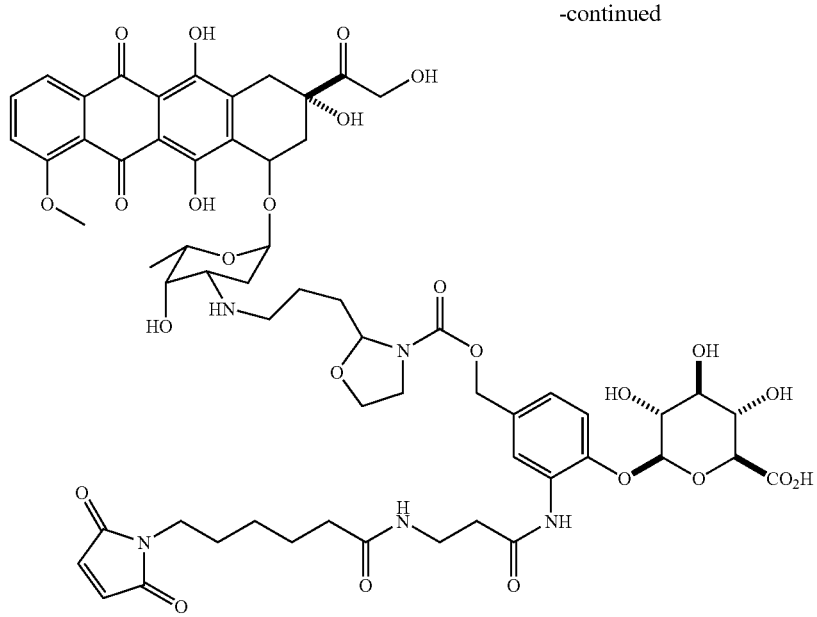

17

ADC preparation. Antibody drug conjugates (ADCS) of linker drug conjugates 9a (with MMAE), b (with MMAF) and 17 (with doxorubicin propyloxazoline (DPO)) were prepared with the chimeric mAbs AC10 (IgG1 against the CD30 antigen; (Wahl et al., 2002, *Cancer Res.* 62:3736-42) and 1F6 (IgG1 against the CD70 antigen; see, e.g., International Patent Publication WO 04/073656). The antibodies were prepared based on a method described previously (see Doronina et al., 2003, *Nat. Biotechnol.* 21:778-84).

The mAbs (>5 mg/ml) in phosphate buffered saline (PBS) containing 50 mM sodium borate, pH 8.0, were treated with dithiothreitol (DTT) or tris(2-carboxyethyl)phospine hydrochloride (TCEP) (at 10 mM final) at 37° C. for 30 min. After gel filtration (G-25, PBS containing 1 mM DTPA), thiol determination using 5,5'-dithiobis(2-nitrobenzoic acid) indicated that there were approximately eight thiols per mAb (4 thiols per mAb with TCEP). To the reduced mAb at 4° C. was added the maleimide drug derivatives (1.2 equiv./SH group) in ice-cold DMSO (20% v/v). After 1 h, the reactions were quenched with excess cysteine, the conjugates were concentrated by centrifugal ultrafiltration, gel filtered (G-25, PBS) and sterile filtered. The molar ratio of drug substitution was determined according to previously published methods (Hamblett et al., 2004, *Clin. Cancer Res.* 10:7063-70; Sun et al., 2005, *Bioconjug. Chem.* 16:1282-90). Size-exclusion HPLC was used to determine monomer within each conjugate and RP-HPLC established that there was less than 0.5% unconjugated cysteine-quenched drug.

Drug loading for the doxorubicin-containing conjugates cAC10-17 and c1F6-17 was determined by measuring the absorbance at 280 nm and 490 nm (doxorubicin absorbance). It was found that the cAC10 and c1F6 ADCs had 6.8 and 8.3 drugs/mAb, respectively. Due to the weak UV absorbance of the drug-linkers 9a and 9b, the drug per mAb ratios of the corresponding ADCs were determined through chromatographic resolution of the light and heavy chains at each drug loading level (0-1 drugs for light chains; 0-3 drugs for heavy chains) and calculation of the overall average from the peak areas at each loading level (Hamblett et al., supra; Sun et al., supra). The levels were shown to be 3.7 and 4.5 for cAC10-9a and c1F6-9a, and 7.6 and 7.0 for the cAC10-9b and c1F6-9b conjugates, respectively. The six ADCs were primarily monomeric with 2% or less aggregate being observed in the cAC10-based conjugates and 7% or less aggregate for the c1F6-based conjugates.

Results. The β-glucuronide linker system described can be included a part of an antibody drug conjugate (ADC). Under the action of β-glucuronidase (e.g., a lysosomal β-glucuronidase), the drug-linker is hydrolyzed at the glycosidic bond and undergo a 1,6-elimination with loss of carbon dioxide to liberate drug conjugated to the linker system (see Scheme 1, supra). Three ADCs based on this linker design employed the antimitotic drugs MMAE (1a) and MMAF (1b) and doxorubicin propyl oxazoline (DPO; 2), which is a labile precursor to highly potent 2-pyrrolinodoxorubicin (4), as shown in Scheme 2 (supra). Compound 4 affects apoptosis through alkylation of double-stranded DNA (33).

Example 3

*E. coil* β-glucuronidase Reactivity

The susceptibility of the β-glucuronide linkers to enzymatic cleavage was determined by treatment of the cysteine adduct of compound 9b with β-glucuronidase. A commercially available *E. coli* β-glucuronidase (EC 3.2.1.31) was in place of the human enzyme for this study. This allowed confirmation that the desired drug, MMAF (1b), was released and if any stable intermediates were formed in the process.

β-glucuronidase Reactivity. To water (90 μL) was added cysteine (12.5 μL of a 0.1 mM solution) and pH 9 borate buffer (12.5 μL of a 30 mM solution). This was followed by the addition of 9b (10 μL of a 10 mM DMSO solution). HPLC inspection after 5 min revealed complete conversion to cys-9b. To 440 mL of PBS was added the cys-9b solution (50 μL; 40 nmol) followed by a solution of *E. coli* β-glucuronidase (Sigma: E.C. 3.2.1.31 Type IX-A; 10 μL of a 1 mg/mL solution in PBS; 3.6 μg, 13 pmol) and the reaction mixture was incubated at 37° C. Aliquots (50 μL) were taken at t=0, 25, 60 and 90 min and analyzed by LC. Results were based on the area under the curve (AUC) of remaining cys-9b at each time point as a percentage of the AUC for cys-9b at t=0.

Results. The β-glucuronidase assay was performed as described above. An HPLC assay was used to monitor the loss of cys-9b (MMAF) at 37° C. The specific activity of the *E. coli* β-glucuronidase for cys-9b was 0.13 μmol/min/mg. Referring to FIG. 1, the cleavage of η-glucuronide from cys-9b resulted in rapid 1,6-elimination of MMAF (1b) which was identified by LC-MS. No MMAF-containing phenolic intermediates could be detected by LC-MS. Thus the 1,6-elimination appears to be rapid.

In a similar study with cys-17 (with doxorubicin propyloxazoline (DPO)), treatment with β-glucuronidase yielded the 2-pyrrolinodoxorubicin (4) directly as confirmed by LC-MS. Controls indicated both cys-9b and cys-17 were stable in the absence of β-glucuronidase. These two studies demonstrated that the linker is a substrate for a β-glucuronidase enzyme and that the drug is readily liberated once the η-glucuronide hydrolysis occurs.

Example 4

Rat Plasma Stability of Drug-Linker cys-9b

To determine the plasma stability of the glucuronide linker, the reactive, maleimide double bond of 9b (with MMAF) was reduced with excess DTT to afford dihydro-9b. This material was added to rat plasma and incubated at 37° C. for a period of 7 days. Aliquots were taken at various time points and the plasma proteins were precipitated, centrifuged and the supernatant was recovered. Each supernatant was analyzed by LC-MS and the total positive ion current (TIC+) chromatogram was scanned for the masses of parent compound dihydro-9b and released MMAF (1b). After 7 days, the TIC+ for dihydro-9b (including the ring-opened succinimide hydrolysis adduct) was 89% of sample taken immediately after dihydro-9b was injected into plasma. Free drug 1b could be detected but was not quantified. Assuming first order kinetics, extrapolation of these data suggest a half-life of 81 days for dihydro-9b. In a parallel experiment, the rat plasma stability of the maleimide reduced Val-Cit-PABA linked MMAF was determined, just as with dihydro-9b. This drug-linker displayed a half-life of 6.25 days.

This study demonstrates the improved stability of the β-glucuronide linker system relative to disulfide and hydrazone-based systems which are reported to have shorter half-lives for drug release.

Example 5

In vitro Evaluation of Cytotoxic Agents and ADCs

The linker-drug conjugates and ADCs compounds 9a (with MMAE), 9b (MMAF) and 17 (with doxorubicin propyloxazoline (DPO) with the mAbs AC10 (IgG1 against the CD30 antigen) and 1F6 (IgG1 against the CD70 antigen) were prepared. The ADCs (c1F6-9a and cAC10-9a, c1F6-9b and cAC10-9b, and c1F6-17 and cAC10-17) were evaluated for cytotoxic activity on a CD30+ cell line (Karpas 299) and two CD70+ renal cell carcinoma (RCC) lines, 786-O and Caki-1.

ADCs. The ADCs were prepared as described above.
In vitro growth inhibition. Cells were collected and plated in 96 well black-sided plates at a density of 10,000 cells/well in 150 μL of medium. Serial dilutions of the ADC (50 μL) were added, and incubation was carried out for 92 h at 37° C. After addition of ADC, cultures were incubated to 96 h at 37° C. Resazurin (0.25 mM, 50 μL, Sigma, St. Louis, Mo.) in medium was added and incubation was continued for 4 h. The plates were read on a Fusion HT microplate reader (Packard, Meriden, Conn.) using an excitation wavelength of 525 nm and an emission wavelength of 590 nm. Data from all assays were reduced using GraphPad Prism Version 4 for Windows (GraphPad Software, San Diego, Calif.). The $IC_{50}$ concentrations compared to untreated control cells were determined using a 4 parameter curve fits.

Results. In vitro evaluation of both MMAE (1a) and 18 (the esterase labile prodrug of 2-pyrrolinodoxorubicin (4)) revealed these compounds to be highly cytotoxic (below 0.2 nM) on the CD70+ cell lines Caki-1 and 786-O and the CD30+ line Karpas 299 (Table 7). Compound 18 proved to be 300-6500 fold more cytotoxic than doxorubicin (15), which is consistent with previous findings for this class of doxorubicin derivatives (Farquhar et al., 1998, *J. Med. Chem.* 41:965-72). In contrast to 1a and 18, the free carboxylic acid MMAF (1b) was significantly less active on these cell lines with $IC_{50}$ values in the 100-200 nM range (Doronina et. al., 2006, *Bioconjug Chem.* 17(1):114-124). The negative charge associated with the carboxylate group of 1b leads to reduced cytotoxic activity, presumably due to impaired intracellular access.

Figure 2:
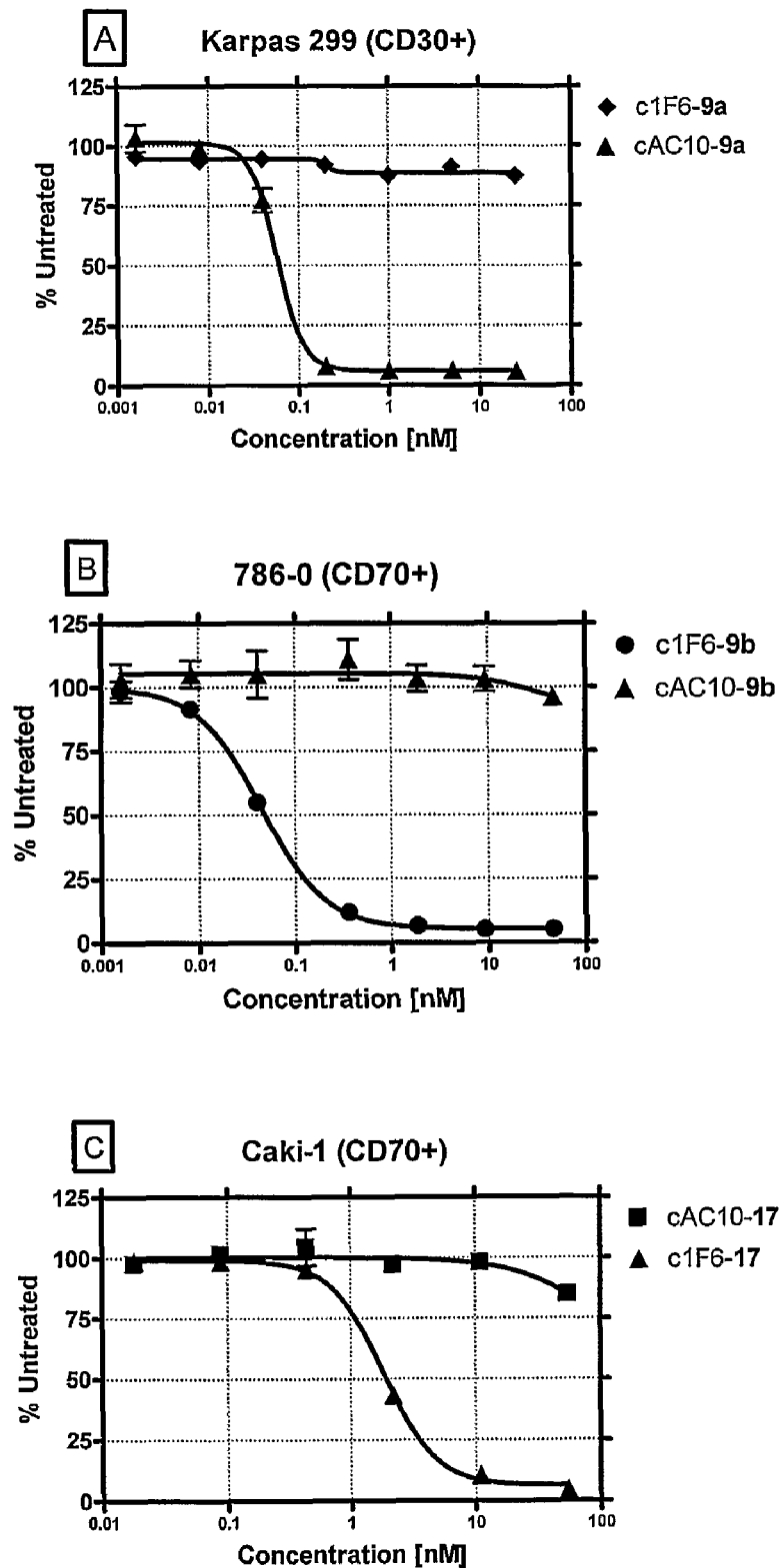
FIG. 2 shows in vitro cytotoxic activity of ADCs on CD30+ and CD70+ cancer cell lines: (A) Karpas 299 (CD30+) ALCL cells treated with anti-CD30 ADC cAC10-9a and non-binding control c1F6-9a for 96 hours. (B) 786-O (CD70+) RCC cells treated with anti-CD70 ADC c1F6-9b and non-binding control cAC10-9b for 96 hours. (C) Caki-1 (CD70+) RCC cells treated with c1F6-17 and nonbinding control cAC10-17. Results are shown as mean ±SD.

In vitro evaluation of cAC10 and c1F6 conjugates of 9a demonstrated that the linker delivered active drug to the target cells with immunologic specificity (FIG. 2). A comparison of the activity of the two conjugates on the CD30+ line Karpas 299 (FIG. 2A) revealed that the anti-CD30 conjugate cAC10-9a titrated to an $IC_{50}$ value of 0.06 nM (drug content), where the non-binding conjugate c1F6-9a had no cytotoxic activity up to 30 nM, the highest concentration tested. The anti-CD70 conjugate c1F6-9a was quite potent on the CD70+ cell line Caki-1 ($IC_{50}$ 0.45 nM) (FIG. 2C).

The ADCs of 9b effectively delivered 1b to the targeted cells. Conjugates of 9b displayed immunologic specificity and were highly effective against the CD70+ lines Caki-1 and 786-O (FIGS. 2B and 2C, respectively) with $IC_{50}$ values of 0.08 and 0.20 nM, respectively. The corresponding non-binding cAC10-9b was inactive on these cell lines representing specificity levels of >250-fold. The anti-CD30 conjugate cAC10-9b was highly effective on the CD30+ line Karpas 299 with an $IC_{50}$ value of 50 μM. Conjugates of doxorubicin drug-linker 17 gave the same general profile with effective cell kill on antigen positive cell lines and specificity values >16-fold.

TABLE 7

Characterization and in vitro cytotoxic activity of free drugs and ADCs

| Compound | Target antigen | Active drug | Drug loading | % Aggregation | Caki-1 (CD70+, CD30−) $IC_{50}$ drug nM | 786-O (CD70+, CD30−) $IC_{50}$ drug nM | Karpas 299 (CD30+, CD70−) $IC_{50}$ drug nM |
|---|---|---|---|---|---|---|---|
| 1a | — | — | — | — | 0.11 | 0.19 | 0.09 |
| 1b | — | — | — | — | 270 | 300 | 100 |
| 15 | — | — | — | — | 110 | 65 | 29 |
| 18 | — | 4 | — | — | 0.04 | 0.01 | 0.1 |
| c1F6-9a | CD70 | 1a | 4.5 | 2 | 0.45 | — | >30 |
| cAC10-9a | CD30 | 1a | 3.7 | 2 | — | — | 0.06 |
| c1F6-9b | CD70 | 1b | 7 | 7 | 0.08 | 0.2 | — |
| cAC10-9b | CD30 | 1b | 7.6 | <1 | >50 | >50 | 0.05 |
| c1F6-17 | CD70 | 4 | 8.3 | 3.5 | 2.0 | 2.7 | >55 |
| cAC10-17 | CD30 | 4 | 6.8 | <1 | >45 | >45 | 1.2 |

[a]Cells were exposed to the test agents for 96 h, and viability was determined using rezasurin metabolism as a measure of cytotoxic activity. The $IC_{50}$ values were determined compared to untreated cells.

Example 6

In vivo Evaluation of cAC10-9a and c1F6-9b

For the in vivo evaluation, two ADCs of the auristatin derivatives 9a and 9b were selected. The maximum tolerated dose (MTD) of cAC10-9a (4 drugs/mAb) was determined in female Balb/c mice. cAC10-9a was well tolerated at 100 mg/kg, but toxic at 150 mg/kg. Conjugate c1F6-1b was well tolerated at 25 mg/kg, but was toxic at the 50 mg/kg dose. The MTDs of the glucuronide ADCs therefore appear to be comparable to the corresponding peptide-linked MMAE (Doronina et al., 2003, *Nat. Biotechnol.* 21:778-84) and MMAF ((Doronina et al., 2006, *Bioconjug. Chem.* 17(1):114-124) ADCs that were previously described.

Figure 3:
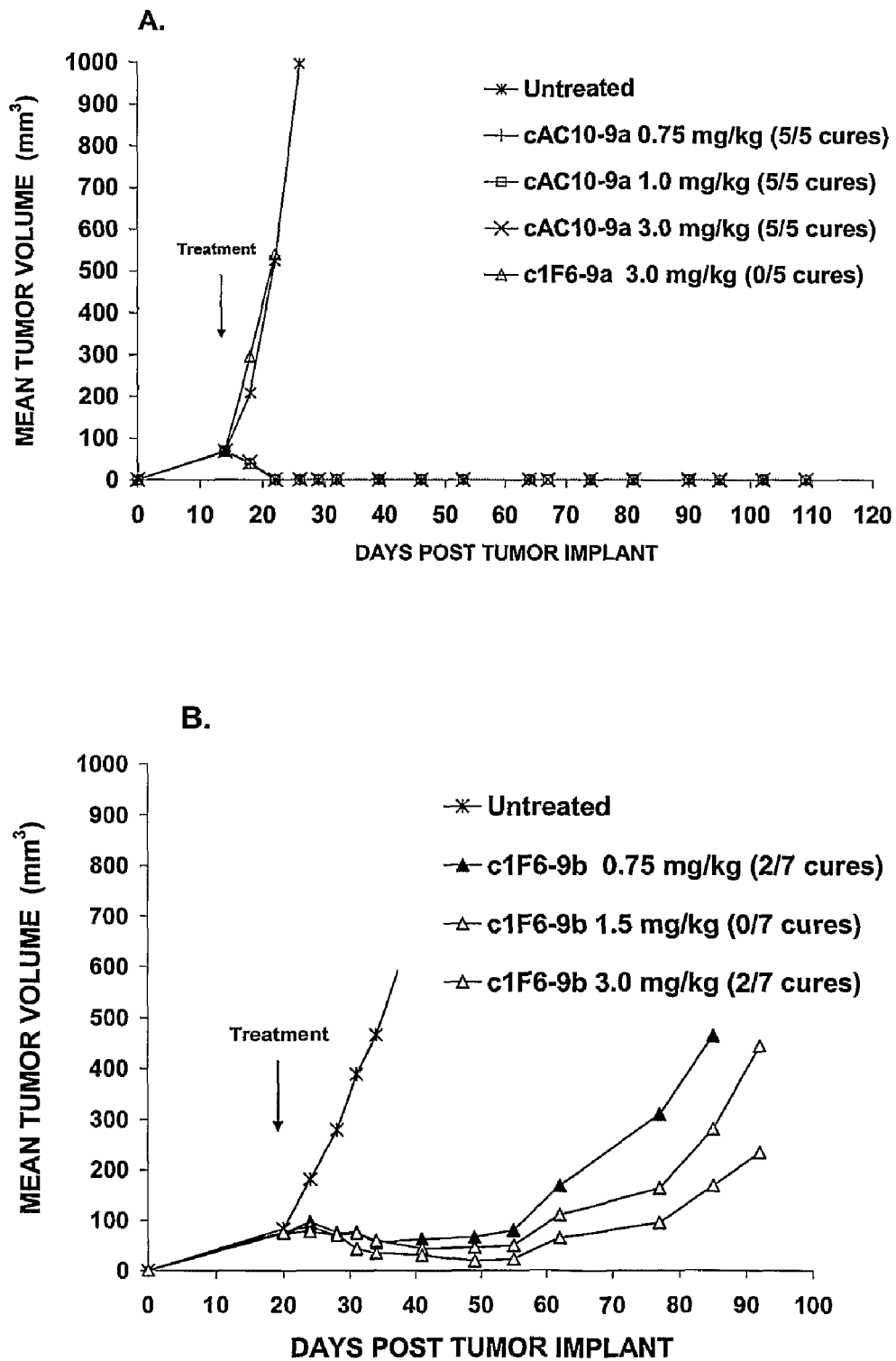
FIG. 3 shows in vivo studies with ADCs. Panel A shows the effect of cAC10-9a (with MMAE) on CD30+ Karpas 299 (ALCL) subcutaneous tumor bearing SCID mice. A single treatment (arrow: day 14) of mice with 0.75 (+), 1.0 (□), and 3 (x) mg/kg gave cures in 5/5 animals for each group. A dose of 3 mg/kg of non-binding control conjugate c1F6-9a (Δ) resulted in no tumor response as with the untreated group (·). Panel B shows the effect of c1F6-9b (with MMAF) on CD70+ 786-O (RCC) subcutaneous tumor bearing SCID mice. Single treatment (arrow: day 20) of mice with 0.75 (▲), 1.5 (Δ), and 3.0 (Δ) mg/kg single dose gave tumor regressions. Cures (2/7) were seen in the 0.75 and 3 mg/kg dose groups. All animals in the untreated group (x) were sacrificed on or before day 40.

An in vivo therapy experiments with cAC10-9a was undertaken in nude mice with subcutaneous Karpas 299 ALCL tumors. The animals (5 per group) were treated with a single intravenous dose of cAC10-9a at 0.5, 1.0 and 3 mg/kg (mAb component) on day 14 post tumor implant at which time the tumors were staged (mean=70 mm$^3$) and rapidly growing. Specificity was determined using c1F6-9a as a non-binding control ADC that was injected at 3 mg/kg dose. Cures were obtained in all animals treated with cAC10-9a at each of the three dosing levels (FIG. 3A). In contrast, the non-binding ADC c1F6-9a had no antitumor effect. Since the MTD of cAC10-9a is approximately 100 mg/kg, the therapeutic index was >200 which is at least as pronounced at the Val-Cit PABA-based MMAE ADC reported earlier (Doronina et al., 2003, *Nat. Biotechnol.* 21:778-84).

The effects of c1F6-9b were determined in mice with subcutaneous 786-0 renal cell carcinoma implants. Significant levels of antitumor activity were obtained at all three dose levels (0.75, 1.5 and 3.0 mg/kg), again without any signs of toxicity or adverse events (FIG. 3B). As with the c1F6-9a ADC, this was achieved at a small fraction of the MTD.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

No license is expressly or implicitly granted to any patent or patent applications referred to or incorporated herein. The discussion above is descriptive, illustrative and exemplary and is not to be taken as limiting the scope defined by any appended claims.

Various references, including patent applications, patents, and scientific publications, are cited herein, the disclosures of each of which is incorporated herein by reference in its entirety.

The invention claimed is:

1. A ligand drug conjugate compound having the formula:

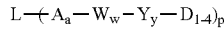

or a pharmaceutically acceptable salt or solvate thereof, wherein:

L- is a Ligand unit;
-$A_a$-$W_w$-$Y_y$- is a Linker unit (LU),
-A- is an optional Stretcher unit,
a is 0, 1 or 2, each —W— is independently a Glucuronide unit having one of the formulae:

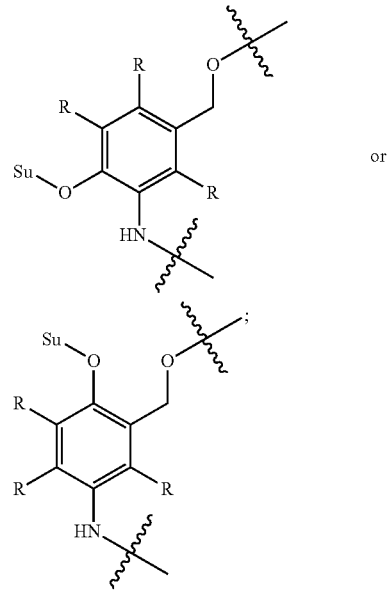

Su is a Sugar moiety
each R is independently hydrogen, a halogen, —CN, or —NO$_2$;
w is an integer ranging from 1 to 2,
—Y— is an optional self-immolative spacer unit,
y is 0, 1 or 2;
p ranges from 1 to 20;
-D is a Drug unit and wherein the wavy lines indicates covalent attachment within rest of the compound.

2. The ligand drug conjugate compound of claim 1, wherein L is an antibody.

3. The ligand drug conjugate compound of claim 2, wherein the antibody is a humanized, chimeric, or human antibody or an antigen binding antibody fragment of an antibody.

4. The ligand drug conjugate compound of claim 3, wherein the antibody binds to CD19, CDD30, CD33, and CD70.

5. The ligand drug conjugate compound of claim 4, wherein the antibody binds to CD30 or CD70.

6. The ligand drug conjugate compound of claim 1, wherein w is 1.

7. The ligand drug conjugate compound of claim 6, having one of the following formulae:

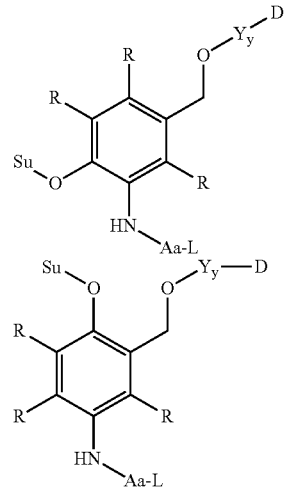

8. The ligand drug conjugate compound of claim 7, having the formula:

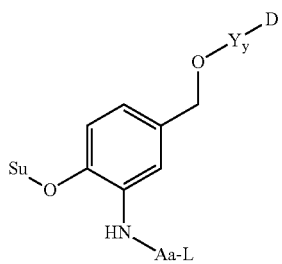

9. The ligand drug conjugate compound of claim 8, having the formula:

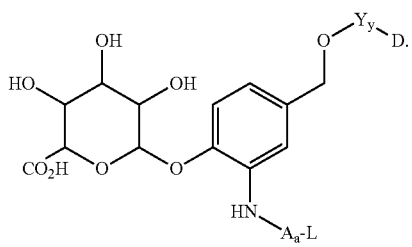

10. The ligand drug conjugate compound of claim 9, having the formula:

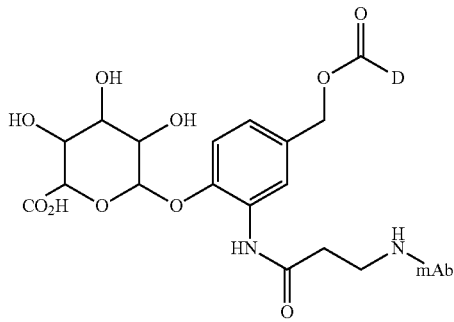

wherein mAb is a monoclonal antibody.

11. The ligand drug conjugate compound of claims 1, 6, 7, 8, 9 or 10, wherein the Drug moiety is selected from Formulas $D_E$ and $D_F$:

or a pharmaceutically acceptable salt or solvate thereof; and the wavy line of $D_F$ and $D_E$ indicates a covalent attachment to a Linker Unit or a Ligand Unit;

wherein, independently at each location:
$R^2$ is selected from H or $C_1$-$C_8$ alkyl;
$R^3$ is selected from H, $C_1$-$C_8$ alkyl, $C_3$-$C_8$ carbocycle, aryl, $X^1$-aryl, $X^1$—($C_3$-$C_8$ carbocycle), $C_3$-$C_8$ heterocycle or $X^1$—($C_3$-$C_8$ heterocycle);
$R^4$ is selected from H, $C_1$-$C_8$ alkyl, $C_3$-$C_8$ carbocycle, aryl, $X^1$-aryl, $X^1$—($C_3$-$C_8$ carbocycle), $C_3$-$C_8$ heterocycle and $X^1$—($C_3$-$C_8$ heterocycle);
$R^5$ is selected from H and methyl;
or $R^4$ and $R^5$ jointly form a carbocyclic ring and have the formula —$(CR^aR^b)_n$— wherein $R^a$ and $R^b$ are independently selected from H, $C_1$-$C_8$alkyl or $C_3$-$C_8$ carbocycle and n is selected from 2, 3, 4, 5 and 6;
$R^6$ is selected from H and $C_1$-$C_8$ alkyl;
$R^7$ is selected from H, $C_1$-$C_8$ alkyl, $C_3$-$C_8$ carbocycle, aryl, $X^1$-aryl, $X^1$—($C_3$-$C_8$ carbocycle), $C_3$-$C_8$ heterocycle and $X^1$—($C_3$-$C_8$ heterocycle);
each $R^8$ is independently selected from H, OH, $C_1$-$C_8$ alkyl, $C_3$-$C_8$ carbocycle or O—($C_1$-$C_8$ alkyl);
$R^9$ is selected from H and $C_1$-$C_8$ alkyl;
$R^{10}$ is selected from aryl and $C_3$-$C_8$ heterocycle;
Z is O, S, NH, or $NR^{12}$, wherein $R^{12}$ is $C_1$-$C_8$ alkyl;
$R^{11}$ is selected from H, $C_1$-$C_{20}$ alkyl, aryl, $C_3$-$C_8$ heterocycle, —$(R^{13}O)_m$—$R^{14}$ or —$(R^{13}O)_m$—$CH(R^{15})_2$;
m is an integer ranging from 0-1000;
$R^{13}$ is $C_2$-$C_8$ alkyl;
$R^{14}$ is H or $C_1$-$C_8$ alkyl;
each occurrence of $R^{15}$ is independently H, COOH, —$(CH_2)_n$—$N(R^{16})_2$, —$(CH_2)_n$—$SO_3H$, or —$(CH_2)_n$—$SO_3$—$C_1$-$C_8$ alkyl;
each occurrence of $R^{16}$ is independently H, $C_1$-$C_8$ alkyl, or —$(CH_2)_n$—COOH;
$R^{18}$ is selected from —$C(R^8)_2$—$C(R^8)_2$-aryl, —$C(R^8)_2$—$C(R^8)_2$—($C_3$-$C_8$ heterocycle), or —$C(R^8)_2$—$C(R^8)_2$—($C_3$-$C_8$ carbocycle);
$X^1$ is $C_1$-$C_{10}$ alkylene; and
n is an integer ranging from 0 to 6.

$D_E$

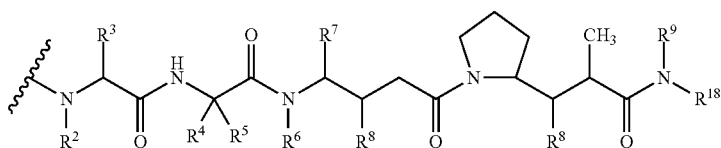

$D_F$

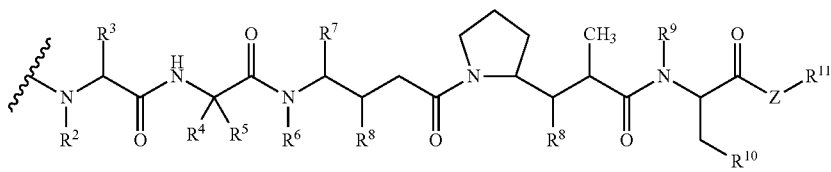

12. The ligand drug conjugate compound of claim 1, wherein D is Formula $D_F$:

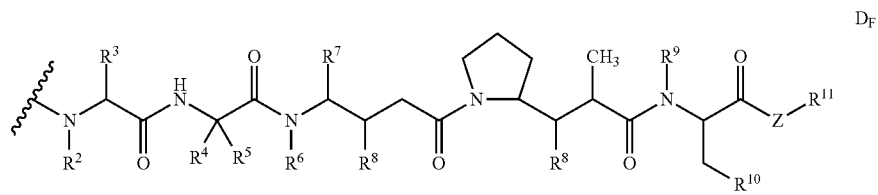

$D_F$ and the wavy line of $D_F$ indicates a covalent attachment to a Linker Unit or a Ligand Unit.

13. The ligand drug conjugate compound of claim 1, wherein D has the formula:

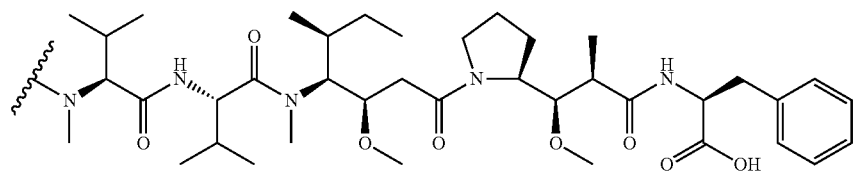

and the wavy line of D indicates a covalent attachment to a Linker Unit or a Ligand Unit.

14. The ligand drug conjugate compound of claim 1, wherein D is has the Formula $D_E$:

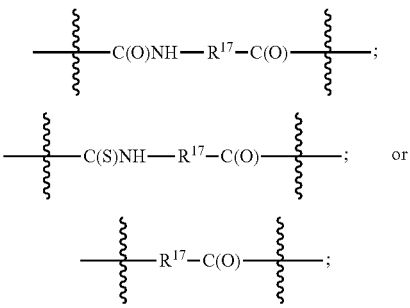

and the wavy line of $D_E$ indicates a covalent attachment to a Linker Unit or a Ligand Unit.

15. The ligand drug conjugate compound of claim 14, wherein D has the formula:

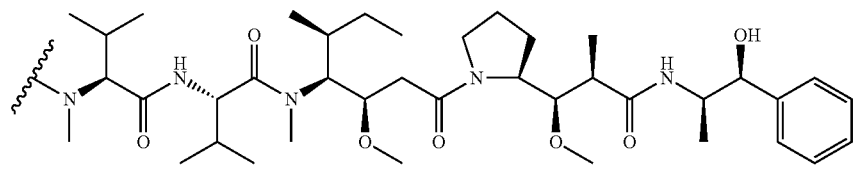

and the wavy line of D indicates a covalent attachment to a Linker Unit or a Ligand Unit.

16. The ligand drug conjugate compound of claim 1, wherein p is 2 to about 6.

17. The ligand drug conjugate compopund of claim 1, wherein p is 2 to about 4.

18. The ligand drug conjugate compound of claim 6 wherein A is selected from the formulae:

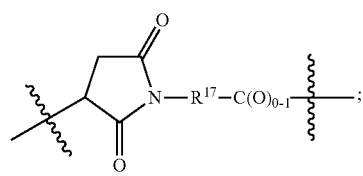

-continued

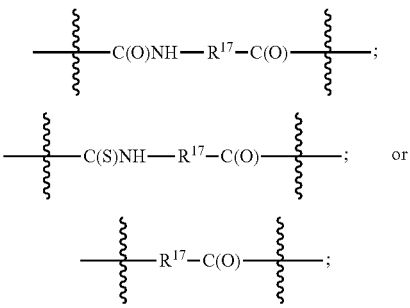

wherein $R^{17}$ is $C_1$-$C_{10}$ alkylene-, —$C_3$-$C_8$ carbocyclo-, —O—($C_1$-$C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$ alkylene-, —($CH_2CH_2O$)$_r$—, —($CH_2CH_2O$)$_r$—$CH_2$—; —($CH_2CH_2O$)$_r$— —$CH_2$—$CH_2$—; and r is an integer ranging from 1-10.

19. The ligand drug conjugate compound of claim 18, wherein A is selected from the formulae:

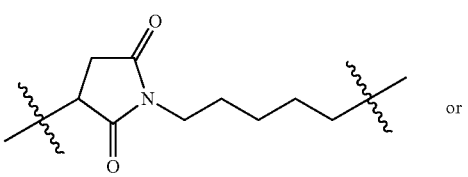

-continued

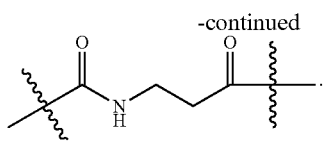

20. The ligand drug conjugate compound of claim 1, wherein D is doxorubicin, calicheamicin, staurosporine, amino CBI minor groove binder SN26597 or DM1.

21. A pharmaceutical composition comprising an effective amount of the ligand drug conjugate compound of claim 1, and a pharmaceutically acceptable diluent, carrier or excipient.

22. The pharmaceutical composition of claim 21 further comprising a therapeutically effective amount of a chemotherapeutic agent.

23. The ligand drug conjugate compound of claim 6, wherein a is 1 or 2.

24. The ligand drug conjugate compound of claim 1, wherein Y is a carbonyl group (—CO)— or a p-aminobenzyl alcohol group whose phenylene portion is substituted with $Q_m$ wherein Q is $C_1$-$C_8$ alkyl, —O—($C_1$-$C_8$ alkyl), -halogen, -nitro or -cyano; and m is an integer ranging from 0-4.

25. The ligand drug conjugate compound of claim 6, having the formula:

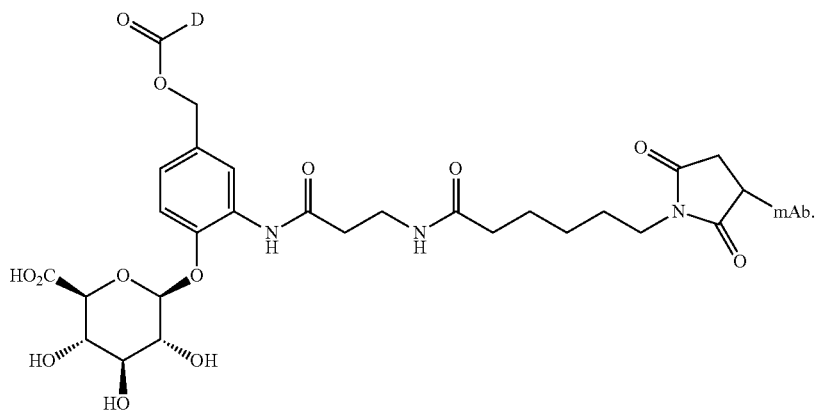

26. The ligand drug conjugate compound of claim 25, wherein D has the formula:

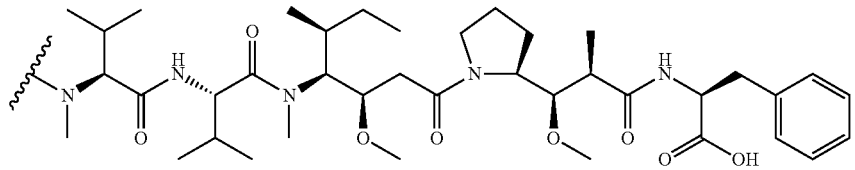

and the wavy line of D indicates a covalent attachment to a Linker Unit or a Ligand Unit.

27. The ligand drug conjugate compound of claim 25, wherein D has the formula:

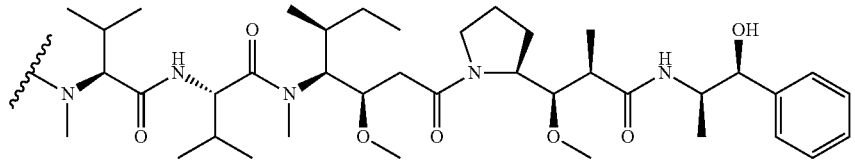

and the wavy line of D indicates a covalent attachment to a Linker Unit or a Ligand Unit.

* * * * *